United States Patent [19]

Aloup et al.

[11] Patent Number: 5,726,175
[45] Date of Patent: Mar. 10, 1998

[54] IMIDAZO[1,2-A]INDENO[1,2-E]PYRAZINE-2-CARBOXYLIC ACID DERIVATIVES, PREPARATION THEREOF AND DRUGS CONTAINING SAME

[75] Inventors: Jean-Claude Aloup, Villeneuve Le Roi; François Audiau, Charenton Le Pont; Michel Barreau, Montgeron; Dominique Damour, Orly; Arielle Genevois-Borella, Thiais; Patrick Jimonet, Villepreux; Serge Mignani, Chatenay-Malabry; Yves Ribeill, Villemoisson sur Orge, all of France

[73] Assignee: Rhone-Poulenc Rorer S.A., Antony, France

[21] Appl. No.: 765,817

[22] PCT Filed: Jul. 17, 1995

[86] PCT No.: PCT/FR95/00951

§ 371 Date: Jan. 17, 1997

§ 102(e) Date: Jan. 17, 1997

[87] PCT Pub. No.: WO96/02544

PCT Pub. Date: Feb. 1, 1996

[30] Foreign Application Priority Data

Jul. 20, 1994 [FR] France ................. 94 08997

[51] Int. Cl.⁶ .............. C07D 487/04; C07D 487/14; A61K 31/50
[52] U.S. Cl. .............................. 514/250; 544/343
[58] Field of Search .................. 544/343; 514/250

[56] References Cited

U.S. PATENT DOCUMENTS

| | | | |
|---|---|---|---|
| 4,242,344 | 12/1980 | Lumma | 424/251 |
| 4,291,033 | 9/1981 | Barnes et al. | 424/250 |
| 4,333,934 | 6/1982 | Barnes et al. | 424/250 |
| 4,474,784 | 10/1984 | Barnes et al. | 424/250 |
| 4,644,002 | 2/1987 | Barnes et al. | 514/292 |
| 5,102,885 | 4/1992 | Watjen et al. | 514/250 |
| 5,306,819 | 4/1994 | Albaugh et al. | 544/346 |

FOREIGN PATENT DOCUMENTS

| | | |
|---|---|---|
| WO 9306103 | 4/1993 | WIPO . |
| WO 9320077 | 10/1993 | WIPO . |
| WO 9407893 | 4/1994 | WIPO . |
| WO 9422865 | 10/1994 | WIPO . |

*Primary Examiner*—Mukund J. Shah
*Assistant Examiner*—Bruck Kifle
*Attorney, Agent, or Firm*—Finnegan, Henderson, Farabow, Garrett & Dunner, L.L.P.

[57] ABSTRACT

A compound of formula (I):

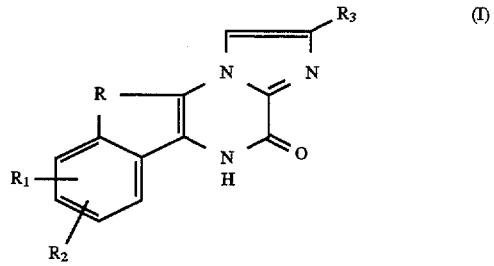

wherein R, $R_1$, $R_2$, and $R_3$ are as defined in the application, salts thereof, preparation thereof and drugs containing same.

64 Claims, No Drawings

IMIDAZO[1,2-A]INDENO[1,2-E]PYRAZINE-2-CARBOXYLIC ACID DERIVATIVES, PREPARATION THEREOF AND DRUGS CONTAINING SAME

The present invention relates to compounds of formula:

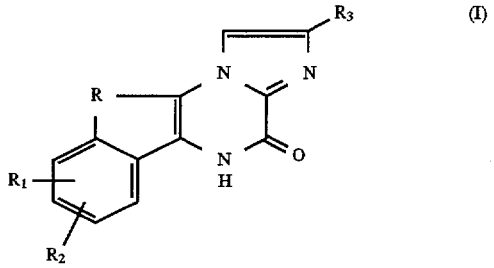

their salts, their preparation and the medications containing them.

In formula (I),

R denotes an N-alk, $C(R_4)R_5$, $CH-R_6$ or $C=R_7$ radical, $R_1$ and $R_2$, which are identical or different, denote hydrogen or halogen atoms or radicals which are alkyl, alkoxy, amino, $-N=CH-N(alk)alk'$, nitro, cyano, phenyl, imidazolyl, $SO_3H$, hydroxyl, polyfluoroalkoxy, carboxyl, alkoxycarbonyl, $-NH-CO-NR_{11}R_{12}$, $-N(alk)-CO-NR_{11}R_{12}$, $-N(alk-Ar)-CO-NR_{11}R_{12}$, $-NH-CS-NR_{11}R_{12}$, $-N(alk)-CS-NR_{11}R_{12}$, $-NH-CO-R_{11}$, $-NH-CS-R_{24}$, $-NH-C(=NR_{27})-NR_{10}R_{12}$, $-N(alk)-C(=NR_{27})-NR_{10}R_{12}$, $-CO-NR_{10}R_{12}$, $-NH-SO_2-NR_{10}R_{12}$, $-N(alk)-SO_2-NR_{10}R_{12}$, $-NH-SO_2-CF_3$, $-NH-SO_2$-alk, $-NR_{10}R_{13}$, $-S(O)_m$-alk-Ar, $-SO_2-NR_{10}R_{12}$, 2-oxo-1-imidazolidinyl in which position 3 is optionally substituted by an alkyl radical or 2-oxo-1-perhydropyrimidinyl in which position 3 is optionally substituted by an alkyl radical, $R_3$ denotes a carboxyl, alkoxycarbonyl or carboxamido radical, $R_4$ denotes an alkyl, -alk-Het or phenylalkyl radical in which the phenyl nucleus is optionally substituted by one or more substituents chosen from halogen atoms and alkyl, alkoxy, nitro, amino, hydroxyl, cyano, -alk-$NH_2$, —$COOR_{10}$ and -alk-$COOR_{10}$ radicals, $R_5$ denotes a radical which is alkyl (1–11 C as straight or branched chain), -alk-Het, —$NR_8R_9$, —NH—CHO, —NH—$COOR_{17}$, —NH—$SO_2R_{24}$, —$COOR_{10}$, -alk-$COOR_{10}$, -alk-$CONR_{10}R_{18}$, -alk-$NR_{10}R_{18}$, -alk-OH, -alk-CN, phenylalkyl in which the phenyl nucleus is optionally substituted by one or more substituents chosen from halogen atoms and alkyl, alkoxy, nitro, amino, hydroxyl, cyano, -alk-$NH_2$, —$COOR_{10}$ and -alk-$COOR_{10}$ radicals, —NH—CO—Ar in which Ar is optionally substituted by one or more substituents chosen from halogen atoms and alkyl, alkoxy, nitro, amino, hydroxyl, cyano, -alk-$NH_2$, —$COOR_{10}$ and -alk-$COOR_{10}$ radicals, —NH—CO—Het, —NH—CO-alk-Het, —NH—CO-alk-$COOR_{10}$, —NH—CO-alk-$NR_{10}R_{18}$, —NH—CO-alk-Ar in which Ar is optionally substituted by one or more substituents chosen from halogen atoms and alkyl, alkoxy, nitro, amino, hydroxyl, cyano, -alk-$NH_2$, —$COOR_{10}$ and -alk-$COOR_{10}$ radicals, 1-pyrrolyl optionally substituted by a —$COOR_{10}$ radical, —NH—CO—NH-alk-Ar in which Ar is optionally substituted by one or more substituents chosen from halogen atoms and alkyl, alkoxy, nitro, amino, hydroxyl, cyano, -alk-$NH_2$, —$COOR_{10}$ and -alk-$COOR_{10}$ radicals, —NH—CO—NH—Het, —NH—CO—NH-alk-Het, —NH—CO—NH—Ar in which Ar is optionally substituted by one or more substituents chosen from halogen atoms and alkyl, alkoxy, nitro, amino, hydroxyl, cyano, -alk-$NH_2$, —$COOR_{10}$ and -alk-$COOR_{10}$ radicals, —NH—COalk, —NH—COcycloalkyl, —NH—CO—NH-alk or —NH—CO—$NH_2$, or else $R_4$ and $R_5$ form, together with the carbon atom to which they are attached, a cycloalkyl radical, $R_6$ denotes a hydrogen atom or a radical which is hydroxyl, alkyl (1–11 C as straight or branched chain), -alk-OH, —$NR_{14}R_{15}$, -alk-$NR_{14}R_{15}$, -alk-Het, —NH—CHO, —COOalk, -alk-$COOR_{10}$, -alk-CO—$NR_{10}R_{21}$, phenylalkyl in which the phenyl nucleus is optionally substituted by one or more substituents chosen from halogen atoms and alkyl, alkoxy, nitro, amino, hydroxyl, cyano, -alk-$NH_2$, —$COOR_{10}$ and -alk-$COOR_{10}$, —$R_{16}$—$COOR_{10}$, —CO—$COOR_{10}$ radicals, 1-pyrrolyl optionally substituted by a —$COOR_{10}$ or 2-oxo-2,5-dihydropyrrol-1-yl radical, $R_7$ denotes an oxygen atom or an NOH, NO-alk-$COOR_{10}$, NO-alk, $CHR_{19}$, $NR_{10}$, $C(COOR_{10})R_{20}$ or $C(CONR_{10}R_{21})R_{20}$ radical, $R_8$ denotes a hydrogen atom or an alkyl, -alk-$COOR_{10}$, -alk-$NR_{10}R_{21}$, -alk-Het or phenylalkyl radical in which the phenyl nucleus is optionally substituted by one or more substituents chosen from halogen atoms and alkyl, alkoxy, nitro, amino, hydroxyl, cyano, -alk-$NH_2$, —$COOR_{10}$ and -alk-$COOR_{10}$ radicals, $R_9$ denotes a hydrogen atom or an alkyl radical, $R_{10}$ denotes a hydrogen atom or an alkyl radical, $R_{11}$ denotes a hydrogen atom or a radical which is alkyl (1–9 C as straight or branched chain), -alk-$COOR_{10}$, -alk-Het, -alk-$NR_{12}R_{10}$ or phenylalkyl in which the phenyl nucleus is optionally substituted by one or more substituents chosen from halogen atoms and alkyl, alkoxy, nitro, amino, hydroxyl, -alk-$NH_2$, carboxyl, alkoxycarbonyl, cyano and -alk-$COOR_{10}$ radicals, phenyl optionally substituted by one or more substituents chosen from halogen atoms and alkyl, alkoxy, nitro, amino, hydroxyl, -alk-$NH_2$, carboxyl, alkoxycarbonyl, cyano and -alk-$COOR_{10}$ radicals or —Het, $R_{12}$ denotes a hydrogen atom or an alkyl radical, $R_{13}$ denotes an alkyl, Het or alkoxycarbonyl radical, each of $R_{14}$ and $R_{15}$, which are identical or different, denotes an alkyl radical or else $R_{14}$ denotes a hydrogen atom and $R_{15}$ denotes a hydrogen atom or an alkyl, —$COR_{22}$, —$CSR_{23}$ or —$SO_2R_{24}$ radical, $R_{16}$ denotes a —CHOH— or —CH(OH)—(1–5 C)alk-chain, $R_{17}$ denotes an alkyl or phenylalkyl radical, $R_{18}$ denotes a hydrogen atom or an alkyl radical, $R_{19}$ denotes a hydroxyl, alkyl, -alk-Het, —$NR_{25}R_{26}$, -alk-$COOR_{10}$, —Het or phenyl radical optionally substituted by one or more substituents chosen from halogen atoms and alkyl, alkoxy, nitro, amino, hydroxyl, -alk-$NH_2$, —$COOR_{10}$, cyano and -alk-$COOR_{10}$ radicals or phenylalkyl in which the phenyl nucleus is optionally substituted by one or more substituents chosen from halogen atoms and alkyl, alkoxy, nitro, amino, hydroxyl, -alk-$NH_2$, —$COOR_{10}$, cyano and -alk-$COOR_{10}$ radicals, $R_{20}$ denotes a hydrogen atom or an alkyl radical, $R_{21}$ denotes a hydrogen atom or an alkyl radical, $R_{22}$ denotes an alkyl, cycloalkyl, —COOalk, -alk-COOR$_{10}$ or phenyl radical optionally substituted by one or more substituents chosen from halogen atoms and alkyl, alkoxy, nitro, amino, hydroxyl, -alk-NH$_2$, —COOR$_{10}$, cyano and -alk-COOR$_{10}$ radicals, phenylalkyl in which the phenyl nucleus is optionally substituted by one or more substituents chosen from halogen atoms and alkyl, alkoxy, nitro, amino, hydroxyl, -alk-NH$_2$, —COOR$_{10}$, cyano and -alk-COOR$_{10}$ radicals, -alk-NR$_{10}$R$_{12}$, —NH—Ar in which Ar is optionally substituted by one or more substituents chosen from halogen atoms and alkyl, alkoxy, nitro, amino, hydroxyl, -alk-NH$_2$, —COOR$_{10}$, cyano and -alk-COOR$_{10}$ radicals, —Het, -alk-Het, —OR$_{17}$, —NH-alk-Ar in which Ar is optionally substituted by one or more substituents chosen from halogen atoms and alkyl, alkoxy, nitro, amino, hydroxyl, -alk-NH$_2$, —COOR$_{10}$, cyano and -alk-COOR$_{10}$ radicals, —NH-alk-Het, —NH-alk, —NH$_2$ or —NH—Het, $R_{23}$ denotes an —NH-alk, —NH—Ar, —NH—Het or —NH$_2$ radical, $R_{24}$ denotes an alkyl or phenyl radical, each of $R_{25}$ and $R_{26}$, which are identical or different, denotes an alkyl or cycloalkyl radical, $R_{27}$ denotes a hydrogen atom or an alkyl radical, alk denotes an alkyl or an alkylene radical, alk' denotes an alkyl radical, m is equal to 0, 1 or 2, Ar denotes a phenyl radical, Het denotes a saturated or unsaturated mono- or polycyclic heterocyclic ring containing 1 to 9 carbon atoms and one or more heteroatoms (O, S, N), which is optionally substituted by one or more alkyl, phenyl or phenylalkyl radicals.

Unless mentioned otherwise, in the definitions which precede and those which follow, the alkyl, alkylene and alkoxy radicals and moieties contain 1 to 6 carbon atoms and form a straight or branched chain, the acyl radicals and moieties contain 2 to 4 carbon atoms, the cycloalkyl radicals contain 3 to 6 carbon atoms and the halogen atoms are chosen from fluorine, chlorine, bromine and iodine.

Het is preferably chosen from rings which are pyrrolyl optionally substituted by one or more alkyl, phenyl or phenylalkyl radicals, pyridyl optionally substituted by one or more alkyl, phenyl or phenylalkyl radicals, pyrimidinyl optionally substituted by one or more alkyl, phenyl or phenylalkyl radicals, imidazolyl optionally substituted by one or more alkyl, phenyl or phenylalkyl radicals, thiazolyl optionally substituted by one or more alkyl, phenyl or phenylalkyl radicals, oxazolinyl optionally substituted by one or more alkyl, phenyl or phenylalkyl radicals, thiazolinyl optionally substituted by one or more alkyl, phenyl or phenylalkyl radicals, pyrazinyl optionally substituted by one or more alkyl, phenyl or phenylalkyl radicals, tetrazolyl optionally substituted by one or more alkyl, phenyl or phenylalkyl radicals or triazolyl optionally substituted by one or more alkyl, phenyl or phenylalkyl radicals. The preferred substituents are methyl, phenyl and benzyl radicals.

The compounds of formula (I) in which $R_7$ denotes an NO-alk, C(COOR$_{10}$)R$_{20}$, C(CONR$_{10}$R$_{21}$)R$_{20}$ or CHR$_{19}$ radical exhibit isomeric (E and Z) forms. These isomers and their mixtures form part of the invention.

The compounds of formula (I) in which R denotes a CH—R$_6$ radical and R$_6$ denotes a —CO—COOR$_{10}$ radical exhibit tautomeric (E and Z) forms. These tautomeric forms also form part of the invention.

The enantiomers and diastereoisomers of the compounds of formula (I) in which R denotes a C(R$_4$)R$_5$ or CH—R$_6$ radical also form part of the invention.

The compounds of formula (I) in which R denotes an N-alk or CH—R$_6$ radical, R$_6$ denotes a hydrogen atom and R$_3$ denotes an alkoxycarbonyl radical with the exception of tert-butoxycarbonyl can be prepared by cyclization, in the presence of ammonium acetate, of a derivative of formula:

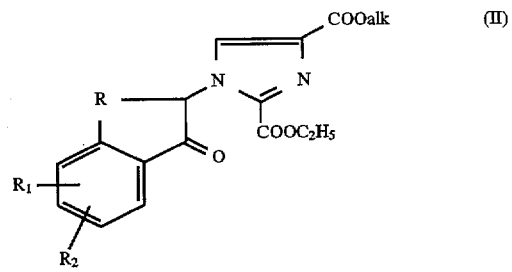

in which R denotes an N-alk or CH—R$_6$ radical, R$_6$ denotes a hydrogen atom, R$_1$ and R$_2$ have the same meanings as in formula (I) and —COOalk denotes an alkoxycarbonyl radical except tert-butoxycarbonyl.

This cyclization is generally performed in acetic acid at the boiling temperature of the reaction mixture.

The derivatives of formula (II) can be obtained by the action of an ethyl 4-alkoxycarbonylimidazole-2-carboxylate on a derivative of formula:

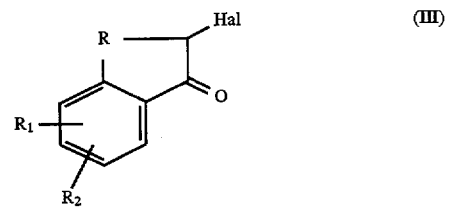

in which R denotes an N-alk or CH—R$_6$ radical, R$_6$ denotes a hydrogen atom, R$_1$ and R$_2$ have the same meanings as in formula (I) and Hal denotes a halogen atom.

This reaction is generally performed in an inert solvent such as a lower aliphatic alcohol (for example methanol or ethanol), a ketone (for example acetone or methyl ethyl ketone), an aromatic hydrocarbon (for example toluene), dimethylformamide or in the absence of solvent, optionally in the presence of a base such as sodium hydride or potassium carbonate, at a temperature of between 20° C. and the boiling temperature of the reaction mixture or the melting of the reaction mixture.

Ethyl 4-alkoxycarbonylimidazole-2-carboxylates can be obtained by application or adaptation of the method described by P. S. Branco et al., Tetrahedron, 48 (30), 6335 (1992).

Derivatives of formula (III) in which R denotes a CH—R$_6$ radical and R$_6$ denotes a hydrogen atom can be obtained by application or adaptation of the method described by M. Olivier et al., Bull. Soc. Chim. France, 3092 (1973).

Derivatives of formula (III) in which R denotes an N-alk radical can be obtained by alkylation of a corresponding derivative of formula (III) in which R denotes an NH radical, the latter being obtained by hydrolysis of the corresponding acetyl derivative prepared according to the method described by V. S. Velezheva et al., Khim. Farm. Zh., 24 (12), 46 (1990). The alkylation is generally performed by means of an alkyl halide, in the presence of an organic base such as triethylamine, an alkali metal hydroxide (for example sodium hydroxide or potassium hydroxide), optionally in the presence of tetrabutylammonium bromide, in an inert solvent such as dimethyl sulphoxide, dimethylformamide or pyridine, at a temperature of between 20° and 50° C. The hydrolysis is performed in an inert solvent such as dimethylformamide, water or a mixture of these solvents, at a temperature of between 5° C. and the boiling temperature of the reaction mixture.

Compounds of formula (I) in which R denotes an N-alk or CH—$R_6$ radical, $R_6$ denotes a hydrogen atom and $R_3$ denotes a tert-butoxycarbonyl radical can be prepared by the action of isobutene on a corresponding compound of formula (I) in which R denotes an N-alk or CH—$R_6$ radical, $R_6$ denotes a hydrogen atom and $R_3$ denotes a carboxyl radical.

This reaction is generally performed in an inert solvent such as dichloromethane or dioxane, in the presence of concentrated sulphuric acid, at a temperature of between 20° C. and the boiling temperature of the reaction mixture.

Compounds of formula (I) in which R denotes an N-alk or CH—$R_6$ radical, $R_6$ denotes a hydrogen atom and $R_3$ denotes a carboxyl radical can be prepared by cyclization, in the presence of ammonium acetate, of a derivative of formula (II) in which R denotes an N-alk or CH—$R_6$ radical, $R_6$ denotes a hydrogen atom and COOalk denotes a tert-butoxycarbonyl radical.

This cyclization is generally performed in acetic acid at the boiling temperature of the reaction mixture.

Compounds of formula (I) in which R denotes an N-alk or CH—$R_6$ radical, $R_6$ denotes a hydrogen atom and $R_3$ denotes a carboxamido radical can be prepared by cyclization of a derivative of formula:

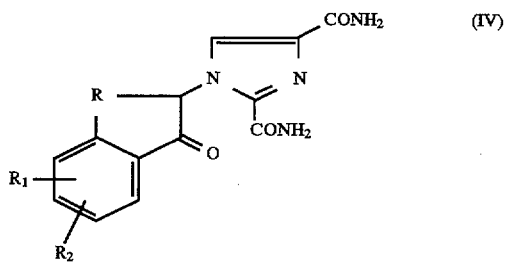

in which R denotes an N-alk or CH—$R_6$ radical, $R_6$ denotes a hydrogen atom and $R_1$ and $R_2$ have the same meanings as in formula (I).

This cyclization is generally performed by means of an acid such as hydrochloric acid or acetic acid, in aqueous solution, at a temperature of between 20° C. and the boiling temperature of the reaction mixture.

The derivatives of formula (IV) can be obtained by the action of ammonia on a corresponding derivative of formula (II).

This reaction is generally performed in an inert solvent such as a lower aliphatic alcohol, at a temperature of between 20° C. and the boiling temperature of the reaction mixture.

Compounds of formula (I) in which R denotes a C=$R_7$ radical in which $R_7$ denotes an oxygen atom can be prepared by hydrolysis of a corresponding compound of formula (I) in which R denotes a C=$R_7$ radical and $R_7$ denotes an NOH radical followed, in the case of the compounds in which $R_3$ denotes an alkoxycarbonyl radical, by an esterification of the corresponding acid.

This reaction is generally performed by means of an acid, in aqueous medium, at the boiling temperature of the reaction mixture. Hydrochloric acid is preferably employed as acid. The esterification is performed by means of an aliphatic alcohol ($C_1$–$C_6$ as straight or branched chain), in acidic medium (for example hydrochloric or sulphuric acid), at the boiling temperature of the reaction mixture.

Compounds of formula (I) in which R denotes a C=$R_7$ radical and $R_7$ denotes an NOH radical can be prepared by the action of an alkyl nitrite on a corresponding compound of formula (I) in which R denotes a CH—$R_6$ radical and $R_6$ denotes a hydrogen atom.

This reaction is preferably performed in an inert solvent such as dimethyl sulphoxide, in the presence of an alkali metal hydride such as sodium hydride, at a temperature close to 20° C. Isoamyl nitrite is preferably employed.

Compounds of formula (I) in which R denotes a C=$R_7$ radical and $R_7$ denotes an NO-alk-$COOR_{10}$ or NO-alk radical can be prepared by the action of a corresponding compound of formula (I) in which R denotes a C=$R_7$ radical and $R_7$ denotes an NOH radical on a halide Hal-Ra in which Hal denotes a halogen atom and Ra denotes an alkyl or -alk-$COOR_{10}$ radical, alk and $R_{10}$ having the same meanings as in formula (I).

This reaction is preferably performed in the presence of a base such as an alkali metal hydride like sodium hydride, in an inert solvent such as dimethyl sulphoxide, at a temperature close to 20° C.

The Hal-Ra derivatives in which Ra denotes an -alk-$COOR_{10}$ radical are marketed or can be obtained by the action of Hal-alk-Hal in which Hal denotes a halogen atom and alk denotes an alkyl radical on an alkali metal cyanide (sodium or potassium cyanide) in a mixture of water and lower aliphatic alcohol, at a temperature of between 0° C. and the boiling temperature of the reaction mixture, followed by the action of a strong acid such as hydrochloric acid, in the presence of a lower aliphatic alcohol (for example methanol or ethanol), at a temperature of between 0° C. and the boiling temperature of the reaction mixture.

Compounds of formula (I) in which R denotes a C=$R_7$ radical and $R_7$ denotes a CH—$R_{19}$ radical in which $R_{19}$ denotes a hydroxyl radical can be prepared by hydrolysis of a corresponding compound of formula (I) in which $R_{19}$ denotes an —$NR_{25}R_{26}$ radical, followed, in the case of compounds in which $R_3$ denotes an alkoxycarbonyl radical, by an esterification of the corresponding acid.

This reaction is preferably performed by means of an acid such as hydrochloric acid, in aqueous medium, at a temperature of between 20° and 40° C. The esterification is performed by means of an aliphatic alcohol ($C_1$–$C_6$ as straight or branched chain), in acidic medium (for example hydrochloric or sulphuric acid), at the boiling temperature of the reaction mixture.

Compounds of formula (I) in which R denotes a C=$R_7$ radical and $R_7$ denotes a CH—$R_{19}$ radical in which $R_{19}$ denotes an —$NR_{25}R_{26}$ radical can be prepared by the action of a corresponding compound of formula (I) in which R denotes a —CH—$R_6$ radical and $R_6$ denotes a hydrogen atom on a derivative HC(Rb)(Rc)Rd in which either each of Rb and Rd, which are identical or different, denotes an —$NR_{25}R_{26}$ radical in which $R_{25}$ and $R_{26}$ have the same meanings as in formula (I) and Rc denotes an alkoxy radical such as tert-butoxy, or each of Rb, Rc and Rd, which are identical, denotes an —$NR_{25}R_{26}$ radical in which $R_{25}$ and $R_{26}$ have the same meanings as in the formula (I).

This reaction is generally performed in an inert solvent such as dimethylformamide, at a temperature of between 20° and 40° C.

The derivatives HC(Rb)(Rc)Rd can be obtained by application or adaptation of the method described by H. Bredereck, Liebigs Ann. Chem., 762, 62 (1972).

Compounds of formula (I) in which R denotes a C=$R_7$ radical, $R_7$ denotes a CH$R_{19}$ radical and $R_{19}$ denotes a radical which is alkyl, optionally substituted phenyl, -alk-Het or phenylalkyl radical in which the phenyl nucleus is optionally substituted, —Het or -alk-COO$R_{10}$ can be prepared by the action of a corresponding compound of formula (I) in which R denotes a CH—$R_6$ radical and $R_6$ denotes a hydrogen atom on an aldehyde of formula OHC—Re in which Re denotes a radical which is alkyl or phenyl optionally substituted by one or more substituents chosen from halogen atoms and alkyl, alkoxy, nitro, amino, hydroxyl, -alk-NH$_2$, —COO$R_{10}$, cyano and -alk-COO$R_{10}$ radicals, -alk-Het, phenylalkyl in which the phenyl nucleus is optionally substituted by one or more substituents chosen from halogen atoms and alkyl, alkoxy, nitro, amino, hydroxyl, -alk-NH$_2$, —COO$R_{10}$, cyano and -alk-COO$R_{10}$ radicals, —Het or -alk-COO$R_{10}$ in which alk, Het and $R_{10}$ have the same meanings as in formula (I).

This reaction is generally performed either in an inert solvent such as dimethylformamide, 1,2-dimethoxyethane, a lower aliphatic alcohol (for example methanol or ethanol) or a mixture of these solvents, in the presence of a base such as sodium hydroxide or potassium hydroxide, a strong organic base such as 1,8-diazabicyclo[5.4.0]undec-7-ene, at a temperature of between 20° and 100° C., or in dimethyl sulphoxide, in the presence of an alkali metal hydride such as sodium hydride, at a temperature close to 20° C., or in the presence of tetrabutylammonium bromide and of a base such as an alkali metal hydroxide (for example sodium hydroxide or potassium hydroxide), in dimethyl sulphoxide, at a temperature of between 20° C. and the boiling temperature of the reaction mixture.

The derivatives OHC-Re are marketed or can be obtained (a) by oxidation of the corresponding alcohols (with the aid of K$_2$Cr$_2$O$_7$ in sulphuric medium; of CrO$_3$ in pyridine or of MnO$_2$ in a chlorinated solvent (for example dichloromethane), at a temperature close to 20° C. or with the aid of dimethyl sulphoxide and of ClCO—COCl by adaptation or application of the method described by D. Swern et al., J. Org. Chem., 44, 4148 (1979)); (b) by reduction of the corresponding carboxylic acids (with the aid of lithium aluminium hydride or of AlH$_3$, in an inert solvent such as tetrahydrofuran, at a temperature of between 0° and 25° C.); (c) by reduction of the corresponding esters (with the aid of diisobutylaluminium hydride, in an inert solvent such as toluene, at a temperature of between −70° C. and 25° C. or of lithium aluminium hydride, in an inert solvent such as tetrahydrofuran, at a temperature of between 0° and 25° C.).

The corresponding alcohols HOH$_2$C-alk-Het or HOH$_2$C-alk-Ar in which Ar is optionally substituted are marketed or can be obtained from the corresponding organometallic compounds by application or adaptation of the methods described by N. S. Narasimham et al., Tetrahedron Lett.,. 22 (29), 2797 (1981); L. Estel et al., J. Het. Chem., 26, 105 (1089); N. S. Narasimham et al., Synthesis, 957 (1983); H. W. Gschwend et al., Organic Reactions, 26, I (1979); V. Snieckus, Chem. Rev., 90, 879 (1990) and F. Marsais et al., J. Heterocyclic Chem., 25, 81 (1988). The organolithium or organomagnesium derivative of the heterocyclic compound or of optionally substituted benzene is preferably reacted with formalin, ethylene oxide or a derivative Hal-alk-CH$_2$OP where P is a protecting group (for example methyl ether, tetrahydropyranyl ether, benzyl ether or triethylsilyl ether), Hal denotes a halogen and alk denotes an alkyl, and the alcohol functional group is then liberated by application or adaptation of the methods described by W. Greene et al., Protecting Groups in Organic Synthesis, second edition, 1991, John Wiley and Sons.

The corresponding alcohols HOH$_2$C-alk-Het or HOH$_2$C-alk-Ar in which Ar is optionally substituted can also be obtained by reduction of the corresponding carboxylic acids or esters by means of lithium aluminium hydride, in an inert solvent such as tetrahydrofuran or diethyl ether, at the boiling temperature of the reaction mixture.

The alcohols HOH$_2$C-alk-Het can also be obtained by application or adaptation of the method described by J. Th. Meyer et al., Helv. Chem. Acta, 65, 1868 (1982) from the derivatives Hal-(0–5 C)alk-Het in which Hal denotes a halogen, alk denotes an alkyl and Het has the same meanings as in formula (I) which themselves are obtained by the action of a halogenating agent (halogen derivative of phosphorus or thionyl chloride) with a corresponding derivative HOH$_2$C—(0–5 C)alk-Het, optionally in an inert solvent such as dichloromethane, at a temperature of between 20° and 40° C.

The corresponding carboxylic acids HOOC—Het, HOOC-alk-Het and HOOC-alk-Ar in which Ar is optionally substituted are marketed or can be obtained from the corresponding heterocyclic compounds or optionally substituted benzene by application or adaptation of the methods described by L. Estel et al., J. Heterocyclic Chem., 26, 105 (1989); N. S. Narasimhan et al., Synthesis, 957 (1983); A. Turck et al., Synthesis, 881 (1988); A. J. Clarke et al., Tetrahedron Lett., 27, 2373 (1974); A. R. Katritzky et al., Org. Prep. Procedure Int., 20 (6), 585 (1988); N. Furukawa et al., Tetrahedron Lett., 28 (47), 5845 (1987); H. W. Gschwend et al., Organic Reactions, 26, 1 (1979) and V. Snieckus, Chem. Rev., 90, 879 (1990). Preferably, the corresponding organometallic (for example organolithium or organomagnesium) derivative of the corresponding heterocyclic compound or optionally substituted benzene is prepared and is reacted either with CO$_2$ or with a derivative Hal-alk-COOalk in which Hal denotes a halogen atom and alk an alkyl radical. The corresponding esters are marketed or can be obtained from acids by the action of an acid such as hydrochloric acid or sulphuric acid, in the alcohol also serving as esterifying agent, at the boiling temperature of the reaction mixture. The derivatives Hal-alk-COOalk are marketed or prepared by the action of Hal-alk-Hal in which Hal denotes a halogen atom and alk is an alkyl on an alkali metal cyanide such as sodium or potassium cyanide in a mixture of water and lower aliphatic alcohol, at a temperature of between 0° C. and the boiling temperature of the reaction mixture, followed by the action of an acid such as hydrochloric acid, in the presence of a lower aliphatic alcohol, at a temperature of between 0° C. and the boiling temperature of the reaction mixture.

The derivatives HOC—Re in which Re denotes an -alk-COO$R_{10}$ radical are marketed or can be obtained by reduction of the corresponding carboxylic acids by application or adaptation of the methods described by H. C. Brown et al., J. Am. Chem. Soc., 106, 8001 (1984) and J. Org. Chem., 52, 5400 (1987). The corresponding acids are marketed or can be obtained by application or adaptation of the methods described by H. Hunsdiecker et al., Chem. Ber., 75, 256 (1942) and R. F. Naylor, J. Chem. Soc., 1108 (1947).

Compounds of formula (I) in which R denotes a C=$R_7$ radical and $R_7$ denotes an NR$_{10}$ radical can be prepared by the action of ethyl trifluoroacetate on a derivative of formula:

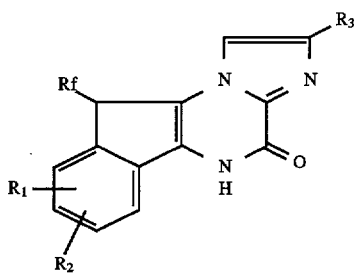

(V)

in which $R_1$, $R_2$ and $R_3$ have the same meanings as in formula (I) and Rf denotes an —$NH_2$ or —NH-alk radical, alk having the same meanings as in formula (I).

This reaction is generally performed in an inert solvent such as dimethylformamide, at a temperature close to 60° C.

The derivatives of formula (V) in which Rf denotes an —$NH_2$ or —NH-alk radical can be obtained by analogy with the processes described below for the preparation of compounds of formula (I) in which R denotes a CH—$R_6$ radical and $R_6$ denotes an —$NR_{14}R_{15}$ radical.

Compounds of formula (I) in which R denotes a C=$R_7$ radical and $R_7$ denotes a C(COOR$_{10}$)$R_{20}$ radical can be prepared by dehydration of a compound of formula (V) in which $R_1$, $R_2$ and $R_3$ have the same meanings as in formula (I) and Rf denotes a —C($R_{20}$)(OH)—COOR$_{10}$ radical in which $R_{20}$ and $R_{10}$ have the same meanings as in formula (I).

This reaction is generally performed in acetic anhydride, at the boiling temperature of the reaction mixture.

Compounds of formula (V) in which $R_1$, $R_2$ and $R_3$ have the same meanings as in the formula (I) and Rf denotes a —C($R_{20}$)(OH)—COOR$_{10}$ radical in which $R_{20}$ and $R_{10}$ have the same meanings as in formula (I) can be obtained by the action of a corresponding compound of formula (I) in which R denotes a CH—$R_6$ radical and $R_6$ denotes a hydrogen atom on a derivative $R_{20}$—CO—COOR$_{10}$ in which $R_{10}$ and $R_{20}$ have the same meanings as in the formula (I), followed by a treatment with acetic acid.

This reaction is performed in dimethyl sulphoxide, in the presence of an alkali metal hydride such as sodium hydride, at a temperature close to 20° C. or in the presence of tetrabutylammonium bromide and of a base such as an alkali metal hydroxide (for example sodium hydroxide or potassium hydroxide), in dimethyl sulphoxide, at a temperature of between 20° and 100° C. The treatment with acetic acid is performed at a temperature below 20° C.

The derivatives of formula $R_{20}$—CO—COOR$_{10}$ in which $R_{10}$ and $R_{20}$ have the same meanings as in formula (I) are marketed or can be obtained by application or adaptation of the methods described by L. A. Carpino, J. Org. Chem., 29, 2820 (1964) and H. H. Wasserman, J. Org. Chem. 50, 3573 (1985).

Compounds of formula (I) in which R denotes a C=$R_7$ radical and $R_7$ denotes a C(CONR$_{10}$R$_{21}$)$R_{20}$ radical can be prepared by the action of a corresponding compound of formula (I) in which R denotes a C=$R_7$ radical and $R_7$ denotes a C(COOR$_{10}$)$R_{20}$ on an amine HNR$_{10}$R$_{21}$ in which $R_{10}$ and $R_{21}$ have the same meanings as in formula (I).

When the acid is used, the operation is carried out in the presence of a condensing agent employed in peptide chemistry, such as a carbodiimide (for example N,N'-dicyclohexylcarbodiimide) or N,N'-diimidazolecarbonyl, in an inert solvent such as an ether (for example tetrahydrofuran or dioxane), an amide (dimethylformamide) or a chlorinated solvent (for example methylene chloride, 1,2-dichloroethane or chloroform) at a temperature of between 0° C. and the reflux temperature of the reaction mixture.

When an ester is used, the operation is then carried out either in organic medium, optionally in the presence of an acid-acceptor such as a nitrogenous organic base (for example trialkylamine, pyridine, 1,8-diazabicyclo[5.4.0]undec-7-ene or 1,5-diazabicyclo[4.3.0]-non-5-ene), in a solvent such as mentioned above, or a mixture of these solvents, at a temperature of between 0° C. and the reflux temperature of the reaction mixture, or in a two-phase hydroorganic mixture in the presence of an alkaline or alkaline-earth base (sodium hydroxide, potassium hydroxide) or of an alkali or alkaline-earth metal carbonate or bicarbonate at a temperature of between 0° and 40° C.

Compounds of formula (I) in which R denotes a C($R_4$)$R_5$ radical, $R_4$ denotes an alkyl, -alk-Het or phenylalkyl radical in which the phenyl nucleus is optionally substituted by one or more substituents chosen from halogen atoms and alkyl, alkoxy, nitro, amino, hydroxyl, cyano, -alk-$NH_2$, —COOR$_{10}$ and -alk-COOR$_{10}$ radicals and $R_5$ is identical with $R_4$ can be prepared by the action of a corresponding compound of formula (I) in which R denotes a CH—$R_6$ radical and $R_6$ denotes a hydrogen atom on a halide of formula Hal-Rg in which Rg denotes an alkyl, -alk-het or phenylalkyl radical in which the phenyl nucleus is optionally substituted by one or more substituents chosen from halogen atoms and alkyl, alkoxy, nitro, amino, hydroxyl, cyano, -alk-$NH_2$, —COOR$_{10}$ and -alk-COOR$_{10}$ radicals, alk, Het and $R_{10}$ having the same meanings as in formula (I).

This reaction is preferably performed in an inert solvent such as dimethyl sulphoxide, dimethylformamide, tetrahydrofuran or dioxane, in the presence of a base such as an alkali metal hydroxide (for example sodium hydroxide or potassium hydroxide), optionally in the presence of tetrabutylammonium bromide, or in dimethyl sulphoxide or dimethylformamide in the presence of an alkali metal hydride (for example sodium hydride), at a temperature of between 20° C. and the boiling temperature of the reaction mixture.

The derivatives Hal-Reg are marketed or can be obtained from the corresponding alcohols by application or adaptation of the methods described by R. C. Larock, "Comprehensive Organic Transformations", VCH Publ., page 353 (1989).

Compounds of formula (I) in which R denotes a C($R_4$)$R_5$ radical, $R_4$ denotes an alkyl, -al-Het or phenylalkyl radical in which the phenyl nucleus is optionally substituted by one or more substituents chosen from halogen atoms and alkyl, alkoxy, nitro, amino, hydroxyl, cyano, -alk-$NH_2$, —COOR$_{10}$ and -alk-COOR$_{10}$ radicals and $R_5$ denotes an alkyl (1–11 C as straight or branched chain), -alk-CN, -alk-Het, -alk-NR$_{10}$R$_{18}$, -alk-CO—NR$_{10}$R$_{18}$ or phenylalkyl radical in which the phenyl nucleus is optionally substituted by one or more substituents chosen from halogen atoms and alkyl, alkoxy, nitro, amino, hydroxyl, cyano, -alk-$NH_2$, —COOR$_{10}$ and -alk-COOR$_{10}$ radicals can be prepared by the action of a corresponding compound of formula (I) in which R denotes a CH—$R_6$ radical and $R_6$ denotes an alkyl, -alk-Het or phenylalkyl radical in which the phenyl nucleus is optionally substituted by one or more substituents chosen from halogen atoms and alkyl, alkoxy, nitro, amino, hydroxyl, cyano, -alk-$NH_2$, —COOR$_{10}$ and -alk-COOR$_{10}$ radicals on a halide Hal-Rh in which Rh denotes an alkyl (1–11 C as straight or branched chain), alk-Het, -alk-CN, -alk-NR$_{10}$R$_{18}$, -alk-CO—NR$_{10}$R$_{18}$ or phenylalkyl radical in which the phenyl nucleus is optionally substituted by one or more substituents chosen from halogen atoms and alkyl, alkoxy, nitro, amino, hydroxyl, cyano, -alk-$NH_2$, —COOR$_{10}$ and -alk-COOR$_{10}$ radicals, alk, Het, $R_{10}$ and $R_{18}$ having the same meanings as in formula (I).

This reaction is preferably performed in an inert solvent such as dimethyl sulphoxide, dimethylformamide, tetrahydrofuran or dioxane, in the presence of a base such as an alkali metal hydroxide (for example sodium hydroxide or potassium hydroxide), optionally in the presence of tetrabutylammonium bromide, or in dimethyl sulphoxide or dimethylformamide in the presence of an alkali metal hydride (for example sodium hydride), at a temperature of between 20° C. and the boiling temperature of the reaction mixture.

The derivatives Hal-Rh are marketed or those in which Rh denotes an -alk-CO—$NR_{10}R_{18}$ radical can be prepared by the action of an amine $HNR_{10}R_{18}$ on a derivative Hal-alk-CO-Hal in which Hal denotes a halogen atom and alk denotes an alkyl radical, in an inert solvent such as dimethylformamide, tetrahydrofuran or a chlorinated solvent, in the presence of an organic base such as a trialkylamine or pyridine, at a temperature of between 0° C. and the boiling temperature of the reaction mixture. The derivatives Hal-alk-CO-Hal are marketed or can be obtained by halogenation of the corresponding carboxylic acids by means of a halogenating agent such as thionyl chloride, in an inert solvent such as 1,2-dichloroethane, at a temperature close to 60° C. The acids Hal-alk-COOH are marketed or can be obtained by the action of an alkali metal cyanide on a derivative Hal-alk-Hal in which alk denotes an alkyl radical and Hal denotes a halogen atom, in a mixture of water and lower aliphatic alcohol, at a temperature of between 0° C. and the boiling temperature of the reaction mixture, followed by the action of a strong acid such as hydrochloric acid, in aqueous medium, at a temperature of between 0° C. and the boiling temperature of the reaction mixture.

Compounds of formula (I) in which R denotes a $C(R_4)R_5$ radical and $R_4$ and $R_5$, together with the carbon atom to which they are attached, form a cycloalkyl radical can be prepared by the action of a corresponding compound of formula (I) in which R denotes a CH—$R_6$ radical and $R_6$ denotes a hydrogen atom on a derivative of formula Hal-alk-Hal in which Hal denotes a halogen atom and alk denotes an alkyl (2–5 C) radical.

This reaction is preferably performed in an inert solvent such as dimethyl sulphoxide, dimethylformamide, tetrahydrofuran, or dioxane, in the presence of a base such an alkali metal hydroxide (for example sodium hydroxide or potassium hydroxide), optionally in the presence of tetrabutylammonium bromide, or in dimethyl sulphoxide or dimethylformamide in the presence of an alkali metal hydride (for example sodium hydride), at a temperature of between 20° C. and the boiling temperature of the reaction mixture.

The derivatives Hal-alk-Hal are marketed or can be obtained from the corresponding dialcohols by application or adaptation of the methods described by C. Larock, "Comprehensive Organic Transformations", VHC Publ., page 353 (1989).

Compounds of formula (I) in which R denotes a $C(R_4)R_5$ radical in which $R_5$ denotes an —$NR_8R_9$ radical and $R_8$ and $R_9$ denote hydrogen atoms can be prepared by the action of a halide Hal-$R_4$ in which Hal denotes a halogen atom and $R_4$ has the same meanings as in formula (I), on a corresponding compound of formula (I) in which R denotes a CH—$R_6$ radical, $R_6$ denotes an —$NR_{14}R_{15}$ radical, $R_{14}$ denotes a hydrogen atom, $R_{15}$ denotes a —$COR_{22}$ radical and $R_{22}$ denotes an alkyl (1 C) radical, followed by a hydrolysis.

This reaction is generally performed in an inert solvent such as dimethyl sulphoxide, in the presence of an alkali metal hydride such as sodium hydride, at a temperature close to 20° C. The hydrolysis is generally performed by means of an inorganic acid such as hydrochloric acid, in aqueous medium, at the boiling temperature of the reaction mixture.

Compounds of formula (I) in which R denotes a $C(R_4)R_5$ radical in which $R_5$ denotes an —$NR_8R_9$ radical, $R_9$ denotes a hydrogen atom and $R_8$ denotes an alkyl, -alk-$COOR_{10}$, -alk-$NR_{10}R_{21}$, -alk-Het or phenylalkyl radical in which the phenyl nucleus is optionally substituted can be prepared by the action of a corresponding compound of formula (I) in which R denotes a $C(R_4)R_5$ radical, $R_5$ denotes an —$NR_8R_9$ radical and $R_8$ and $R_9$ denote hydrogen atoms on a halide Hal-$R_8$ in which $R_8$ has the same meanings as above.

This reaction is generally performed in an inert solvent such as dimethylformamide, in the presence of an alkali metal carbonate such as sodium or potassium carbonate or a trialkylamine such as triethylamine or pyridine, at a temperature of between 0° C. and the boiling temperature of the reaction mixture.

The halides Hal-$R_8$ are marketed or those in which $R_8$ denotes an -alk-$NR_{10}R_{21}$ radical can be obtained by the action of the amine $HNR_{10}R_{21}$ in which $R_{10}$ and $R_{21}$ have the same meanings as in formula (I) on a halide Hal-alk-Hal in which Hal denotes a halogen atom and alk denotes an alkyl radical, in an inert solvent such as dimethylformamide, in the presence of an acid-acceptor such as a nitrogenous base, at a temperature of between 0° and 25° C. Those in which $R_8$ denotes an -alk-$COOR_{10}$ radical can be obtained by the action of a derivative Hal-alk-Hal in which Hal denotes a halogen atom and alk denotes an alkyl radical on an alkali metal cyanide (sodium or potassium cyanide), in a mixture of water and lower aliphatic alcohol, at a temperature of between 0° C. and the boiling temperature of the reaction mixture, followed by the action of a strong acid such as HCl, in the presence of a lower aliphatic alcohol, at a temperature of between 0° C. and the boiling temperature of the reaction mixture.

Compounds of formula (I) in which R denotes a $C(R_4)R_5$ radical in which $R_5$ denotes an —$NR_8R_9$ radical, $R_9$ denotes a hydrogen atom or an alkyl radical and $R_8$ denotes an alkyl (2–6 C) radical can be prepared by the action of a corresponding compound of formula (I) in which R denotes a $C(R_4)R_5$ radical, $R_5$ denotes an —$NR_8R_9$ radical, $R_9$ denotes a hydrogen atom or an alkyl radical and $R_8$ denotes a hydrogen atom on an acyl (2–6 C) halide, and then reduction of the product obtained.

This reaction is generally performed in an inert solvent such as dimethylformamide, in the presence of an acid-acceptor such as a nitrogenous organic base (trialkylamine such as triethylamine or pyridine), at a temperature of between 0° C. and the boiling temperature of the reaction mixture. The reduction is performed in an inert solvent such as tetrahydrofuran, in the presence of $B_2H_6$, at the boiling temperature of the reaction mixture.

Compounds of formula (I) in which R denotes a $C(R_4)R_5$ radical in which $R_5$ denotes an —$NR_8R_9$ radical and $R_9$ denotes an alkyl radical can also be prepared by the action of a corresponding compound of formula (I) in which R denotes a $C(R_4)R_5$ radical, $R_5$ denotes an —$NR_8R_9$ radical, $R_8$ has the same meanings as in formula (I) and $R_9$ denotes a hydrogen atom on a derivative of formula Hal-alk in which Hal denotes a halogen atom and alk denotes an alkyl radical.

This reaction is performed in an inert solvent such as dimethylformamide, in the presence of an acid-acceptor such as a nitrogenous organic base (pyridine or trialkylamine like triethylamine), at a temperature of between 0° C. and the boiling temperature of the reaction mixture.

The derivatives Hal-$R_9$ can be obtained by application or adaptation of the methods described by C. Larock, "Comprehensive Organic Transformations", VCH Publ., pages 345 and 353 (1989).

Compounds of formula (I) in which R denotes a $C(R_4)R_5$ radical in which $R_5$ denotes an $—NR_8R_9$ radical, $R_9$ denotes a hydrogen atom or an alkyl radical and $R_8$ denotes a $—(2–6 C)alk-NR_{10}R_{21}$ radical can be prepared by reduction of a derivative of formula:

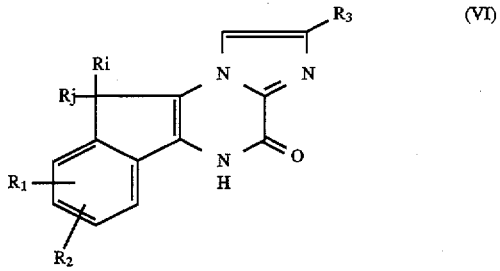

in which $R_1$, $R_2$ ad $R_3$ have the same meanings as in formula (I), Ri denotes an alkyl or phenylalkyl radical in which the phenyl nucleus is optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals or an -alk-Het radical and Rj denotes an —NH—CO-(1–5 C)alk-NR$_{10}$R$_{21}$ or —N(alk)-CO—(1–5 C)alk-NR$_{10}$R$_{21}$ radical in which alk, Het, R$_{10}$ and R$_{21}$ have the same meanings as in formula (I).

This reduction is performed in an inert solvent such as tetrahydrofuran, by means of $B_2H_6$, at the boiling temperature of the reaction mixture.

The derivatives of formula (VI) in which Ri denotes an alkyl or phenylalkyl radical in which the phenyl nucleus is optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals or an -alk-Het radical and Rj denotes an —NHCO—(1–5 C)alk-NR$_{10}$R$_{21}$ or —N(alk)-CO—(1–5 C)alk-NR$_{10}$R$_{21}$ radical in which R$_{10}$ and R$_{21}$ are hydrogen atoms can be obtained by the action of a corresponding compound of formula (I) in which R denotes a $C(R_4)R_5$ radical, R$_5$ denotes an —NR$_8$R$_9$ radical, R$_8$ denotes a hydrogen atom and R$_9$ denotes a hydrogen atom or an alkyl radical on a derivative of formula:

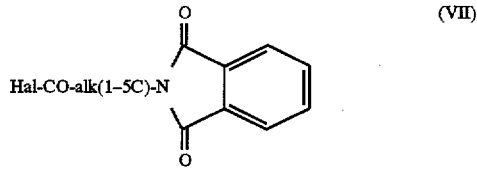

in which Hal denotes a halogen atom and alk denotes an alkyl radical, and then deprotection of the amino functional group.

This reaction is performed in an inert solvent such as dimethylformamide, in the presence of an acid-acceptor such as a nitrogenous organic base (pyridine or trialkylamine like triethylamine), at a temperature of between 0° C. and the boiling temperature of the reaction mixture. The deprotection is performed in a lower aliphatic alcohol (for example ethanol) in the presence of hydrazine, at the boiling temperature of the reaction mixture.

The derivatives of formula (VII) can be obtained by application or adaptation of the method described by K. Balenovic et al., J. Org. Chem., 17, 1459 (1952).

The derivatives of formula (VI) in which Ri denotes an alkyl or phenylalkyl radical in which the phenyl nucleus is optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals or an -alk-Het radical and Rj denotes an —NH—CO—(1–5 C)alk-NR$_{10}$R$_{21}$ or —N(alk)-CO—(1–5 C)alk-NR$_{10}$R$_{21}$ radical in which R$_{10}$ and R$_{21}$ have the same meanings as in formula (I) can also be obtained by the action of a corresponding compound of formula (I) in which R denotes a $C(R_4)R_5$ radical, $R_5$ denotes an —NR$_8$R$_9$ radical, R$_8$ denotes a hydrogen atom and R$_9$ denotes a hydrogen atom or an alkyl radical on a derivative of formula Hal-CO—(1–5 C)alk-NR$_{10}$R$_{21}$ in which alk denotes an alkyl radical, R$_{10}$ and R$_{21}$ have the same meanings as in formula (I) and Hal denotes a halogen atom and preferably a chlorine or bromine atom.

This reaction is performed in an inert solvent such as dimethylformamide in the presence of an acid-acceptor such as a nitrogenous organic base (pyridine or trialkylamine like triethylamine), at a temperature of between 0° C. and the boiling temperature of the reaction mixture.

The derivatives of formula Hal-CO—(1–5 C)alk-NR$_{10}$R$_{21}$ can be obtained by heating the corresponding carboxylic acid and a halogenating reactant such as thionyl chloride, in an inert solvent such as 1,2-dichloroethane, at a temperature close to 60° C. The corresponding acids are marketed or can be obtained by the action of the halides alkOOC—(1–5 C)alk-Hal in which Hal denotes a halogen atom and alk an alkyl radical, on an amine HNR$_{10}$R$_{21}$ in which R$_{10}$ and R$_{21}$ have the same meanings as in formula (I), in the presence of an alkali metal carbonate (sodium carbonate) or a trialkylamine, at a temperature of between 20° C. and the boiling temperature of the reaction mixture, followed by a hydrolysis in basic medium (sodium hydroxide-lower aliphatic alcohol), at a temperature of between 0° and 60° C. and by an acidification by means of an acid such as hydrochloric acid, at a temperature of between 20° and 60° C.

Compounds of formula (I) in which R denotes a $C(R_4)R_5$ radical in which $R_5$ denotes a —COOR$_{10}$ radical and R$_{10}$ denotes a hydrogen atom can be prepared by hydrolysis of a corresponding compound of formula (I) in which R denotes a $C(R_4)R_5$ radical in which $R_5$ denotes a —COOR$_{10}$ radical and R$_{10}$ denotes an alkyl radical.

This hydrolysis is preferably performed by means of a base such as an alkali metal hydroxide (for example sodium hydroxide or potassium hydroxide), in a mixture of water and lower aliphatic alcohol (for example ethanol), at a temperature of approximately 20° to 30° C.

Compounds of formula (I) in which R denotes a $C(R_4)R_5$ radical in which $R_5$ denotes a —COOR$_{10}$ radical and R$_{10}$ denotes an alkyl radical can be prepared by the action of a corresponding compound of formula (I) in which R denotes a CH—R$_6$ radical and R$_6$ denotes an alkyl, -alk-Het or optionally substituted phenylalkyl radical on a halide of formula Hal-COOR$_{10}$ in which R$_{10}$ denotes an alkyl radical and Hal denotes a halogen atom.

This reaction is generally performed in an inert solvent such as dioxane, in the presence of an alkali metal hydride such as sodium or potassium hydride, at a temperature close to 20° C.

The derivatives Hal-COOR$_{10}$ are marketed or can be obtained by application or adaptation of the methods described in Houben-Weyl, volume 8, page 102 (1952).

Compounds of formula (I) in which R denotes a $C(R_4)R_5$ radical in which $R_5$ denotes an -alk-COOR$_{10}$ radical can be prepared by the action of a corresponding compound of formula (I) in which R denotes a CH—R$_6$ radical, R$_6$ denotes an -alk-COOR$_{10}$ radical and R$_{10}$ has the same meanings as in formula (I) on a halide Hal-R$_4$ in which R$_4$ has the same meanings as in formula (I).

This reaction is performed in an inert solvent such as dimethylformamide, in the presence of an alkali metal hydride such as sodium or potassium hydride, at a temperature close to 20° C.

Compounds of formula (I) in which R denotes a C(R$_4$)R$_5$ radical in which R$_5$ denotes an -alk-CN radical in which alk contains 1 carbon atom can be prepared by the action of sodium cyanide on a derivative of formula (VI) in which R$_1$, R$_2$ and R$_3$ have the same meanings as in formula (I), Ri denotes a —CH$_2$OTs radical in which Ts denotes a tosylate residue and Rj denotes an alkyl, -alk-Het or phenylalkyl radical in which the phenyl nucleus is optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals, alk, Het and R$_{10}$ having the same meanings as in formula (I).

This reaction is preferably performed in dimethylformamide, in the presence of sodium iodide, at a temperature of between 20° and 100° C.

The derivatives of formula (VI) in which R$_1$, R$_2$ and R$_3$ have the same meanings as in formula (I), Ri denotes a —CH$_2$OTs radical in which Ts denotes a tosylate residue and Rj denotes an alkyl, -alk-Het or phenylalkyl radical in which the phenyl nucleus is optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals can be obtained by the action of tosyl chloride on a corresponding compound of formula (I) in which R$_5$ denotes a —(1 C)alkOH radical in pyridine, at a temperature of between −10° and 20° C.

Compounds of formula (I) in which R denotes a C(R$_4$)R$_5$ radical in which R$_5$ denotes a —(2–6 C)alkOH radical can be prepared by the action of (COCl)$_2$ on a corresponding compound of formula (I) in which R denotes a C(R$_4$)R$_5$ radical in which R$_5$ denotes an -alk-COOR$_{10}$ radical and R$_{10}$ denotes a hydrogen atom, followed by a reduction.

This reaction is performed in an inert solvent such as dioxane. The reduction is preferably performed by means of sodium borohydride, in an inert solvent such as dimethylformamide, at a temperature of between 10° and 20° C.

Compounds of formula (I) in which R denotes a C(R$_4$)R$_5$ radical in which R$_5$ denotes a —(1 C)alkOH radical can be prepared by the action of trimethylsilane chloride on a derivative of formula (VI) in which R$_1$, R$_2$ and R$_3$ have the same meanings as in formula (I), Ri denotes a hydrogen atom and Rj denotes an alkyl, -alk-Het or phenylalkyl radical in which the phenyl nucleus is optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals, alk, Het and R$_{10}$ having the same meanings as in formula (I), and then of trioxane.

This reaction is generally performed in an inert solvent such as dimethylformamide, in the presence of sodium hydride and then reaction with trioxane at a temperature of between 0° and 25° C.

Compounds of formula (I) in which R denotes a C(R$_4$)R$_5$ radical in which R$_5$ denotes an —NH—CHO radical can be prepared by the action of a derivative of formula (VI) in which R$_1$, R$_2$ and R$_3$ have the same meanings as in formula (I), Ri denotes an alkyl, -alk-Het or phenylalkyl radical in which the phenyl nucleus is optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals, alk, Het and R$_{10}$ having the same meanings as in formula (I), and Rj denotes an amino radical on CH$_3$COOCHO.

This reaction is preferably performed in an inert solvent such as formic acid, in the presence of sodium acetate, at a temperature close to 20° C.

Compounds of formula (I) in which R denotes a C(R$_4$)R$_5$ radical in which R$_5$ denotes a radical which is —NH—COOR$_{17}$, —NH—CO—Het, —NH—CO-alk-COOR$_{10}$, —NH—CO-alk-NR$_{10}$R$_{18}$, —NH—CO—Ar in which Ar is optionally substituted, —NH—CO-alk-Ar in which Ar is optionally substituted, —NH—SO$_2$—R$_{24}$, —NH—CO-alk-Het, —NH—CO-alk or —NH—CO-cycloalkyl can be prepared by the action of a corresponding compound of formula (I) in which R denotes a C(R$_4$)R$_5$ radical, R$_5$ denotes an —NR$_8$R$_9$ radical and R$_8$ and R$_9$ denote hydrogen atoms on a derivative Hal-Rk in which Hal denotes a halogen atom and Rk denotes a radical which is —COOR$_{17}$, —CO—Het, —CO-alk-COOR$_{10}$, —CO-alk-NR$_{10}$R$_{18}$, —CO-alk-Ar in which Ar is optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals, —SO$_2$—R$_{24}$, —CO-alk-Het, —CO—Ar in which Ar is optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals, —CO-alk or —CO-cycloalkyl, R$_7$, R$_{10}$, R$_{17}$, R$_{18}$, R$_{24}$, Het, Ar and alk having the same meanings as in formula (I).

This reaction is generally performed in an inert solvent such as dimethylformamide, dimethyl sulphoxide, in the presence of an acid-acceptor such as a trialkylamine (for example triethylamine) or an alkali metal hydride (for example sodium hydride), at a temperature close to 20° C.

The derivatives Hal-Rk are marketed or those in which Rk denotes a —CO—Het, —CO-alk-Het, —CO-cycloalkyl, —CO-alk-COOR$_7$, —CO-alk-NR$_{10}$R$_{18}$ or —CO-alk-Ar radical in which Ar is optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals can be obtained from the corresponding carboxylic acids by the action of a phosphorus halide (for example PCl$_5$ or POCl$_3$), preferably in the phosphorus halide, optionally in the presence of an inert solvent such as dichloromethane, at a temperature of between 20° C. and the boiling temperature of the reaction mixture.

Compounds of formula (I) in which R denotes a C(R$_4$)R$_5$ radical in which R$_5$ denotes a radical which is —NH—CO—Het, —NH—CO-alk-COOR$_{10}$, —NH—CO-alk-NR$_{10}$R$_{18}$, —NH—CO—Ar in which Ar is optionally substituted, —NH—CO-alk-Ar in which Ar is optionally substituted, —NH—CO-alk-Het, —NH—CO-alk or —NH—CO-cycloalkyl can also be prepared by the action of a corresponding compound of formula (I) in which R denotes a C(R$_4$)R$_5$ radical, R$_5$ denotes an —NR$_8$R$_9$ radical and R$_8$ and R$_9$ denote hydrogen atoms on a derivative HO—Rl in which Rl denotes a radical which is —CO—Het, —CO-alk-COOR$_{10}$, —CO-alk-NR$_{10}$R$_{18}$, —CO-alk-Ar in which Ar is optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals, —CO-alk-Het, —CO—Ar in which Ar is optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals, —CO-alk or —CO-cycloalkyl, R$_{10}$, R$_{18}$, Het, Ar and alk having the same meanings as in formula (I).

This reaction is generally performed in an inert solvent such as dimethylformamide, in the presence of hydroxybenzotriazole, of 1-(3-dimethylaminopropyl)-3- ethylcarbodiimide and of an organic base such as a trialkylamine (for example triethylamine), at a temperature of between 0° C. and 5° C.

Compounds of formula (I) in which R denotes a $C(R_4)R_5$ radical in which $R_5$ denotes a 1-pyrrolyl radical optionally substituted by a —$COOR_{10}$ radical can be prepared by the action of a derivative of formula (VI) in which $R_1$, $R_2$ and $R_3$ have the same meanings as in formula (I), Ri denotes an alkyl, -alk-Het or phenylalkyl radical in which the phenyl nucleus is optionally substituted by one or more substituents chosen from halogen atoms and alkyl, alkoxy, nitro, amino, hydroxyl, cyano, -alk-$NH_2$, —$COOR_{10}$ and -alk-$COOR_{10}$ radicals, alk, Het and $R_{10}$ having the same meanings as in formula (I) and Rj denotes an amino radical, on a derivative of formula:

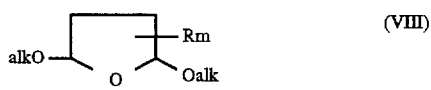

(VIII)

in which Rm denotes a hydrogen atom or a —$COOR_{10}$ radial and alk and $R_{10}$ have the same meanings as in formula (I).

This reaction is generally performed in an inert solvent such as acetic acid, at the boiling temperature of the reaction mixture, optionally in the presence of an acid-acceptor such as sodium acetate.

The derivatives of formula (VIII) can be obtained by application or adaptation of the methods described by J. Fakstorp et al., J. Am. Cham. Soc., 72, 869 (1950), N. Clauson-Kaas et al., Acta Chem. Scan., 6, 551 (1952) and Stibor et al., Collect. Czech. Chem. Commun., 47 (12), 3261 (1992).

Compounds of formula (I) in which R denotes a $C(R_4)R_5$ radical in which $R_5$ denotes a radical which is —NH—CO—NH-alk-Ar in which Ar is optionally substituted, —NH—CO—NH-Het, —NH—CO—NH-alk-Het, —NH—CO—NH—Ar in which Ar is optionally substituted, —NH—CO—NH-alk or —NH—CO—NH$_2$ can be prepared by the action of a corresponding compound of formula (I) in which R denotes a $C(R_4)R_5$ radical, $R_5$ denotes an —$NR_8R_9$ radical and $R_8$ and $R_9$ denote hydrogen atoms on a derivative O=C=N—RN in which Rn denotes a radical which is trimethylsilyl, alkyl, —Het, -alk-Ar in which Ar is optionally substituted by one or more substituents chosen from halogen atoms and alkyl, alkoxy, nitro, amino, hydroxyl, cyano, -alk-$NH_2$, —$COOR_{10}$ and -alk-$COOR_{10}$ radicals, -alk-Het, phenyl optionally substituted by one or more substituents chosen from halogen atoms and alkyl, alkoxy, nitro, amino, hydroxyl, cyano, -alk-$NH_2$, —$COOR_{10}$ and -alk-$COOR_{10}$ radicals in which $R_{10}$, alk, Ar and Het have the same meanings as in formula (I).

This reaction is generally performed in an inert solvent such as dimethylformamide, tetrahydrofuran or dioxane, at a temperature of between 20° C. and the boiling temperature of the reaction mixture. In the case of the compounds in which $R_5$ denotes an —NH—CO—NH$_2$ radical, this reaction is followed by a hydrolysis of the silyl derivative obtained above by means of an aqueous solution, at a temperature of between 20° and 50° C.

The derivatives O=C=N—Rn are marketed or can be obtained by the action of phosgene on the corresponding primary amine, by adapting the methods described by R. L. Shriner et al., Organic Synth., II, 453; G. M. Dyon, Organic Synth., I, 165; R. J. Slocompie et al., J. Am. Chem. Soc., 72, 1888 (1950) and S. Patai, "The chemistry of cyanates and their thio derivatives", Publ. John Wiley and Sons, page 619 (1977). The corresponding primary amines are marketed or those in which Rn denotes a Het or optionally substituted Ar radical can be obtained by application or adaptation of the methods described by B. A. Tertov et al., Khim. Geterotsikl. Soedin., II, 1552 (1972) and R. C. Larock, "Comprehensive Organic Transformations", VCH Publ., page 399, which consists in reacting the organolithium or organomagnesium derivative of the heterocyclic compound or of the optionally substituted benzene with $PhN_3$ in the presence of acetic acid, of $NH_2OCH_3$, $(PHO)_2PON_3$ or of $N_3CH_2Si(CH_3)_3$. The organo-lithium or organomagnesium derivatives can be obtained by application or adaptation of the methods described by D. L. Comins et al., J. Org. Chem., 52, 104 (1987); N. Furukawa et al., Tetrahedron Lett., 28 (47), 5845 (1987); A. R. Katritzky et al., Org. Prep. Procedure Int., 20 (6), 585 (1988); A. J. Clarke et al., Tetrahedron Lett., 27, 2373 (1974) and A. W. Gschwend et al., Organic Reactions, 26, 1 (1979). The amines in which Rn denotes an -alk-Het or -alk-Ar radical in which Ar is optionally substituted are marketed or are obtained from the corresponding halides by the action of $NaN(SiCH_3)_3$ or of the potassium salt of phthalimide, in an inert solvent such as dimethylformamide, in the presence of an organic base such as a trialkylamine or pyridine, at a temperature of between 0° C. and the boiling temperature of the reaction mixture, followed by a hydrolysis in acidic medium (for example HCl), at a temperature of between 20° C. and the boiling temperature of the reaction mixture. The derivatives $H_2$N-alk-Ar in which Ar is optionally substituted can also be obtained by application or adaptation of the methods described by J. F. King et al., J. Am. Chem. Soc., 114, 3028 (1992); B. M. Adger et al., Tetrahedron Lett., 25 (45), 5219 (1984); R. Scarpati et al., Gazz. Chim. Ital., 97 (5), 654 (1967).

Compounds of formula (I) in which R denotes a CH—$R_6$ radical in which $R_6$ denotes a hydroxyl radical can be prepared by reduction of a corresponding compound of formula (I) in which R denotes a C=$R_7$ radical and $R_7$ denotes an oxygen atom.

This reaction is preferably performed in an inert solvent such as a lower aliphatic alcohol (for example methanol or ethanol), in the presence of sodium borohydride, at a temperature of between 15° and 40° C.

Compounds of formula (I) in which R denotes a CH—$R_6$ radical in which $R_6$ denotes a (2–11 C) alkyl or phenylalkyl radical in which the phenyl nucleus is optionally substituted by one or more substituents chosen from halogen atoms and alkyl, alkoxy, nitro, amino, hydroxyl, cyano, -alk-$NH_2$, —$COOR_{10}$ and -alk-$COOR_{10}$ radicals or an -alk-Het radical can be prepared by hydrogenation of a derivative of formula:

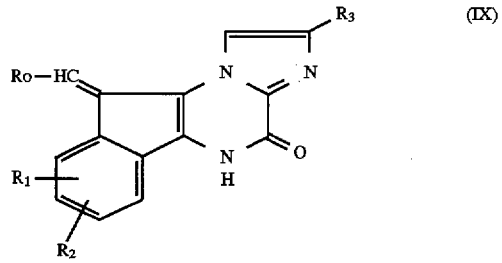

(IX)

in which $R_1$, $R_2$ and $R_3$ have the same meanings as in formula (I), Ro denotes a radical which is alkyl as a straight or branched chain containing I to 10 carbon atoms, phenyl, phenyl(1–5 C)alkyl in which the phenyl nucleus is optionally substituted by one or more substituents chosen from halogen atoms and alkyl, alkoxy, nitro, amino, hydroxyl, cyano, -alk-$NH_2$, —$COOR_{10}$ and -alk-$COOR_{10}$ radicals, —Het and —(1–5 C)alk-Het in which alk, Het and $R_{10}$ have the same meanings as in formula (I).

This reduction is performed by means of hydrogen at a pressure of 1 to 20 bar, in the presence of a hydrogenation catalyst such as palladized charcoal, palladium hydroxide or palladium (N. Rico et al., Nouveau Journal de Chimie, 10, 1, 25 (1986)), in an inert solvent such as dimethylformamide, acetic acid, ethyl acetate, a lower aliphatic alcohol (for example methanol or ethanol) or a mixture of these solvents, at a temperature of between 20° and 60° C. or by adapting the method of L. M. Strawn et al., J. Med. Chem., 32, 2104 (1989), which consists in reacting the ethylene derivative with hydroxylamine sulphate and $H_2NOSO_3H$, in aqueous medium, at a pH of between 6 and 7, at a temperature of 10° C.

The derivatives of formula (IX) in which Ro denotes an alkyl radical as a straight or branched chain containing 5 to 10 carbon atoms can be prepared as described previously for their homologues (compounds of formula (I) in which R denotes a C=$R_7$ radical, $R_7$ denotes a —CH—$R_{19}$ radical and $R_{19}$ denotes an alkyl radical).

Compounds of formula (I) in which R denotes a CH—$R_6$ radical in which $R_6$ denotes an optionally substituted phenylalkyl or -alk-Het radical can also be prepared by the action of a corresponding compound of formula (I) in which R denotes a CH—$R_6$ radical and $R_6$ denotes a hydrogen atom on a halide of formula Hal-Rp in which Rp denotes a phenylalkyl radical in which the phenyl nucleus is optionally substituted by one or more substituents chosen from halogen atoms and alkyl, alkoxy, nitro, amino, hydroxyl, cyano, -alk-$NH_2$, —$COOR_{10}$ and -alk-$COOR_{10}$ or -alk-Het radicals in which alk, Her and $R_{10}$ have the same meanings as in formula (I).

This reaction is preferably performed in an inert solvent such as dimethyl sulphoxide, dimethylformamide, tetrahydrofuran, dioxane or diethyl ether, in the presence of a base such as an alkali metal hydroxide (for example sodium hydroxide or potassium hydroxide), optionally in the presence of tetrabutyl-ammonium bromide or in the presence of an alkali metal hydride (for example sodium hydride), at a temperature close to 20° C.

Compounds of formula (I) in which R denotes a CH—$R_6$ radical in which $R_6$ denotes a (1 C)alkyl radical can be prepared by reduction of a corresponding compound of formula (I) in which R denotes a C=$R_7$ radical, $R_7$ denotes a CH—$R_{19}$ radical and $R_{19}$ denotes a hydroxyl or —$NR_{25}R_{26}$ radical.

This reduction is generally performed by means of hydrogen at a pressure of 1 to 50 bar, in an inert solvent such as dimethylformamide, acetic acid, ethyl acetate, a lower aliphatic alcohol (for example methanol or ethanol) or a mixture of these solvents, in the presence of a hydrogenation catalyst such as palladized charcoal or palladium hydroxide, at a temperature of between 20° C. and 60° C.

Compounds of formula (I) in which R denotes a $CHR_6$ radical and $R_6$ denotes a —(1 C)alk-OH radical can be prepared by reduction of a corresponding compound of formula (I) in which R denotes a C=$R_7$ radical, $R_7$ denotes a CH—$R_{19}$ radical and $R_{19}$ denotes a hydroxyl radical.

This reduction is generally performed with the aid of a reducing agent such as sodium borohydride, in an inert solvent such as a lower aliphatic alcohol (for example methanol or ethanol), at a temperature close to 20° C.

Compounds of formula (I) in which R denotes a $CHR_6$ radical and $R_6$ denotes a —(2–6 C)alk-OH radical can be prepared by reduction of a derivative of formula (IX) in which $R_1$, $R_2$ and $R_3$ have the same meanings as in formula (I), and Ro denotes a —(1–5 C)alk-O—$CH_2$—Ar radical, alk and Ar having the same meanings as in formula (I).

This reduction is preferably performed by means of hydrogen, at a pressure of 1 to 50 bar, in the presence of a catalyst such as palladized charcoal or palladium hydroxide, in an inert solvent such as dimethylformamide, acetic acid, a lower aliphatic alcohol or ethyl acetate, at a temperature of between 20° and 60° C.

The derivatives of formula (IX) in which Ro denotes a —(1–5 C)alk-O—$CH_2$—Ar radical can be obtained by the action of a corresponding compound of formula (I) in which R denotes a CH—$R_6$ radical and $R_6$ denotes a hydrogen atom on an aldehyde OHC—(1–5 C)alk-O—$CH_2$—Ar.

This reaction is performed in the same conditions as those mentioned above for the preparation of the compounds of formula (I) in which R denotes a C=$R_7$ radical, $R_7$ denotes a CH—$R_{19}$ radical and $R_{19}$ denotes an alkyl radical.

The derivatives OHC—(1–5 C)alk-O—$CH_2$—Ar can be obtained by application or adaptation of the methods described by P. Schorigin et al., Chem. Ber., 68, 838 (1935) and A. Gaiffe et al., C. R. Acad. Sc. Paris, Ser. C, 266, 1379 (1968).

Compounds of formula (I) in which R denotes a CH—$R_6$ radical in which $R_6$ denotes an —$NR_{14}R_{15}$ radical and each of $R_{14}$ and $R_{15}$ denotes a hydrogen atom can be prepared by hydrolysis of a corresponding compound of formula (I) in which R denotes a CH—$R_6$ radical in which $R_6$ denotes an —$NR_{14}R_{15}$ radical, $R_{14}$ denotes a hydrogen atom, $R_{15}$ denotes a —$COR_{22}$ radical and $R_{22}$ denotes an alkyl radical, followed, in the case of the compounds in which $R_3$ denotes an alkoxycarbonyl radical, by an esterification of the corresponding acid.

This hydrolysis is generally performed by means of an acid such as hydrochloric acid, in aqueous medium, at the boiling temperature of the reaction mixture. The esterification is performed by means of an aliphatic alcohol ($C_1$–$C_6$ as a straight or branched chain), in acidic medium (for example hydrochloric or sulphuric acid), at the boiling temperature of the reaction mixture.

Compounds of formula (I) in which R denotes a CH—$R_6$ radical in which $R_6$ denotes an —$NR_{14}R_{15}$ radical, $R_{14}$ denotes a hydrogen atom, $R_{15}$ denotes a —$COR_{22}$ radical and $R_{22}$ denotes an alkyl radical can be prepared by the action of a reducing agent on a corresponding compound of formula (I) in which R denotes a C=$R_7$ radical and $R_7$ denotes an NOH radical, followed by the action of an acid anhydride (alkCO)$_2$O in which alk denotes an alkyl radical.

This reaction is generally performed in an inert solvent such as acetic acid, at a temperature of between 50° and 100° C. Zinc is preferably employed as reducing agent.

Compounds of formula (I) in which R denotes a CH—$R_6$ radical and $R_6$ denotes an —$NR_{14}R_{15}$ or -alk-$NR_{14}R_{15}$ radical, in which each of $R_{14}$ and $R_{15}$, which are identical or different, denotes an alkyl radical or else $R_{14}$ denotes a hydrogen atom and $R_{15}$ denotes an alkyl, —$COR_{22}$ or —$SO_2R_{24}$ radical, $R_{22}$ denotes a radical which is alkyl, cycloalkyl, —COOalk, -alk-$COOR_{10}$, phenyl optionally substituted by one or more substituents chosen from halogen atoms and alkyl, alkoxy, nitro, amino, hydroxyl, -alk-$NH_2$, —$COOR_{10}$, cyano and -alk-$COOR_{10}$ radicals, phenylalkyl in which the phenyl nucleus is optionally substituted by one or more substituents chosen from halogen atoms and alkyl, alkoxy, nitro, amino, hydroxyl, -alk-$NH_2$, —$COOR_{10}$, cyano and -alk-$COOR_{10}$ radicals, —$OR_{17}$, —Het, -alk-Het or -alk-$NR_{10}R_{12}$ and $R_{24}$ denotes an alkyl or phenyl radical, can be prepared by the action of a corresponding compound of formula (I) in which each of $R_{14}$ and $R_{15}$ denotes a hydrogen atom on a halide of formula Hal-Rr in which Rr denotes an alkyl, —$COR_{22}$ or —$SO_2R_{24}$ radical, $R_{22}$ denotes a radical which is alkyl, cycloalkyl, —COOalk, -alk-COOR$_{10}$, phenyl optionally substituted by one or more substituents chosen from halogen atoms and alkyl, alkoxy, nitro, amino, hydroxyl, -alk-NH$_2$, —COOR$_{10}$, cyano and -alk-COOR$_{10}$ radicals, phenylalkyl in which the phenyl nucleus is optionally substituted by one or more substituents chosen from halogen atoms and alkyl, alkoxy, nitro, amino, hydroxyl, -alk-NH$_2$, —COOR$_{10}$, cyano and -alk-COOR$_{10}$ radicals, —OR$_{17}$, —Het, -alk-Het or -alk-NR$_{10}$R$_{12}$ and R$_{24}$ denotes an alkyl or phenyl radical, alk, Het, R$_{12}$, R$_{17}$ and R$_{10}$ having the same meanings as in formula (I).

This reaction is preferably performed in an inert solvent such as dimethylformamide, tetrahydrofuran or dimethyl sulphoxide, in the presence of a base such as a tertiary amine (for example triethylamine) or an aromatic one (for example pyridine) or an inorganic base such as an alkali metal hydroxide (for example sodium hydroxide or potassium hydroxide), at a temperature of between 20° C. and the boiling temperature of the reaction mixture.

The derivatives Hal-Rr are marketed or those in which Rr denotes an alkyl or —COR$_{22}$ radical can be obtained from the corresponding carboxylic acids by application or adaptation of the methods described by B. Helferich et al., Organic Synth., I, 147; R. Adams et al., Organic Synth., I, 304 and J. Gason, Organic Synth., III, 169 and those in which Rr denotes an —SO$_2$R$_{24}$ radical can be obtained from the corresponding sulphonic acids by reaction of a halogen derivative of phosphorus (for example PCl$_5$ or POCl$_3$) or of thionyl chloride, in aqueous phase or in an inert solvent (for example dichloromethane), at a temperature of between 20° and 40° C.

The compounds of formula (I) in which R denotes a CH—R$_6$ radical and R$_6$ denotes an —NR$_{14}$R$_{15}$ or -alk-NR$_{14}$R$_{15}$ radical in which R$_{14}$ denotes a hydrogen atom, R$_{15}$ denotes a —COR$_{22}$ or —CSR$_{23}$ radical, R$_{22}$ denotes a radical which is —NH-alk, —NH$_2$, —NH—Ar in which Ar is optionally substituted, —NH-alk-Ar in which Ar is optionally substituted, —NH-alk-Het or —NH—Het and R$_{23}$ denotes an —NH-alk, —NH$_2$ or —NH—Ar radical or —NH—Het can be prepared by the action of a corresponding compound of formula (I) in which R denotes a CH—R$_6$ radical, R$_6$ denotes an —NR$_{14}$R$_{15}$ radical and each of R$_{14}$ and R$_{15}$ denotes a hydrogen atom on a derivative Rs—N=C=Rt in which Rs denotes a radical which is trimethylsilyl, alkyl, phenyl optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals, -alk-Ar in which Ar is optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals, -alk-Het or Het in which Het, alk, R$_{10}$ and Ar have the same meanings as in formula (I) and Rt denotes an oxygen or sulphur atom, followed optionally by a hydrolysis.

This reaction is preferably performed in an inert solvent such as dimethylformamide, tetrahydrofuran or dioxane, at a temperature of between 20° C. and the boiling temperature of the reaction mixture. In the case of the compounds in which R$_{22}$ and R$_{23}$ are NH$_2$ radicals, this reaction is followed by a hydrolysis of the silyl derivative obtained earlier by means of an aqueous solution, at a temperature of between 20° and 50° C.

The derivatives Rs—N=C=Rt can be obtained from the corresponding primary amines by the action of phosgene or of thiophosgene by application or adaptation of the methods described by R. L. Shriner et al., Organic Synth., II, 453 and G. M. Dyson, Organic Synth., I, 1655 R. J. Slocompie et al., J. Am. Chem. Soc., 72, 1888 (1950) and S. Patai, "The chemistry of cyanates and their thio derivatives", Ed. John Wiley and Sons, pages 619 and 819 (1977).

The compounds of formula (I) in which R denotes a CH—R$_6$ radical and R$_6$ denotes an —NR$_{14}$R$_{15}$ or -alk-NR$_{14}$R$_{15}$ radical, in which R$_{14}$ denotes a hydrogen atom, R$_{15}$ denotes a —COR$_{22}$ radical and R$_{22}$ denotes a —(1 C)alk-NR$_{10}$R$_{12}$ radical in which R$_{10}$ and R$_{12}$ are hydrogen atoms can be prepared by the action of a corresponding compound of formula (I) in which each of R$_{14}$ and R$_{15}$ denotes a hydrogen atom on an acid HOOC—CH$_2$—NH—Ru in which Ru denotes a protecting group for the amine functional group, such as tert-butoxycarbonyl, followed by a hydrolysis.

This reaction is preferably performed in an inert solvent such as dimethylformamide, in the presence of hydroxybenzotriazole, of 1-(3-dimethylaminopropyl)-3-ethylcarbodiimide and of an organic base such as a trialkylamine (for example triethylamine), at a temperature of between 0° and 5° C. The hydrolysis is generally performed by means of trifluoroacetic acid, at a temperature close to 20° C.

The compounds of formula (I) in which R denotes a CH—R$_6$ radical, R$_6$ denotes an -alk-NR$_{14}$R$_{15}$ radical, each of R$_{14}$ and R$_{15}$ denotes a hydrogen atom with the exception of those in which R$_3$ denotes a carboxamido radical can be prepared by the action of bromine and sodium hydroxide on a corresponding compound of formula (I) in which R denotes a CH—R$_6$ radical, R$_6$ denotes an -alk-CONR$_{10}$R$_{21}$ radical and R$_{10}$ and R$_{21}$ denote hydrogen atoms.

This reaction is generally performed in aqueous medium, at a temperature of between 20° and 70° C.

Compounds of formula (I) in which R denotes a CH—R$_6$ radical, R$_6$ denotes an -alk-NR$_{14}$R$_{15}$ radical, each of R$_{14}$ and R$_{15}$ denotes a hydrogen atom and R$_3$ denotes a carboxamido radical can be prepared by the action of ammonia on a corresponding compound of formula (I) in which R denotes a CH—R$_6$ radical, R$_6$ denotes an -alk-NR$_{14}$R$_{15}$ radical, each of R$_{14}$ and R$_{15}$ denotes a hydrogen atom and R$_3$ denotes an alkoxycarbonyl radical.

This reaction is performed in an inert solvent such as a lower aliphatic alcohol (for example methanol or ethanol), at a temperature close to 20° C.

Compounds of formula (I) in which R denotes a CH—R$_6$ radical, R$_6$ denotes an —NR$_{14}$R$_{15}$ or -alkNR$_{14}$R$_{15}$ radical in which R$_{14}$ denotes a hydrogen atom and R$_{15}$ denotes a —COR$_{22}$ radical, R$_{22}$ denotes a radical which is alkyl, cycloalkyl, -alkCOOR$_{10}$, optionally substituted phenyl, phenylalkyl in which the phenyl is optionally substituted, Het, -alk-Het or -alk-NR$_{10}$R$_{12}$ can be prepared by the action of a corresponding compound of formula (I) in which R denotes a CH—R$_6$ radical, R$_6$ denotes an —NR$_{14}$R$_{15}$ or -alk-NR$_{14}$R$_{15}$ radical in which each of R$_{14}$ and R$_{15}$ denotes a hydrogen atom on an acid HOOC—R$_{22}$, R$_{22}$ denotes a radical which is alkyl, cycloalkyl, —Het, -alk-COOR$_{10}$, -alk-NR$_{10}$R$_{12}$, phenylalkyl in which the phenyl is optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals, -alk-Het or phenyl optionally substituted by one or more substituents chosen from halogen atoms and alkyl, alkoxy, nitro, amino, hydroxyl, cyano, -alk-NH$_2$, —COOR$_{10}$ and -alk-COOR$_{10}$ radicals, alk, Het, R$_{10}$ and R$_{12}$ having the same meanings as in formula (I) or the corresponding anhydride.

This reaction is generally performed in an inert solvent such as dimethylformamide, in the presence of hydroxybenzotriazole, of 1-(3-dimethylaminopropyl)-3-ethylcarbodiimide and of an organic base such as a trialkylamine (for example triethylamine), at a temperature of between 0° C. and 5° C. When the anhydride is employed the operation is preferably carried out in acetic acid, in the presence of sodium acetate, at a temperature close to 50° C.

Compounds of formula (I) in which R denotes a CH—$R_6$ radical and Ra denotes an -alk-COOR$_{10}$ radical can be prepared by hydrogenation of a corresponding derivative of formula (IX) in which $R_1$, $R_2$ and $R_3$ have the same meanings as in formula (I) and Ro denotes a —(1–5 C)alk-COOR$_{10}$ or —COOR$_{10}$ radical in which alk has the same meanings as in formula (I) and R$_{10}$ denotes an alkyl or phenylalkyl radical, optionally followed by a saponification of the ester thus obtained.

This reduction is performed by means of hydrogen at a pressure of 1 to 20 bar, in the presence of a hydrogenation catalyst such as palladized charcoal, palladium hydroxide or palladium (N. Rico et al., Nouveau Journal de Chimie, 10, 1, 25 (1986)), in an inert solvent such as dimethylformamide, acetic acid, ethyl acetate, a lower aliphatic alcohol (for example methanol or ethanol) or a mixture of these solvents, at a temperature of between 20° and 60° C. or by adaptation of the method of L. M. Strawn et al., J. Med. Chem., 32, 2104 (1989), which consists in reacting the ethylene derivative with hydroxylamine sulphate and $H_2NOSO_3H$, in aqueous medium, at a pH of between 6 and 7, at a temperature of 10° C. The saponification is performed by any known method and, preferably, by means of an acid such as hydrochloric acid, in a lower aliphatic alcohol such as ethanol, at a temperature of 20° to 60° C. or by means of trifluoroacetic acid at a temperature close to 20° to 60° C.

The derivatives of formula (IX) in which $R_1$, $R_2$ and $R_3$ have the same meanings as in formula (I) and Ro denotes a —COOR$_{10}$ radical in which R$_{10}$ denotes an alkyl radical can be obtained by the action of a corresponding compound of formula (I) in which R denotes a CH—$R_6$ radical and $R_6$ denotes a hydrogen atom on an alkyl glyoxalate.

This reaction is performed in an inert solvent such as dimethyl sulphoxide, in the presence of an alkali metal hydride (for example sodium or potassium hydride), at a temperature close to 20° C.

Compounds of formula (I) in which R denotes a CH—$R_6$ radical and $R_6$ denotes an -alk-CO—NR$_{10}$R$_{21}$ radical can be prepared by the action of a corresponding compound of formula (I) in which R denotes a CH—$R_6$ radical and $R_6$ denotes an -alk-COOR$_{10}$ radical, alk having the same meanings as in formula (I) and R$_{10}$ denotes a hydrogen atom or an alkyl radical on an amine HNR$_{10}$R$_{21}$ in which R$_{10}$ and R$_{21}$ have the same meanings as in formula (I).

When the acid is used, the operation is carried out in the presence of a condensing agent employed in peptide chemistry, such as a carbodiimide (for example N,N'-dicyclohexylcarbodiimide) or N,N'-diimidazolecarbonyl, in an inert solvent such as an ether (for example tetrahydrofuran or dioxane), an amide (dimethylformamide) or a chlorinated solvent (for example methylene chloride, 1,2-dichloroethane or chloroform) at a temperature of between 0° C. and the reflux temperature of the reaction mixture. When an ester is used, then the operation is carried out either in organic medium, optionally in the presence of an acid-acceptor such as a nitrogenous organic base (for example trialkylamine, pyridine, 1,8-diazabicyclo[5.4.0]undec-7-ene or 1,5-diazabicyclo[4.3.0]non-5-ene), in a solvent as mentioned above, or a mixture of these solvents, at a temperature of between 0° C. and the reflux temperature of the reaction mixture, or in a two-phase hydroorganic medium in the presence of an alkaline or alkaline-earth base (sodium hydroxide, potassium hydroxide) or of an alkali or alkaline-earth metal carbonate or bicarbonate at a temperature of between 0° and 40° C.

The amines HNR$_{10}$R$_{21}$ can be obtained from the corresponding halides by application or adaptation of the methods described by R. C. Larock, "Comprehensive Organic Transformations", VCH Publ., page 397 (1989).

Compounds of formula (I) in which R denotes a CH—$R_6$ radical, $R_6$ denotes a —(C 1)alk-CO—NR$_{10}$R$_{21}$ radical and R$_{10}$ and R$_{21}$ denote hydrogen atoms can also be prepared by hydrogenation of a derivative of formula (IX) in which $R_1$, $R_2$ and $R_3$ have the same meanings as in formula (I) and Ro denotes a —CONH$_2$ radical.

This reaction is generally carried out either by means of hydrogen, in an inert solvent such as dimethylformamide, in the presence of a hydrogenation catalyst such as palladized charcoal or palladium, at a temperature close to 20° to 30° C., or by application or adaptation of the method of L. M. Strawn et al., J. Med. Chem., 32, 2104 (1989), which consists in reacting the ethylene derivative with hydroxylamine sulphate and $H_2NOSO_3H$, in aqueous medium, at a pH of between 6 and 7, at a temperature of 10° C.

The derivatives of formula (IX) in which $R_1$, $R_2$ and $R_3$ have the same meanings as in formula (I) and Ro denotes a —CONH$_2$ radical can be obtained by the action of ammonia on a corresponding compound of formula (IX) in which Ro denotes a —COOR$_{10}$ radical in which R$_{10}$ denotes an alkyl radical in the conditions described by D. I. Mowry et al., Organic Synth., IV, 486 and J. Kleinberg et al., Organic Synth., IV, 516.

Compounds of formula (I) in which R denotes a CH—$R_6$ radical and $R_6$ denotes an —R$_{16}$—COOR$_{10}$ radical can be prepared by the action of a corresponding compound of formula (I) in which R denotes a CH—$R_6$ radical and $R_6$ denotes a hydrogen atom on a derivative of formula OHC—(0–5 C)alk-COOR$_{10}$ in which alk and R$_{10}$ have the same meanings as in formula (I).

This reaction is preferably performed in an inert solvent such as dimethyl sulphoxide, in the presence of an alkali metal hydride such as sodium hydride, at a temperature close to 20° C.

The derivatives of formula OHC—(0–5 C)alk-COOR$_{10}$ can be obtained by application or adaptation of the method described by L. A. Carpino, J. Org. Chem., 29, 2820 (1964).

Compounds of formula (I) in which R denotes a CH—$R_6$ radical and $R_6$ denotes an —NH—CHO radical can be prepared by the action of a corresponding compound of formula (I) in which R denotes a CH—$R_6$ radical, $R_6$ denotes an —NR$_{14}$R$_{15}$ radical and R$_{14}$ and R$_{15}$ denote hydrogen atoms on CH$_3$COOCHO.

This reaction is preferably performed in an inert solvent such as formic acid, in the presence of sodium acetate, at a temperature close to 20° C.

Compounds of formula (I) in which R denotes a CH—$R_6$ radical and $R_6$ denotes a —CO—COOR$_{10}$ radical can be prepared by oxidation of a corresponding compound of formula (I) in which R denotes a CH—$R_6$ radical, $R_6$ denotes an —R$_{16}$—COOR$_{10}$ radical and R$_{16}$ denotes a —CHOH— radical optionally followed by an esterification.

This oxidation is preferably performed by means of potassium permanganate, in a 3N sodium hydroxide solution, at a temperature close to −3° C. or by means of platinum on charcoal, in a 2N sodium hydroxide solution, at a temperature of 70° C. The esterification is preferably performed by means of a lower aliphatic alcohol in the presence of an acid such as hydrochloric or sulphuric acid, at the boiling temperature of the reaction mixture.

Compounds of formula (I) in which R denotes a CH—$R_6$ radical and $R_6$ denotes a 1-pyrrolyl radical optionally substituted by a —$COOR_{10}$ radical can be prepared by the action of a corresponding compound of formula (I) in which R denotes a CH—$R_6$ radical and $R_6$ denotes an —$NR_{14}R_{15}$ radical and $R_{14}$ and $R_{15}$ denote hydrogen atoms on a derivative of formula (VIII) in which Rm denotes a hydrogen atom or a —$COOR_{10}$ radical in which $R_{10}$ has the same meanings as in formula (I).

This reaction is generally performed in an inert solvent such as acetic acid, optionally in the presence of an acid-acceptor such as sodium acetate, at the boiling temperature of the reaction mixture.

Compounds of formula (I) in which R denotes a CH—$R_6$ radical and $R_6$ denotes a —COOalk radical can be prepared by the action of an inorganic acid on a derivative of formula:

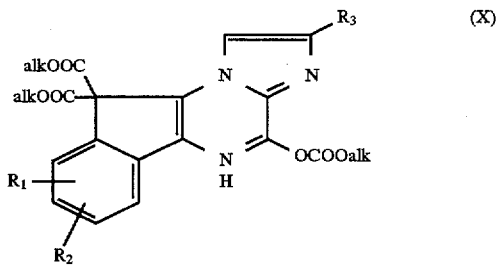

in which $R_1$, $R_2$ and $R_3$ have the same meanings as in formula (I) and alk denotes an alkyl radical.

This reaction is generally performed in an inert solvent such as tetrahydrofuran, at a temperature of 0° C. Hydrochloric acid in 1N aqueous solution is preferably employed as inorganic acid.

The derivatives of formula (X) can be obtained by the action of a corresponding compound of formula (I) in which R denotes a CH—$R_6$ radical and $R_6$ denotes a hydrogen atom on a halide Hal-COOalk in which alk denotes an alkyl radical.

This reaction is generally performed in an inert solvent such as dioxane, in the presence of an alkali metal (for example sodium) hydride, at a temperature of between 20° C. and the boiling temperature of the reaction mixture.

The derivatives Hal-COOalk are marketed or can be obtained by application or adaptation of the methods described in Houben-Weyl, volume 8, page 102 (1952).

Compounds of formula (I) in which $R_3$ denotes a carboxyl radical can also be prepared by hydrolysis of a corresponding compound of formula (I) in which $R_3$ denotes an alkoxycarbonyl radical.

This hydrolysis is performed either by means of an acid (for example hydrochloric or sulphuric acid), in aqueous solution, at a temperature of between 20° C. and the boiling temperature of the reaction mixture; or by means of a base (for example sodium hydroxide, potassium hydroxide or potassium carbonate), in aqueous solution or in hydroorganic medium (for example water-tetrahydrofuran or water-dioxane), at a temperature of between 0° C. and the boiling temperature of the reaction mixture.

Compounds of formula (I) in which $R_1$ and/or $R_2$ denote an —NH—CO—$NR_{11}R_{12}$ radical in which $R_{11}$ denotes a hydrogen atom or a radical which is alkyl (1–9 C as straight or branched chain), -alk-$COOR_{10}$, -alk-Het, -alk-$NR_{12}R_{10}$, phenylalkyl in which the phenyl nucleus is optionally substituted by one or more substituents chosen from halogen atoms and alkyl, alkoxy, nitro, amino, hydroxyl, -alk-$NH_2$, carboxyl, alkoxycarbonyl, cyano and -alk-$COOR_{10}$ radicals, phenyl optionally substituted by one or more substituents chosen from halogen atoms and alkyl, alkoxy, nitro, amino, hydroxyl, -alk-$NH_2$, carboxyl, alkoxycarbonyl, cyano and -alk-$COOR_{10}$ radicals or —Het and $R_{12}$ denotes a hydrogen atom can also be prepared by the action of a corresponding compound of formula (I) in which $R_1$ and/or $R_2$ denotes an amino radical with an isocyanate O=C=$NR_{11}$ in which $R_{11}$ has the same meanings as above or denotes a trimethylsilyl radical.

This reaction is performed in an inert solvent such as tetrahydrofuran, dimethylformamide or dioxane, at a temperature of between 20° C. and the boiling temperature of the reaction mixture. In the case of the compounds in which $R_{11}$ denotes a hydrogen atom, this reaction is followed by a hydrolysis of the silyl derivative previously obtained by means of an aqueous solution, at a temperature of between 20° and 50° C.

The isocyanates O=C=$NR_{11}$ are marketed or can be prepared as described above for the isocyanates of formula O=C=N—Rn.

Compounds of formula (I) in which $R_1$ and/or $R_2$ denote an amino radical can also be prepared by reduction of a corresponding compound of formula (I) in which $R_1$ and/or $R_2$ denote a nitro radical.

This reduction is generally performed by means of hydrogen at a pressure of 1 to 2 bar, in the presence of a catalyst such as palladium on charcoal, at a temperature close to 20° C.

Compounds of formula (I) in which R denotes a CH—$R_6$ radical, $R_6$ denotes an —$NR_{14}R_{15}$ radical and $R_{14}$ and $R_{15}$ denote hydrogen atoms can also be prepared by reduction, in the presence of a reducing agent, of a corresponding compound of formula (I), in which R denotes a C=$R_7$ radical and $R_7$ denotes an NOH radical.

This reaction is preferably performed in a lower aliphatic alcohol (for example ethanol), in the presence of aqueous ammonia and of ammonium acetate, at the boiling temperature of the reaction mixture. Zinc is preferably employed as reducing agent.

Compounds of formula (I) in which R denotes a C=$R_7$ radical, $R_7$ denotes a CH—$R_{19}$ radical, $R_{19}$ denotes a phenyl radical substituted by a $COOR_{10}$ radical and $R_{10}$ denotes a hydrogen atom can also be prepared by hydrolysis of a corresponding compound of formula (I) in which R denotes a C=$R_7$ radical, $R_7$ denotes a CH—$R_{19}$ radical and $R_{19}$ denotes a phenyl radical substituted by a cyano radical.

This reaction is performed by means of an acid such as sulphuric acid, at the boiling temperature of the reaction mixture.

Compounds of formula (I) in which R denotes a CH—$R_6$ radical and $R_6$ denotes a 2-oxo-2,5-dihydro-1-pyrrolyl radical can be prepared by the action of a corresponding compound of formula (I) in which R denotes a CH—$R_6$ radical, $R_6$ denotes an —$NR_{14}R_{15}$ radical and $R_{14}$ and $R_{15}$ denote hydrogen atoms on 2,5-dimethoxy-2,5-dihydrofuran.

This reaction is generally performed in acetic acid, in the presence of sodium acetate, at a temperature of between 40° and 70° C.

A person skilled in the art will understand that, in order to make use of the processes according to the invention which are described above, it may be necessary to introduce groups protecting amino, hydroxyl and carboxyl functional groups in order to avoid secondary reactions. These groups are those that can be removed without affecting the remainder of the molecule. Examples of protecting groups for the amino functional groups which may be mentioned are tert-butyl or methyl carbamates, which can be regenerated by means of iodotrimethylsilane. Examples of protecting groups for the hydroxyl functional group which may be mentioned are triethylsilyl and benzyl. Protecting groups for carboxyl functional groups which may be mentioned are esters (for example methoxymethyl ester, tetrahydropyranyl ester or benzyl ester), oxazoles and 2-alkyl-1,3-oxazolines. Other protecting groups which can be employed are described by W. Greene et al., Protecting Groups in Organic Synthesis, second edition, 1991, John Wiley & Sons.

Compounds of formula (I) can be purified by the usual known methods, for example by crystallization, chromatography or extraction.

The enantiomers of the compounds of formula (I) in which R denotes a $C(R_4)R_5$ or $CH-R_6$ radical can be obtained by resolving the racemates, for example by chromatography on a chiral column according to W. H. Pirckle et al., Asymmetric synthesis, vol. 1, Academic Press (1983) or by synthesis from chiral precursors.

The diastereoisomers of the compounds of formula (I) in which R denotes a $C(R_4)R_5$ or $CH-R_6$ radical containing one or a number of chiral carbons and the different E and Z isomers of the compounds of formula (I) can be separated by the usual known methods, for example by crystallization or chromatography.

Compounds of formula (I) containing a basic residue can be optionally converted into addition salts with an inorganic or organic acid by the action of such an acid in an organic solvent such as a lower aliphatic alcohol, a ketone, an ether or a chlorinated solvent.

Compounds of formula (I) containing an acidic residue can optionally be converted into metal salts or into addition salts with nitrogenous bases by methods which are known per se. These salts can be obtained by the action of a metallic (for example alkali or alkaline-earth metal) base, of ammonia, of an amine or of an amine salt on a compound of formula (I), in a solvent. The salt formed is isolated by the usual methods.

These salts also form part of the invention.

Examples of pharmaceutically acceptable salts which may be mentioned are the addition salts with inorganic or organic acids (such as acetate, propionate, succinate, benzoate, fumarate, maleate, oxalate, methanesulphonate, isethionate, theophyllineacetate, salicylate, methylene-bis-β-oxynaphthoate, hydrochloride, sulphate, nitrate and phosphate), salts with alkali metals (sodium, potassium, lithium) or with alkaline-earth metals (calcium, magnesium), the ammonium salt, and salts of nitrogenous bases (ethanolamine, trimethylamine, methylamine, benzylamine, N-benzyl-β-phenethylamine, choline, arginine, leucine, lysine and N-methylglucamine).

Compounds of formula (I) exhibit advantageous pharmacological properties. These compounds are antagonists of the receptor of α-amino-3-hydroxy-5-methyl-4-isoxazolepropionic acid (AMPA), also known by the name of quisqualate receptor.

Furthermore, compounds of formula (I) are noncompetetive antagonists of the N-methyl-D-aspartate (NMDA) receptor and, more particularly, they are ligands for the glycine modulator sites of the NMDA receptor.

These compounds are therefore useful for treating or preventing any ischaemias (such as focal or global ischaemia) resulting from cerebral vascular accidents, a cardiac arrest, an arterial hypotension, a cardiac or pulmonary surgical intervention or a severe hypoglycaemia. They are also useful in the treatment of the effects due to an anoxia, be it perinatal or following a drowning or due to cerebrospinal lesions. These compounds can also be employed for treating or preventing the development of neurodegenerative diseases, of Huntington's chorea, of Alzheimer's disease, of amyotrophic lateral sclerosis, of olivopontocerebellar atrophy and of Parkinson's disease. These compounds can also be employed against epileptogenic and/or convulsive manifestations, for the treatment of cerebral or spinal traumatisms, traumatisms linked with the degeneration of the inner ear (R. Pujol et al., Neuroreport, 3, 299–302 (1992)) or of the retina (J. L. Monsinger et al., Exp. Neurol., 113, 10–17 (1991)), of anxiety (Kehne et al., Eur. J. Pharmacol., 193, 283 (1991)), of depression (Trullas et al., Eur. J. Pharmacol., 185, 1 (1990)), of schizophrenia (Reynolds, TIPS, 13, 116 (1992)), of Tourette's syndrome, of hepatic encephalopathy, as analgesics (Dickenson et al., Neurosc. Letters, 121, 263 (1991)), antiinflammatory (Sluta et al., Neurosci. Letters, 149, 99–102 (1993)), antianorectics (Sorrels et al., Brain Res., 572, 265 (1992)), antimigraine and antiemetic agents and for treating poisonings by neurotoxins or other substances which are agonists of the NMDA receptor, as well as neurological disorders associated with viral diseases, such as AIDS (Lipton et al., Neuron, 7, 111 (1991)), rabies, measles and tetanus (Bagetta et al., Br. J. Pharmacol., 101, 776 (1990)). These compounds are also useful for the prevention of the symptoms of withdrawal of drugs and of alcohol and of the inhibition of the tolerance of and dependence on opiates. They can also be employed in the treatment of deficiencies linked with mitochondrial anomalies, such as mitochondrial myopathy, Leber's syndrome, Wernicke's encephalopathy, Rett's syndrome, homocysteinaemia, hyperprolinaemia, hydroxybutyricaminoaciduria, saturnine encephalopathy (lead poisoning) and sulphite oxidase deficiency.

The affinity of compounds of formula (I) for the AMPA receptor has been determined by studying the antagonism of the specific binding of [$^3$H]-AMPA to rat cerebral cortex membranes (Honore et al., Neuroscience letters, 54, 27 (1985)). [$^3$H]-AMPA is incubated in the presence of 0.2 mg of proteins at 4° C. for 30 minutes in 10 mM $KH_2PO_4$, 100 mM KSCN, pH 7.5 buffer. The nonspecific binding is determined in the presence of 1 mM L-glutamate. The bound radioactivity is separated by filtration on Pharmacia filters (Printed Filtermate A). The inhibiting activity of these products is lower than or equal to 100 μM.

The affinity of compounds of formula (I) for the glycine site bonded to the NMDA receptor was determined by studying the antagonism of the specific binding of [hu 3H]-DCKA to rat cerebral cortex membranes according to the method described by T. Canton et al., J. Pharm. Pharmacol., 44, 812 (1992). [$^3$H]-DCKA (20 nM) is incubated in the presence of 0.1 mg of proteins at 4° C. for 30 minutes in 50 mM, pH 7.5 HEPES buffer. The nonspecific binding is determined in the presence of 1 mM glycine. The bound radioactivity is separated by filtration on Whatman GF/B filters. The inhibiting activity of these products is lower than or equal to 100 μM.

Compounds of formula (I) exhibit low toxicity. Their LD50 is higher than 50 mg/kg by IP route in the mouse.

The preferred compounds of formula (I) are those in which R denotes a $CH-R_6$, $C=R_7$ or $C(R_4)R_5$ radical, $R_1$ denotes a hydrogen or halogen atom or an —NH—CO—$NR_{11}R_{12}$ radical in which $R_{11}$ is a hydrogen atom and $R_{12}$ is an alkyl radical, $R_2$ denotes a hydrogen atom, $R_3$ denotes a carboxyl, alkoxycarbonyl or carboxamido radical, $R_4$ denotes an alkyl radical, $R_5$ denotes an -alk-$COOR_{10}$ radical, $R_6$ denotes a hydrogen atom or a radical which is -alk-Het, 2-oxo-2,5-dihydropyrrol-1-yl or 1-pyrrolyl substituted by —$COOR_{10}$ or —$NR_{14}R_{15}$, $R_7$ denotes a $CH-R_{19}$, NO-alk-COOR$_{10}$ or NOH radical, R$_{19}$ denotes a Het or phenyl radical substituted by —COOR$_{10}$ and either R$_{14}$ and R$_{15}$ are hydrogen atoms or R$_{14}$ is a hydrogen atom and R$_{15}$ is a —COR$_{22}$ radical in which R$_{22}$ is an -alk-COOR$_{10}$ or —NH—Ar radical.

The following examples illustrate the invention.

EXAMPLE 1

51.2 g of ammonium acetate are added in small portions to a solution of 2 g of diethyl 1-(1-oxoindan-2-yl)imidazole-2,4-dicarboxylate in 80 ml of acetic acid and the mixture is heated to reflux for 2 hours. After cooling to a temperature close to 20° C. the precipitate formed is filtered off and rinsed with distilled water and then with methyl ethyl ketone (2×10 ml) to give 0.65 g of ethyl 4,5-dihydro-4-oxo-10H-imidazol[1,2-a]indeno[1,2-e]pyrazine-2-carboxylate in the form of a beige solid melting above 260° C. (analysis % calculated C: 65.08, H: 4.44, N: 14.23; % found C: 65.2, H: 4.3, N: 13.8).

Diethyl 1-(1-oxoindan-2-yl)imidazole-2,4-dicarboxylate can be prepared as follows: a solution of 17.2 g of diethyl imidazole-2,4-dicarboxylate in 200 ml of dimethylformamide is added dropwise with stirring at a temperature close to 15° C. to a suspension of 3.5 g of 60% sodium hydride in 50 ml of dimethylformamide and stirring is continued for 45 minutes. A solution of 17.1 g of 2-bromoindanone in 250 ml of dimethylformamide is then added over 40 minutes at a temperature close to 15° C. and stirring is continued while the temperature of the reaction mixture is allowed to rise to about 20° C.; stirring is continued in this state for 48 hours. The reaction mixture is concentrated in the rotary evaporator and treated with water and then extracted with dichloromethane (4×150 ml). The organic phase is washed with distilled water, dried over magnesium sulphate, filtered and evaporated in the rotary evaporator. A brown oil (29 g) is obtained, which is chromatographed on a silica column by eluting with dichloromethane to give 11.6 g of diethyl 1-(1-oxoindan-2-yl)imidazole-2,4-dicarboxylate in the form of a porous solid used as such in the subsequent syntheses.

Diethyl imidazole-2,4-dicarboxylate can be prepared as follows: 59 ml of triethylamine, followed by 41.6 g of ethyl propiolate are added dropwise with stirring to a suspension of 46 g of ethyl α-aminooximinoacetate in 800 ml of xylene maintained at a temperature close to 0° C. The temperature of the reaction mixture is allowed to return to around 20° C. and stirring is continued for 48 hours. The reaction mixture is treated with 220 ml of water and the organic phase is washed with 50 ml of distilled water, dried over magnesium sulphate, filtered and concentrated to a half in the rotary evaporator; the insoluble product which has formed is removed by filtration and the filtrate is dried by azeotropy for 24 hours and then evaporated in the rotary evaporator. The evaporation residue is ground in dichloromethane and the crystalline solid which forms is filtered to give 7 g of diethyl imidazole-2,4-dicarboxylate in the form of a beige solid melting at 170° C. By chromatography on a silica column, eluting with a mixture of cyclohexane and ethyl acetate (50-50 by volume), 7.2 g of diethyl imidazole-2,4-dicarboxylate are recovered first from the crystallization filtrate and then, by eluting with ethyl acetate alone, 3 g of diethyl imidazole-2,4-dicarboxylate are recovered.

Ethyl α-aminooximinoacetate can be prepared as described by P. S. Branco et al., Tetrahedron, 48(30), 6335 (1992).

EXAMPLE 2

A solution of 150 mg of 1-(1-oxoindan-2-yl)imidazole-2,4-dicarboxamide in 8 ml of acetic acid is heated to reflux for 7 hours. After cooling to a temperature close to 20° C., the precipitate formed is filtered off, rinsed with distilled water and then with isopropyl ether to give 70 mg of 4,5-dihydro-4-oxo-10H-imidazo[1,2-a]indeno[1,2-e]pyrazine-2-carboxamide in the form of beige solid melting above 260° C. (analysis % calculated C: 63.15, H: 3.79, N: 21.04; % found C: 62.8, H: 3.1, N: 21.3).

1-(1-Oxoindan-2-yl)imidazole-2,4-dicarboxamide can be prepared as follows: a stream of ammonia is passed for 30 minutes into a solution of 125 mg of diethyl 1-(1-oxoindan-2-yl)imidazole-2,4-dicarboxylate in 20 ml of methanol cooled to a temperature close to –30° C. and the temperature of the reaction mixture is then allowed to return to about 20° C. and this mixture is stirred for 48 hours. After evaporation in the rotary evaporator a brown oil (27 mg) is obtained which, after wet grinding, gives 1-(1-oxoindan-2-yl)imidazole-2,4-dicarboxamide in the form of a beige solid melting above 260° C., employed as such in the subsequent syntheses.

EXAMPLE 3

0.44 ml of methyl isocyanate is added dropwise with stirring to a suspension of 580 mg of ethyl 8-amino-4,5-dihydro-4-oxo-10H-imidazo[1,2-a]indeno[1,2-e]pyrazine-2-carboxylate in 10 ml of dimethylformamide and stirring is continued for 12 hours at a temperature close to 20° C. The reaction mixture is then filtered, rinsed with dimethylformamide and dried at 35° C. under vacuum (1 mm Hg; 0.13 kPa). 320 mg of ethyl 8-(3-methylureido)-4,5-dihydro-4-oxo-10H-imidazo[1,2-a]indeno[1,2-e]pyrazine-2-carboxylate are obtained as a dihydrate in the form of a beige solid melting above 260° C. (analysis % calculated C: 53.59, H: 5.25, N: 17.36; % found C: 53.2, H: 4.7, N: 17.7).

Ethyl 8-amino-4,5-dihydro-4-oxo-10H-imidazo[1,2-a]indeno[1,2-e]pyrazine-2-carboxylate can be prepared as follows: a mixture of 1.1 g of ethyl 8-nitro-4,5-dihydro-4-oxo-10H-imidazo[1,2-a]indeno[1,2-e]-pyrazine-2-carboxylate and 40 ml of dimethylformamide is hydrogenated at a temperature close to 20° C. at a pressure of 1.9 bar for 24 hours in the presence of 0.14 g of 10% palladized charcoal. The catalyst is filtered off under inert atmosphere, the filtrate is put aside, the palladized charcoal is resuspended in dimethyl sulphoxide and filtered and this new filtrate is evaporated in the rotary evaporator. A black oil (2 g) is obtained, which is ground in ethanol. The solid obtained is filtered off, rinsed with ethanol and dried to give 0.58 g of ethyl 8-amino-4,5-dihydro-4-oxo-10H-imidazo[1,2-a]indeno[1,2-e]pyrazine-2-carboxylate in the form of a beige solid melting above 260° C., employed as such in the subsequent syntheses.

Ethyl 8-nitro-4,5-dihydro-4-oxo-10H-imidazo[1,2-a]indeno[1,2-e]pyrazine-2-carboxylate can be prepared as follows: 1 g of ethyl 4-oxo-5H,10H-imidazo[1,2-a]indeno[1,2-e]pyrazine-2-carboxylate is added in small portions with stirring to 11 ml of concentrated sulphuric acid cooled to a temperature close to –5° C. while the reaction mixture is maintained at a temperature close to 0° C. After 30 minutes stirring at this temperature 0.34 g of potassium nitrate is added gradually and stirring is continued for 30 minutes at 0° C. The temperature is then allowed to rise to about 20° C. and stirring is continued for 12 hours. The reaction mixture is poured onto ice and the precipitate formed is isolated by filtration, rinsed with distilled water and then with isopropyl ether to give 1.1 g of ethyl 8-nitro-4,5-dihydro-4-oxo-10H-imidazo[1,2-a]indeno[1,2-e]pyrazine-2-carboxylate in the form of a yellow solid melting at about 180° C., employed as such in the subsequent syntheses.

EXAMPLE 4

A mixture of 200 mg of ethyl 8-(3-methylureido)-4,5-dihydro-4-oxo-10H-imidazo[1,2-a]indeno[1,2-e]pyrazine-2-carboxylate, 20 ml of dioxane, 0.5 ml of water and 1.6 ml of 1N sodium hydroxide is stirred for 12 hours at a temperature close to 20° C. After concentration of the reaction mixture in the rotary evaporator it is acidified to pH 1 with 1N hydrochloric acid. The precipitate obtained is filtered off and rinsed with distilled water and then with isopropyl ether to give 120 mg of 8-(3-methylureido)-4,5-dihydro-4-oxo-10H-imidazo[1,2-a]indeno[1,2-e]-pyrazine- 2-carboxylic acid in the form of a chestnut-brown solid melting above 260° C. (NMR spectrum: $^1$H (200 MHz, $(CD_3)_2SO$-$d_6$, δ in ppm): 2.65 (s, 3H: $CH_3$); 3.90 (s, 2H: $CH_2$); 7.30 (d, J=9 Hz, 1H: CH arom); 7.70 (d, J=9 Hz, 1H: CH arom); 7.80 (s, 1H: CH arom); 8.40 (s, 1H: CH arom)).

EXAMPLE 5

The procedure is as in Example 1 but starting from 5 g of diethyl 1-(6-chloro-1-oxoindan-2-yl)imidazole-2,4-dicarboxylate, 118 g of ammonium acetate and 190 ml of acetic acid. After washing the precipitate with water and then with methyl ethyl ketone, the solid obtained is first of all ground in acetonitrile and then in methanol and finally in acetone to obtain 2.7 g of ethyl 7-chloro-4,5-dihydro-4-oxo-10H-imidazo[1,2-a]indeno[1,2-e]pyrazine-2-carboxylate in the form of a brown solid melting above 260° C. (analysis % calculated C: 58.28, H: 3.67, Cl: 10.75, N: 12.74; % found C: 58.6, H: 3.4, Cl: 10.4, N: 13.1).

Diethyl 1-(6-chloro-1-oxoindan-2-yl)imidazole-2,4-dicarboxylate can be prepared as follows: the procedure is as in Example 1 but starting from 17 g of diethyl imidazole-2,4-dicarboxylate, 3.5 g of 60% sodium hydride, 500 ml of dimethylformamide and 19.6 g of 2-bromo-6-chloroindanone. 14 g of diethyl 1-(6-chloro-1-oxoindan-2-yl)imidazole-2,4-dicarboxylate are obtained, employed such in subsequent syntheses.

2-Bromo-6-chloroindanone can be prepared as described by P. Strehlke, G. A. Hoyer and E. Schroeder in Arch. Pharm., 308(2), 94 (1975).

EXAMPLE 6

The procedure is as in Example 2 but starting from 2.7 g of tert-butyl 2-carbamoyl-1-(1-oxoindan-2-yl)imidazole-4-carboxylate and from 35 ml of acetic acid. After drying at 50° C. under vacuum (1 mm Hg; 0.13 kPa), 1.75 g of 4,5-dihydro-4-oxo-10H-imidazo[1,2-a]indeno[1,2-e] pyrazine-2-carboxylic acid are obtained as hydrate in the form of a white solid melting above 260° C. (analysis % calculated C: 58.95, H: 3.89, N: 14.73; % found C: 58.8, H: 4.0, N: 14.5).

tert-Butyl 2-carbamoyl-1-(1-oxoindan-2-yl)imidazole-4-carboxylate can be prepared as follows: the procedure is as in Example 2 but starting from 3.7 g of tert-butyl 2-ethoxycarbonyl-1-(1-oxoindan-2-yl)imidazole-4-carboxylate, 45 ml of methanol and gaseous ammonia. After 20 hours' contact the precipitate which has appeared in the reaction mixture is isolated by filtration, rinsed with methanol and dried under vacuum (15 mm Hg; 2 kPa). 2.7 g of tert-butyl 2-carbamoyl-1-(1-oxoindan-2-yl)imidazole-4-carboxylate are obtained in the form of a white solid melting at 240° C.

tert-Butyl 2-ethoxycarbonyl-1-(1-oxoindan-2-yl) imidazole-4-carboxylate can be prepared as in Example 1 but starting from 5.5 g of tert-butyl 2-ethoxycarbonylimidazole-4-carboxylate, 1 g of 60% sodium hydride, 140 ml of dimethylformamide and 4.8 g of 2-bromoindanone. The crude product (9 g) is chromatographed on a silica column, eluting with a mixture of cyclohexane and ethyl acetate (50-50 by volume). 4.1 g of tert-butyl 2-ethoxycarbonyl-1-(1-oxoindan-2-yl)imidazole-4-carboxylate are obtained in the form of a beige solid foam employed as such in the subsequent syntheses.

tert-Butyl 2-ethoxycarbonyl imidazole-4-carboxylate can be prepared as follows: the procedure is as in Example 1 but starting from 15 g of ethyl α-aminooximinoacetate, 500 ml of xylene, 19.1 of triethylamine and 14.3 ml of tert-butyl propiolate. The crude product (19 g) is chromatographed on a silica column, eluting with a mixture of cyclohexane and ethyl acetate (50-50 by volume) to give 5 g of tert-butyl 2-ethoxycarbonylimidazole-4-carboxylate, employed as such in the subsequent syntheses.

EXAMPLE 7

A suspension of 1.4 g of hydrochloride of 10-amino-4,5-dihydro-4-oxo-10H-imidazo[1,2-a]indeno[1,2-e]pyrazine-2-carboxylic acid, 0.57 ml of 2,5-dimethoxytetrahydrofuran and 0.36 g of sodium acetate in 20 ml of acetic acid is heated to reflux for 1 hour and 30 minutes. After cooling to a temperature close to 20° C., the insoluble matter is filtered off, washed with water and with acetone and then dried to produce 0.65 g of hydrochloride and hydrate of 10-(1-pyrrolyl)-4,5-dihydro-4-oxo-10H-imidazo[1,2-a]indeno[1,2-e]pyrazine-2-carboxylic acid in the form of a white powder whose melting point is higher than 260° C. (analysis $C_{21}H_{15}ClN_4O_4$, 0.2 HCl; % calculated C: 55.89, H: 3.91, N: 14.48, O: 16.55; % found C: 55.9, H: 3.8, N: 13.9, O: 16.4); $^1$H spectrum in DMSO, T=300K, δ in ppm (200 MHz): 6.12 (2H, s, =CH), 6.62 (1H, s, CH), 6.93 (2H, s, =CH), between 7.30 and 7.60 (4H, m, CH arom.), 7.94 (1H, d, J=7 Hz, CH arom.), 12.75 (1H, broad s, NH)).

EXAMPLE 8

0.76 g of zinc powder is added in small portions to a solution made up of 0.77 g of 10-hydroxyimino-4,5-dihydro-4-oxoimidazo[1,2-a]indeno[1,2-e]pyrazine-2-carboxylic acid, 0.46 g of ammonium acetate, 50 ml of 28% aqueous ammonia and 50 ml of absolute ethanol. The reaction mixture is heated to reflux for 5 hours and then cooled to a temperature close to 20° C. and treated dropwise with 40 ml of 6N hydrochloric acid. The precipitate formed is filtered off, washed with water and dried under reduced pressure (1 mm Hg; 0.13 kPa). 0.3 g of hydrochloride and hydrate of 10-amino-4,5-dihydro-4-oxo-10H-imidazo[1,2-a]indeno[1,2-e]pyrazine-2-carboxylic acid are thus obtained in the form of a white powder whose melting point is higher than 260° C. (analysis $C_{14}H_{13}ClN_4O_4$, 0.55 HCl, 0.83 $H_2O$; % calculated C: 49.94, H: 3.89, N: 16.64, O: 19.01; % found C: 50.0, H:3.9, N: 15.5, O: 19.0); $^1$H spectrum in DMSO, T=300K, δ in ppm (200 MHz): 5.42 (1H, s, CH), 7.45 (1H, t, J=7 Hz, CH arom.), 7.52 (1H, t, J=7 Hz, CH arom.), 7.86 (1H, d, J=7 Hz, CH arom.), 7.92 (1H, d, J=7 Hz, CH arom.), 8.88 (1H, s, CH)).

EXAMPLE 9

0.34 g of sodium hydride is added to 1 g of ethyl 4,5-dihydro-4-oxo-10H-imidazo[1,2-a]indeno[1,2-e]pyrazine-2-carboxylate in solution in 20 ml of anhydrous dimethyl sulphoxide, while the temperature of the reaction mixture is maintained below 20° C. 0.44 ml of isoamyl nitrite is then added and stirring is continued for 18 hours at the same temperature. The reaction mixture is then poured into iced water and the solution is acidified with 15 ml of acetic acid. The precipitate formed is filtered off, washed with water, with acetone and then with methanol and finally dried under reduced pressure (1 mm Hg; 0.13 kPa) to produce 0.25 g of 10-hydroxyimino-4,5-dihydro-4-oxo-imidazo[1,2-a]indeno[1,2-e]pyrazine-2-carboxylic acid in the form of a brown powder whose melting point is higher than 260° C. ($^1$H spectrum in DMSO, T=300K, δ in ppm (200 MHz), mixture of the syn and anti isomers: Major isomer: between 7.30 and 7.50 (2H, m, CH arom.), 7.62 (1H, s, CH arom.), 7.82 (1H, d, J=7 Hz, CH arom.), 8.00 (1H, s, CH arom.), 8.20 (1H, d, J=7 Hz, CH arom.), 12.7 (1H, s, NH), 13.0 (1H, s, OH), Minor isomer: between 7.30 and 7.50 (2H, m, CH arom.), 7.51 (1H, s, CH arom.), 7.70 (1H, d, J=7 Hz, CH arom.), 7.88 (1H, d, J=7 Hz, CH arom.), 8.58 (1H, s, CH arom.), 12.7 (1H, s, NH), 13.2 (1H, s, OH)).

EXAMPLE 10

0.58 g of ethyl-chloro-4,5-dihydro-4-oxo-10H-imidazo[1, 2-a]indeno[1,2-e]pyrazine-2-carboxylate in suspension in 10 ml of 6N hydrochloric acid is heated to reflux for 24 hours. After cooling to a temperature close to 20° C., the insoluble matter is filtered off, washed with water and dried under reduced pressure (1 mm Hg; 0.13 kPa) at 45° C. 0.38 g of 7-chloro-4,5-dihydro-4-oxo-10H-imidazo[1,2-a]indeno[1,2-e]-pyrazine-2-carboxylic acid is thus obtained in the form of a beige powder whose melting point is higher than 260° C. (analysis $C_{14}H_{10}ClN_3O_4$; % calculated C: 52.60, H: 3.15, Cl: 11.09, N: 13.14; % found C: 52.9, H: 3.3, Cl: 10.8, N: 12.9); $^1$H spectrum in DMSO, T=300K, δ in ppm (300 MHz): 4.02 (2H, s, CH$_2$), 7.37 (1H, d, J=7 Hz, CH arom.), 7.60 (1H, d, J=7 Hz, CH arom.), 7.92 (1H, s, CH arom.), 8.52 (1H, s, CH arom.), 12.45 (1H, s, NH)).

EXAMPLE 11

A suspension of 0.7 g of ethyl 8-amino-4,5-dihydro-4-oxo-10H -imidazo[1,2-a]indeno[1,2-e]pyrazine-2-carboxylate in 14 ml of 6N hydrochloric acid is heated to reflux for 24 hours. After cooling to a temperature close to 20° C., the insoluble matter is filtered off and washed with water and then with isopropyl ether to produce 0.38 g of hydrochloride and hydrate of 8-amino-4,5-dihydro-4-oxo-10H-imidazo[1,2-a]indeno[1,2-e]pyrazine-2-carboxylic acid in the form of a brown powder whose melting point is higher than 260° C. ($^1$H spectrum in DMSO, T=300K, δ in ppm (300 MHz): 4.08 (2H, s, CH$_2$), 7.42 (1H, d, J=7 Hz, CH arom.), 7.60 (1H, s, CH arom.), 7.97 (1H, d, J=7 Hz, CH arom.), 8.51 (1H, s, CH arom.), 12.5 (1H, s, NH)).

EXAMPLE 12

4.3 ml of 1N sodium hydroxide are added to a suspension of 0.6 g of 5-(2-ethoxycarbonyl-10-methyl-4,5-dihydro-4-oxo-10H-imidazo[1,2-a]indeno[1,2-e]pyrazin-10-yl)valeric acid in 30 ml of dioxane, and stirring is continued for 15 hours at a temperature close to 20° C. The reaction mixture is then acidified with 1N hydrochloric acid and the organic phase is extracted with dichloromethane, dried over magnesium sulphate, filtered and concentrated to dryness under reduced pressure in the rotary evaporator. 0.11 g of hydrate of 5-(2-carboxy-10-methyl-4,5-dihydro-4-oxo-10H-imidazo [1,2-a]indeno[1,2-e]pyrazin-10-yl)valeric acid is obtained in the form of a beige solid which decomposes at 230° C. (analysis $C_{20}H_{21}N_3O_6$, 0.55 H$_2$O; % calculated C 60.14, H: 5.30, N: 10.52; % found C 60.3, H: 5.3, N: 9.4); $^1$H spectrum in DMSO, T=300K, δ in ppm (200 MHz): 1.25 (2H, t, J=6 Hz, CH$_2$), 1.57 (3H, s, CH$_3$), 1.98 (2H, t, J=6 Hz, COCH$_2$), between 2.05 and 2.55 (4H, m, (CH$_2$)$_2$), 7.40 (2H, m, CH arom.), 7.36 (2H, t, J=7 Hz, CH arom.), 7.44 (1H, d, J=7 Hz, CH arom.), 7.50 (2H, d, J=7 Hz, CH arom.), 7.58 (1H, d, J=7 Hz, CH arom.), 7.88 (1H, d, J=7 Hz, CH arom.), 8.60 (1H, s, CH), 12.5 (1H, s, NH)).

5-(2-Ethoxycarbonyl-10-methyl-4,5-dihydro-4-oxo-10H-imidazo[1,2-a]indeno[1,2-e]pyrazin-10-yl)valeric acid can be obtained as follows: 0.71 g of 60% sodium hydride is added gradually to a suspension, maintained at 20° C. and under nitrogen, of 1 g of ethyl 10-methyl-4,5-dihydro-4-oxo-10H-imidazo[1,2-a]indeno[1,2-e]pyrazine-2-carboxylate in 40 ml of anhydrous dimethylformamide. After the release of gas has stopped (approximately 30 minutes) 0.45 ml of trimethylchlorosilane is added dropwise and stirring is continued for 30 minutes at 20° C. 0.57 ml of ethyl ester of 5-bromovaleric acid is then added dropwise to the reaction mixture and the reaction is continued for 15 hours at the same temperature. After addition of 25 ml of distilled water the reaction mixture is acidified with 1N hydrochloric acid. The precipitate formed is filtered off and washed with isopropyl ether to produce 0.84 g of expected product in the form of an ochre solid employed without additional purification in the subsequent stages.

Ethyl 10-methyl-4,5-dihydro-4-oxo-10H-imidazo[1,2-a] indeno[1,2-e]pyrazine-2-carboxylate can be prepared according to the following procedure: a suspension of 8 g of ethyl 10-dimethylaminomethylene-4,5-dihydro-4-oxoimidazo[1,2-a]indeno[1,2-e]pyrazine-2-carboxylate in 200 ml of dimethylformamide is hydrogenated at atmospheric pressure and at ambient temperature for 15 hours in the presence of 0.65 g of 10% palladium on charcoal. The reaction mixture is filtered on Celite and the insoluble matter is washed with dimethylformamide. The filtrate is concentrated to dryness in the rotary evaporator to produce 7.6 g of expected product in the form of an ochre solid whose melting point is higher than 260° C. ($^1$H spectrum in DMSO, T=300K, δ in ppm (300 MHz): 1.36 (3H, t, J=6 Hz, CH$_3$), 1.54 (3H, d, J=6 Hz, CH$_3$), 4.19 (1H, q, J=6 Hz, CH), 4.37 (2H, q, J=6 Hz, OCH$_2$), between 7.30 and 7.45 (2H, m, CH arom.), 7.62 (1H, d, J=7 Hz, CH arom.), 7.88 (1H, d, J=7 Hz, CH arom.), 8.58 (1H, s, CH), 12.5 (1H, s, NH)).

Ethyl 10-dimethylaminomethylene-4,5-dihydro-4-oxo-imidazo[1,2-a]indeno[1,2-e]pyrazine-2-carboxylate can be obtained as follows: 30 ml of tert-butoxy bis (dimethylamino)methane are added dropwise at a temperature close to 20° C. to a suspension of 9 g of ethyl 4,5-dihydro-4-oxo-10H-imidazo[1,2-a]indeno[1,2-e] pyrazine-2-carboxylate in 100 ml of anhydrous dimethylformamide. After 5 hours' stirring at the same temperature the reaction mixture is filtered and the insoluble matter is washed with methanol and acetone. 5.7 g of expected product are thus obtained in the form of a yellow solid whose melting point is higher than 260° C. ($^1$H spectrum in DMSO, T=300K, δ in ppm (200 MHz): 1.38 (3H, t, J=6 Hz, CH$_3$), 3.40 (6H, s, NCH$_3$), 4.40 (2H, q, J=6 Hz, OCH$_2$), 7.19 (1H, t, J=7 Hz, CH arom.), 7.28 (1H, t, J=7 Hz, CH arom.), 7.45 (1H, d, J=7 Hz, CH arom.) 7.95 (1H, d, J=7 Hz, CH arom.), 8.21 (1H, s, NCH), 8.97 (1H, s, CH arom.), 12.3 (1H, s, NH)).

EXAMPLE 13

5 ml of 1N sodium hydroxide are added to a suspension of 0.2 g of ethyl 4,5-dihydro-4-oxo-10H-imidazo[1,2-a] indeno[1,2-e]pyrazine-2-carboxylate in 15 ml of dioxane, and the reaction mixture is stirred vigorously while compressed air is bubbled for 15 hours. After addition of 10 ml of distilled water the mixture is acidified with concentrated hydrochloric acid. The precipitate form is filtered off, washed with water and dried to produce 0.13 g of 4,5-dihydro-4,10-dioxoimidazo[1,2-a]indeno[1,2-e]pyrazine-2-carboxylic acid in the form of a brown powder whose melting point is higher than 260° C. ($^1$H spectrum in DMSO, T=300K, δ in ppm (200 MHz): between 7.35 and 7.65 (3H, m, CH arom. ), 7.75 (1H, d, J=7 Hz, CH arom.), 8.38 (1H, s, CH arom.), 12.5 (1H, s, NH)).

EXAMPLE 14

A solution of 1.26 g of (E)-4,5-dihydro-4-oxo-10-(3-cyanobenzylidene) imidazo[1,2-a]indeno[1,2-e]pyrazine-2-carboxylic acid in 15 ml of 60% sulphuric acid is heated to reflux for 3 hours and 30 minutes. After cooling to a temperature close to 20° C. the reaction mixture is poured onto iced water and the precipitate formed is filtered and then taken up in 1N sodium hydroxide, the insoluble matter is set aside and the filtrate is acidified with concentrated hydrochloric acid. The precipitate is taken up in an acetone-water mixture (50/50 by volume), heated to reflux, filtered hot and dried. 0.27 g of sulphate of (E)-4,5-dihydro-4-oxo-10-(3-carboxybenzylidene)imidazo[1,2-a]indeno[1,2-e]pyrazine-2-carboxylic acid is thus obtained in the form of a yellow powder whose melting point is higher than 260° C. ($^1$H spectrum in DMSO+CD$_3$CO$_2$D, T=300K, δ in ppm (200 MHz); between 7.50 and 7.75 (3H, m, CH arom.), 7.78 (1H, d, J=7 Hz, CH arom.), 7.84 (1H, s, CH ethyl.), 7.88 (1H, d, J=7 Hz, CH arom.), 7.94 (1H, d, J=7 Hz, CH arom.), 8.13 (1H, s, CH arom.), 8.23 (1H, d, J=7 Hz, CH arom.), 9.16 (1H, s, CH arom.)).

(E)-4,5-Dihydro-4-oxo-10-(3-cyanobenzylidene)imidazo[1,2-a]indeno[1,2-e]pyrazine-2-carboxylic acid can be prepared as follows: 0.5 g of sodium hydride are added to a solution made up of 2 g of ethyl 4,5-dihydro-4-oxo-10H-imidazo[1,2-a]indeno[1,2-e]pyrazine-2-carboxylate and of 0.9 g of 3-cyanobenzaldehyde in 30 ml of dimethyl sulphoxide, avoiding the temperature exceeding 20° C. The reaction is continued for 15 hours at a temperature close to 20° C. 30 ml of distilled water followed by 10 ml of acetic acid are then added to the reaction mixture. The precipitate formed is filtered off and then taken up and stirred for 1 hour in a mixture of 50 ml of methanol and 5 ml of 2.5N hydrochloric ether. The insoluble matter is filtered off and then recrystallized from a mixture of dimethylformamide and distilled water (50/50 by volume). 1.26 g of expected product are thus obtained in the form of a green powder whose melting point is higher than 260° C. ($^1$H spectrum in DMSO, T=300K, δ in ppm (250 MHz): 7.2 (1H, s, CH ethyl.), between 7.2 and 8.3 (7H, broad m, CH arom.), 9.1 (1H, s, CH arom.), 12.8 (1H, s, NH), 13.0 (1H, broad s, OH)).

EXAMPLE 15

0.4 g of succinic anhydride is added to a suspension made up of 0.5 g of hydrochloride of 10-amino-4,5-dihydro-4-oxo-10H-imidazo[1,2-a]indeno[1,2-e]pyrazine-2-carboxylic acid and of 0.26 g of sodium acetate in 10 ml of acetic acid heated to 50° C., and the reaction is continued for 5 hours at 50° C. After cooling to a temperature close to 20° C. the reaction mixture is filtered and the insoluble matter is washed with distilled water and dried under reduced pressure (1 mm Hg; 0.13 kPa) at 50° C. 0.39 g of hydrate of 10-(3-carboxypropionylamino)-4,5-dihydro-4-oxo-10H-imidazo[1,2-a]indeno[1,2-e]pyrazine-2-carboxylic acid is obtained in the form of a beige powder whose melting point is higher than 260° C. (analysis C$_{18}$H$_{16}$N$_4$O$_7$, 0.66 H$_2$O; % calculated C: 54.01, H: 4.03, N: 13.99; % found C: 54.0, H: 3.8, N: 13.9; $^1$H spectrum in DMSO, T=300K, δ in ppm (300 MHz): 2.55 (4H, m, (CH$_2$)$_2$), 6.15 (1H, d, J=6 Hz, CH), 7.41 (1H, d, J=7 Hz, CH arom.), 7.49 (1H, t, J=7 Hz, CH arom.), 7.51 (1H, t, J=7 Hz, CH arom.), 7.88 (1H, d, J=7 Hz, CH arom.), 8.07 (1H, s, CH), 8.64 (1H, d, J=6 Hz, NH), 12.65 (1H, s, NH)).

EXAMPLE 16

A solution of 0.5 ml of phenyl isocyanate in 2 ml of anhydrous dimethylformamide is added dropwise at a temperature below 20° C. to a solution containing 0.5 g of hydrochloride of 10-amino-4,5-dihydro-4-oxo-10H-imidazo[1,2-a]indeno[1,2-e]pyrazine-2-carboxylic acid and 0.66 ml of triethylamine in 8 ml of anhydrous dimethylformamide. The reaction is continued for 18 hours at a temperature close to 20° C. and the insoluble matter is then filtered off and dried to produce 0.16 g of dihydrate of the triethylamine salt of 10-(3-phenylureido)-4,5-dihydro-4-oxo-10H-imidazo[1,2-a]indeno[1,2-e]pyrazine-2-carboxylic acid in the form of a cream-coloured solid whose melting point is higher than 260° C. (analysis C$_{27}$H$_{34}$N$_6$O$_6$, 0.46 H$_2$O; % calculated C: 60.22, H: 6.36, N: 15.6; % found C: 60.2, H: 6.2, N: 15.8; $^1$H spectrum in DMSO, T=300K, δ in ppm (300 MHz): 6.04 (1H, d, J=6 Hz, CH), 6.96 (1H, t, J=7 Hz, CH arom.), 7.26 (2H, t, J=7 Hz, CH arom.), 7.36 (2H, t, J=7 Hz, CH arom.), 7.44 (1H, d, J=7 Hz, CH arom.), 7.50 (2H, d, J=7 Hz, CH arom.), 7.58 (1H, d, J=7 Hz, CH arom.), 7.86 (1H, d, J=6 Hz, NH), 8.10 (1H, s, CH), 9.15 (1H, s, NH)).

EXAMPLE 17

0.41 g of 80% sodium hydride are added portionwise at a temperature close to 19° C. under a nitrogen blanket to a stirred solution of 1.63 g of ethyl 4,5-dihydro-4-oxo-10H-imidazo[1,2-a]indeno[1,2-e]pyrazine-2-carboxylate and of 0.63 g of 1-methylimidazole-2-carboxaldehyde in 20 ml of dimethyl sulphoxide. Stirring is continued for 5 hours at approximately 20° C. The reaction mixture is cooled to a temperature close to 12° C. and treated with 30 ml of distilled water, the addition of water being controlled so as to maintain the temperature of the reaction mixture between 22° and 25° C. To finish, 6 ml of acetic acid are added. The suspension is then filtered and the solid thus isolated is washed with water and then with methanol and drained thoroughly overnight. Crude 10-[(1-methylimidazol-2-yl)methylene]-4,5-dihydro-4-oxoimidazo[1,2-a]indeno[1,2-e]pyrazine-2-carboxylic acid is obtained in the form of a black pasty solid, a third of which was purified by suspending in 15 ml of methanol and adding 10 ml of 0.45N hydrochloric acid in ethyl ether. Stirring is continued for 90 minutes and the suspension is then filtered and the solid is washed with a mixture of methanol and ethyl ether (10 ml). After drying at 60° C. under vacuum (1 mm Hg; 0.13 kPa), 0.42 g of 10-[(1-methylimidazol-2-yl)-methylene]-4,5-dihydro-4-oxoimidazo[1,2-a]indeno-[1,2-e]pyrazine-2-carboxylic acid hydrochloride is obtained in the form of a brick-red solid melting above 260° C. (analysis % calculated C: 57.65, H: 3.57, Cl: 8.96, N: 17.69, O: 12.13; % found C: 58.1, H: 3.4, N: 17.1).

1-Methylimidazole-2-carboxaldehyde can be prepared by the process described by P. Fournari et al., Bull. Soc. Chim. Fr., (6), 2438 (1968).

EXAMPLE 18

The procedure is as in Example 17 but starting from 1.48 g of ethyl 4,5-dihydro-4-oxo-10H-imidazo[1,2-a]indeno[1, 2-e]pyrazine-2-carboxylate, 0.55 g of 1-methylimidazole-5-carboxaldehyde, 20 ml of dimethyl sulphoxide and 0.37 g of 80% sodium hydride. The crude 10-[(1-methylimidazol-5-yl)methylene]-4,5-dihydro-4-oxoimidazo[1,2-a]indeno[1,2-e]pyrazine-2-carboxylic acid appears as a black solid, a third of which is purified in the same way as in Example 17. 0.54 g of 10-[(1-methylimidazol-5-yl)methylene]-4,5-dihydro-4-oxoimidazo[1,2-a]indeno[1,2-e]pyrazine-2-carboxylic acid hydrochloride is obtained in the form of a dark green solid melting above 260° C. (analysis % calculated C: 57.66, H: 3.57, Cl: 8.96, N: 17.69, O: 12.13; % found C: 58.1, H: 3.0, N: 16.8).

1-Methylimidazole-5-carboxaldehyde can be prepared by the process described by R. Kirchlechner et al., Synthesis, 247, (1994).

EXAMPLE 19

A mixture of crude 10-[(1-methylimidazol-2-yl)methylene]-4,5-dihydro-4-oxoimidazo[1,2-a]indeno[1,2-e]pyrazine-2-carboxylic acid (the remainder of the crude acid described in Example 17), 50 ml of distilled water and 3 ml of N sodium hydroxide is hydrogenated at a temperature close to 20° C. at a pressure of 1.75 bar for 5 hours in the presence of 0.4 g of 10% palladized charcoal. The catalyst is filtered off under inert atmosphere and the filtrate is acidified with 5 ml of N hydrochloric acid. The precipitate formed is filtered off, washed twice with distilled water and dried at 60° C. under vacuum (1 mm Hg; 0.13 kPa). 0.42 g of 10-[(1-methylimidazol-2-yl)methyl]-4,5-dihydro-4-oxo-10H-imidazo[1,2-a]indeno[1,2-e]pyrazine-2-carboxylic acid hydrochloride is obtained in the form of a light chestnut-brown solid melting above 260° C. (analysis % calculated C: 57.37, H: 4.05, Cl: 8.91, N: 17.60, O: 12.07; % found C: 56.9, H: 6.1, N: 18.1).

EXAMPLE 20

The procedure is as in Example 19 but starting from crude 10-[(1-methylimidazol-5-yl)methylene]-4,5-dihydro-4-oxoimidazo[1,2-a]indeno[1,2-e]pyrazine-2-carboxylic acid (the remainder of the crude acid described in Example 18), 50 ml of distilled water, 3 ml of N sodium hydroxide and 0.4 g of 10% palladized charcoal. 0.45 g of 10-[(1-methylimidazol-5-yl)methyl]-4,5-dihydro-4-oxo-10H-imidazo[1,2-a]indeno[1,2-e]pyrazine -2-carboxylic acid hydrochloride is obtained in the form of a chestnut-brown solid melting above 260° C. (analysis % calculated C: 57.37, H: 4.05, Cl: 8.91, N: 17.60, O: 12.07, % found C: 58.3, H: 4.8, N: 17.1).

EXAMPLE 21

1.1 g of 80% sodium hydride is added portionwise, at a temperature of between 20 and 25° C., under an argon blanket, to a stirred solution of 2 g of 10-hydroxyimino-4,5-dihydro-4-oxoimidazo[1,2-a]indeno[1,2-e]pyrazine-2-carboxylic acid in 40 ml of dimethyl sulphoxide, followed, over ten minutes, by a solution of 1.1 ml of ethyl 4-bromobutyrate in 2 ml of dimethyl sulphoxide and stirring is continued overnight. 5 ml of acetic acid are added slowly to the reaction mixture. The reaction mixture is then poured onto 100 g of crushed ice, adjusted to pH 1 with 6N hydrochloric acid, and 100 ml of methanol are added. The resulting suspension is centrifuged and the solid thus isolated is washed twice with methanol and dried under reduced pressure. The green solid obtained is crystallized from dimethylformamide and, after drying at 80° C. under vacuum (1 mm Hg; 0.13 kPa), 0.84 g of 4-[10-(2-carboxy-4,5-dihydro-4-oxoimidazo[1,2-a]indeno[1,2-e]pyrazinylidene)aminooxy]butyric acid, an 85-15 mixture of the Z and E forms, is obtained in the form of a yellow solid melting above 260° C. (analysis % calculated C: 56.55, H: 3.69, N: 14.65, O: 25.11; % found C: 56.6, H: 3.4, N: 15.1, O: 25.1).

EXAMPLE 22

A solution of 3.42 g of diethyl 1-(5-fluoro-1-oxoindan-2-yl)imidazole-2,4-dicarboxylate and of 7.2 g of ammonium acetate in 25 ml of acetic acid is heated to boiling for 2 hours and then cooled to a temperature close to 20° C. The solid which has appeared is separated off by filtration, washed successively with 3 ml of acetic acid, 6 times with a total of 30 ml of distilled water and twice with a total of 10 ml of acetone and is then dried in air. 0.52 g of product obtained (out of the 2.95 g obtained in all) is suspended for 5 minutes in 5 ml of boiling ethanol, separated off by filtration, washed twice with a total of 6 ml of boiling ethanol and dried at reduced pressure (1 mm Hg; 0.13 kPa) at 60° C. 0.49 g of ethyl 8-fluoro-4-oxo-4,5-dihydro-10H-imidazo[1,2-a]indeno[1,2-e]pyrazine-2-carboxylate, decomposing without melting above 260° C., is thus obtained ($^1$H spectrum in DMSO-$d_6$, T=300K, δ in ppm (250 MHz): 1.32 (3H, t, J=6 Hz, CH$_3$), 3.98 (2H, s, CH$_2$), 4.10 (2H, q, J=6 Hz, OCH$_2$), 7.20 (1H, t, J=7 Hz, CH arom.), 7.45 (1H, d, J=7 Hz, CH arom.), 7.80 (1H, ad, J=7 and 5 Hz, CH arom.), 8.47 (1H, s, CH arom.), 12.4 (1H, s, NH)).

Diethyl 1-(5-fluoro-1-oxoindan-2-yl)imidazole-2,4-dicarboxylate can be prepared as follows: 10.4 g of potassium carbonate are added to a solution of 3.2 g of diethyl imidazole-2,4-dicarboxylate in 80 ml of acetone and, to the suspension which is kept boiling, a solution of 4.8 g of 2-bromo-5-fluoroindanone in 20 ml of acetone is added dropwise over 10 minutes. The mixture is stirred while boiling for 2 hours and, after cooling, for 16 hours at a temperature close to 20° C. and is then concentrated to dryness at reduced pressure (10 mm Hg; 1.3 kPa) at 40° C. 60 ml of distilled water and 150 ml of dichloromethane are added to the product obtained (18 g) and, after separation, the organic solution is washed twice with a total of 120 ml of distilled water, dried over anhydrous magnesium sulphate and concentrated to dryness at reduced pressure (10 mm Hg; 1.3 kPa) at 40° C. The product obtained (5.5 g) is chromatographed on 320 g of neutral silica gel (0.020–0.045) contained in a column of 4.8 cm diameter, eluting with an ethyl acetate-cyclohexane mixture (70-30 by volume), 120-ml fractions being collected. Fractions 35 to 70 are combined and concentrated to dryness at reduced pressure (10 mm Hg; 1.3 kPa) at 40° C. 3.48 g of diethyl 1-(5-fluoro-1-oxoindan-2-yl)imidazole-2,4-dicarboxylate melting at 138° C. are thus obtained.

EXAMPLE 23

A stirred suspension of 0.47 g of ethyl 8-fluoro-4-oxo-4,5-dihydro-10H-imidazo[1,2-a]indeno[1,2-e]pyrazine-2-carboxylate in 10 ml of 6N hydrochloric acid is kept boiling for 16 hours and then cooled to a temperature close to 20° C. The insoluble matter is separated off by filtration, washed twice with a total of 10 ml of distilled water and with 5 ml of acetone and then dried at reduced pressure (1 mm Hg; 0.13 kPa) at 60° C. 0.17 g of 8-fluoro-4-oxo-4,5-dihydro-10H-imidazo[1,2-a]indeno[1,2-e]pyrazine-2-carboxylic acid decomposing without melting above 260° C. is thus obtained ($^1$H spectrum in DMSO-$d_6$, T=300K, δ in ppm (300 MHz): 4.00 (2H, s, CH$_2$), 7.22 (1H, t, J=7 Hz, CH arom.), 7.45 (1H, d, J=7 Hz, CH arom.), 7.82 (1H, dd, J=7 and 5 Hz, CH arom.), 8.47 (1H, s, CH arom.), 12.4 (1H, s, NH), 12.8 (1H, s, COOH)).

EXAMPLE 24

A solution of 0.5 g of 2,5-dimethoxy-2,5-dihydrofuran in 1 ml of acetic acid is added dropwise over 1 minute at 50° C. to a suspension of 1 g of hydrochloride of 10-amino-4-oxo-4,5-dihydro-10H-imidazo[1,2-a]indeno[1,2-e]pyrazine-2-carboxylic acid and of 0.57 g of sodium acetate in 15 ml of acetic acid. The mixture is stirred for 2 hours at 65° C. and, after cooling, for 16 hours at a temperature close to 20° C. and then concentrated to dryness at reduced pressure (10 mm Hg; 1.3 kPa) at 60° C. The product obtained (2.7 g) is stirred in suspension in 30 ml of distilled water, is separated by filtration, washed twice with a total of 20 ml of distilled water and with 10 ml of acetone and then dried in air. 0.48 g of product obtained (out of 0.68 g obtained in all) is chromatographed on 29 g of neutral silica gel (0.020–0.045) contained in a column of 2.7 cm diameter, eluting under pressure with a mixture of chloroform, methanol and 28% aqueous ammonia solution (12/6/1 by volume). The fractions containing the expected product are combined and concentrated to dryness at reduced pressure (10 mm Hg; 1.3 kPa) at 40° C. The product (0.23 g) is suspended in 5 ml of isopropyl ether, separated off by filtration, washed with 5 ml of isopropyl ether and dried at reduced pressure (1 mm Hg; 0.13 kPa) at 60° C. 0.19 g of ammonium 4-oxo-10-[1-(2-oxo-2,5-dihydropyrrolyl)]-4,5-dihydro-10H-imidazo[1,2-a]indeno[1,2-e]pyrazine-2-carboxylate decomposing without melting above 260° C. is thus obtained (1H spectrum in DMSO-$d_6$, T=300K, δ in ppm (250 MHz): 3.48 and 3.70 (1H each, d, J=16 Hz, NCH$_2$), 6.33 (1H, d, J=4 Hz, COCH), 6.39 (1H, s, NCH), between 7.30 and 7.60 (4H, m, CH arom.), 7.60 (1H, s, CH arom.), 7.90 (1H, d, J=7 Hz, CH arom.)).

The medications according to the invention consist of a compound of formula (I) or a salt of such a compound, in the pure state or in the form of a composition in which it is used in combination with any other pharmaceutically compatible product which may be inert or physiologically active. The medications according to the invention may be employed by the oral, parenteral, rectal or topical route.

Tablets, pills, powders (gelatin capsules or cachets) or granules may be employed as solid compositions for oral administration. In these compositions the active principle according to the invention is mixed with one or a number of inert diluents such as starch, cellulose, sucrose, lactose or silica, under a stream of argon. These compositions may also include substances other than the diluents, for example one or more lubricants such as magnesium stearate or talc, a dye, a coating (sugar-coated tablets) or a varnish.

Pharmaceutically acceptable solutions, suspensions, emulsions, syrups and elixirs containing inert diluents such as water, ethanol, glycerol, vegetable oils or liquid paraffin may be employed as liquid compositions for oral administration. These compositions may include substances other than the diluents, for example wetting products, sweeteners, thickeners, flavourings or stabilizers.

Sterile compositions for parenteral administration may be preferably aqueous or nonaqueous solutions, suspensions or emulsions. Water, propylene glycol, a polyethylene glycol, vegetable oils, in particular olive oil, injectable organic esters, for example ethyl oleate, or other suitable organic solvents may be employed as solvent or carrier. These compositions may also contain adjuvants, in particular wetting, isotonicity, emulsifying, dispersing and stabilizing agents. The sterilization may be done in a number of ways, for example by aseptizing filtration, by incorporating sterilizing agents into the composition, by irradiation or by heating. They may also be prepared in the form of sterile solid compositions which may be dissolved at the time of use in sterile water or any other injectable sterile medium.

The compositions for rectal administration are suppositories or rectal capsules which, besides the active product, contain excipients such as cocoa butter, semisynthetic glycerides or polyethylene glycols.

Compositions for topical administration may be, for example, creams, lotions, eye lotions, mouthwashes, nasal drops or aerosols.

In human therapeutics the compounds according to the invention are particularly useful for the treatment and/or the prevention of the conditions which require the administration of an antagonist of the AMPA receptor or of an antagonist of the NMDA receptor. These compounds are especially useful for treating or preventing any ischaemias and in particular cerebral ischaemia, the effects due to an anoxia, the development of neurodegenerative diseases, of Huntington's chorea, of Alzheimer's disease, of amyotrophic lateral sclerosis, of olivopontocerebellar atrophy and of Parkinson's disease, against epileptogenic and/or convulsive manifestations, for the treatment of cerebral and spinal traumatisms, traumatisms linked with the degeneration of the inner ear or of the retina, of anxiety, of depression, of schizophrenia, of Tourette's syndrome, of hepatic encephalopathy, as analgesics, antiinflammatories, antianorectics, antimigraine and antiemetic agents and for treating poisonings by neurotoxins or other substances which are agonists of the NMDA receptor, as well as neurological disorders associated with viral diseases, such as AIDS, rabies, measles and tetanus. These compounds are also useful for the prevention of the symptoms of withdrawn of drugs and of alcohol and of the inhibition of the tolerance of and dependence on opiates, and for the treatment of deficiencies linked with mitochondrial anomalies, such as mitochondrial myopathy, Leber's syndrome, Wernicke's encephalopathy, Rett's syndrome, homocysteinaemia, hyperprolinaemia, hydroxybutyric-aminoaciduria, saturnine encephalopathy (lead poisoning) and sulphite oxidase deficiency.

The doses depend on the required effect, the duration of the treatment and the route of administration employed; they are generally between 10 mg and 100 mg per day orally for an adult, with unit doses ranging from 5 mg to 50 mg of active substance.

In general, the doctor will determine the appropriate posology as a function of the age, the weight and all the other factors pertaining to the subject to be treated.

The following examples illustrate compositions according to the invention:

EXAMPLE A

Gelatin capsules containing 50-mg doses of active product which have the following composition are prepared by the usual technique:

| | |
|---|---|
| Compound of formula (I) | 50 mg |
| Cellulose | 18 mg |
| Lactose | 55 mg |
| Colloidal silica | 1 mg |

| | |
|---|---|
| Sodium carboxymethyl starch | 10 mg |
| Talc | 10 mg |
| Magnesium stearate | 1 mg |

EXAMPLE B

Tablets containing 50-mg doses of active product which have the following composition are prepared by the usual technique:

| | |
|---|---|
| Compound of formula (I) | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Mixture of hydroxymethyl cellulose, glycerine and titanium oxide (72-3.5-24.5) q.s. for 1 film-coated tablet finished at | 245 mg |

EXAMPLE C

An injectable solution containing 10 mg of active product which has the following composition is prepared:

| | |
|---|---|
| Compound of formula (I) | 10 mg |
| Benzoic acid | 80 mg |
| Benzyl alcohol | 0.06 ml |
| Sodium benzoate | 80 mg |
| 95% ethanol | 0.4 ml |
| Sodium hydroxide | 24 mg |
| Propylene glycol | 1.6 ml |
| Water q.s. | 4 ml |

We claim:

1. A compound of formula (I):

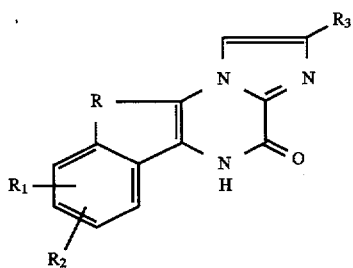

in which,

R denotes an N-alk, $C(R_4)R_5$, CH—$R_5$ or C=$R_6$ radical, $R_1$ and $R_2$, which are identical or different, denote hydrogen or halogen atoms or radicals selected from alkyl, alkoxy, amino, —N=CH-N(alk)alk', nitro, cyano, phenyl, imidazolyl, $SO_3H$, hydroxyl, polyfluoroalkoxy, carboxyl, alkoxycarbonyl, —NH—CO—$NR_{11}R_{12}$, —N(alk)-CO—$NR_{11}R_{12}$, —N(alk-Ar)—CO—$NR_{11}R_{12}$, —NH—CS—$NR_{11}R_{12}$, —N(alk)-CS—$NR_{11}R_{12}$, —NH—CO—$R_{11}$, —NH—CS—$R_{24}$, —NH—C(=$NR_{27}$)—$NR_{10}R_{12}$, —N(alk)-C(=$NR_{27}$)—$NR_{10}R_{12}$, —CO—$NR_{10}R_{12}$, —NH—$SO_2$—$NR_{10}R_{12}$, —N(alk)-$SO_2$—$NR_{10}R_{12}$, —NH—$SO_2$—$CF_3$, —NH—$SO_2$-alk, —$NR_{10}R_{13}$, —$S(O)_m$-alk-Ar, —$SO_2$—$NR_{10}R_{12}$, 2-oxo-1-imidazolidinyl in which position 3 is optionally substituted by an alkyl radical and 2-oxo-1-perhydropyrimidinyl in which position 3 is optionally substituted by an alkyl radical, $R_3$ denotes a carboxyl, alkoxycarbonyl or carboxamido radical, $R_4$ denotes an alkyl, -alk-Het or phenylalkyl radical in which the phenyl nucleus may be substituted by one or more substituents selected from halogen atoms and alkyl, alkoxy, nitro, amino, hydroxyl, cyano, -alk-$NH_2$, —$COOR_{10}$ and -alk-$COOR_{10}$ radicals, $R_5$ denotes an alkyl radical containing from 1 to 11 carbon atoms in a straight or branched chain, an -alk-Het, —$NR_8R_9$, —NH—CHO, —NH—$COOR_{17}$, —NH—$SO_2R_{24}$, —$COOR_{10}$, -alk-$COOR_{10}$, -alk-$CONR_{10}R_{18}$, -alk-$NR_{10}R_{18}$, -alk-OH, -alk-CN, phenylalkyl in which the phenyl nucleus may be substituted by one or more substituents selected from halogen atoms, alkyl, alkoxy, nitro, amino, hydroxyl, cyano, -alk-$NH_2$, —$COOR_{10}$ and -alk-$COOR_{10}$ radicals, —NH—CO—Ar in which Ar may be substituted by one or more substituents selected from halogen atoms, alkyl, alkoxy, nitro, amino, hydroxyl, cyano, -alk-$NH_2$, —$COOR_{10}$ and -alk-$COOR_{10}$ radicals, —NH—CO—Het, —NH—CO-alk-Het, —NH—CO-alk-$COOR_{10}$, —NH—CO-alk-$NR_{10}R_{18}$, —NH—CO-alk-Ar in which Ar may be substituted by one or more substituents selected from halogen atoms, alkyl, alkoxy, nitro, amino, hydroxyl, cyano, -alk-$NH_2$, —$COOR_{10}$ and -alk-$COOR_{10}$ radicals, 1-pyrrolyl which may be substituted by a —$COOR_{10}$ radical, —NH—CO—NH-alk-Ar in which Ar may be substituted by one or more substituents selected from halogen atoms and alkyl, alkoxy, nitro, amino, hydroxyl, cyano, -alk-$NH_2$, —$COOR_{10}$ and -alk-$COOR_{10}$ radicals, —NH—CO—NH—Het, —NH—CO—NH-alk-Het, —NH—CO—NH—Ar in which Ar may be substituted by one or more substituents selected from halogen atoms, alkyl, alkoxy, nitro, amino, hydroxyl, cyano, -alk-$NH_2$, —$COOR_{10}$ and -alk-$COOR_{10}$ radicals, —NH—COalk, —NH—COcycloalkyl, —NH—CO—NH-alk and —NH—CO—$NH_2$, or $R_4$ and $R_5$ form, together with the carbon atom to which they are attached, a cycloalkyl radical, $R_6$ denotes a hydrogen atom or a radical which is hydroxyl, an alkyl group having from 1 to 11 carbon atoms in a straight or branched chain, -alk-OH, —$NR_{14}R_{15}$, -alk-$NR_{14}R_{15}$, -alk-Het, —NH—CHO, —COOalk, -alk-$COOR_{10}$, -alk-CO—$NR_{10}R_{21}$, phenylalkyl in which the phenyl nucleus may be substituted by one or more substituents selected from halogen atoms and alkyl, alkoxy, nitro, amino, hydroxyl, cyano, -alk-$NH_2$, —$COOR_{10}$ and -alk-$COOR_{10}$ radicals, —$R_{16}COOR_{10}$, —CO—$COOR_{10}$, 1-pyrrolyl which may be substituted by a —$COOR_{10}$ or a 2-oxo-2,5-dihydropyrrol-1-yl radical, $R_7$ denotes an oxygen atom or an NOH, NO-alk-$COOR_{10}$, NO-alk, CH$R_{19}$, N$R_{10}$, C($COOR_{10}$)$R_{20}$ or C($CONR_{10}R_{21}$)$R_{20}$ radical, $R_8$ denotes a hydrogen atom or an alkyl, -alk-$COOR_{10}$, -alk-$NR_{10}R_{21}$, -alk-Het or phenylalkyl radical in which the phenyl nucleus may be substituted by one or more substituents selected from halogen atoms and alkyl, alkoxy, nitro, amino, hydroxyl, cyano, -alk-$NH_2$, —$COOR_{10}$ and -alk-$COOR_{10}$ radicals, $R_9$ denotes a hydrogen atom or an alkyl radical, $R_{10}$ denotes a hydrogen atom or an alkyl radical, $R_{11}$ denotes a hydrogen atom or a radical selected from alkyl having 1 to 9 carbon atoms in a straight or branched chain, -alk-COOR$_{10}$, -alk-Het, -alk-NR$_{12}$R$_{10}$, phenylalkyl in which the phenyl nucleus may be substituted by one or more substituents selected from halogen atoms and alkyl, alkoxy, nitro, amino, hydroxyl, -alk-NH$_2$, carboxyl, alkoxycarbonyl, cyano and -alk-COOR$_{10}$ radicals, phenyl which may be substituted by one or more substituents selected from halogen atoms and alkyl, alkoxy, nitro, amino, hydroxyl, -alk-NH$_2$, carboxyl, alkoxycarbonyl, cyano and -alk-COOR$_{10}$ radicals, or —Het, $R_{12}$ denotes a hydrogen atom or an alkyl radical, $R_{13}$ denotes an alkyl, Het or alkoxycarbonyl radical, each of $R_{14}$ and $R_{15}$, which are identical or different, denotes an alkyl radical or $R_{14}$ denotes a hydrogen atom and $R_{15}$ denotes a hydrogen atom or an alkyl, -COR$_{22}$, —CSR$_{23}$ or —SO$_2$R$_{24}$ radical, $R_{16}$ denotes a —CHOH-alkyl or —CH(OH)-alkyl chain, wherein said alkyl has 1 to 5 carbon atoms, $R_{17}$ denotes an alkyl or phenylalkyl radical, $R_{18}$ denotes a hydrogen atom or an alkyl radical, $R_{19}$ denotes a hydroxyl, alkyl, -alk-Het, —NR$_{25}$R$_{26}$, -alk-COOR$_{10}$, —Het or phenyl radical which may be substituted by one or more substituents selected from halogen atoms and alkyl, alkoxy, nitro, amino, hydroxyl, -alk-NH$_2$, —COOR$_{10}$, cyano and -alk-COOR$_{10}$ radicals or phenylalkyl in which the phenyl nucleus is optionally substituted by one or more substituents selected from halogen atoms and alkyl, alkoxy, nitro, amino, hydroxyl, -alk-NH$_2$, —COOR$_{10}$, cyano and -alk-COOR$_{10}$ radicals, $R_{20}$ denotes a hydrogen atom or an alkyl radical, $R_{21}$ denotes a hydrogen atom or an alkyl radical, $R_{22}$ denotes an alkyl, cycloalkyl, —COOalk, -alk-COOR$_{10}$ or phenyl radical which may be substituted by one or more substituents selected from halogen atoms and alkyl, alkoxy, nitro, amino, hydroxyl, -alk-NH$_2$, —COOR$_{10}$, cyano and -alk-COOR'$_{10}$ radicals, phenylalkyl in which the phenyl nucleus may be substituted by one or more substituents selected from halogen atoms and alkyl, alkoxy, nitro, amino, hydroxyl, -alk-NH$_2$, —COOR$_{10}$, cyano and -alk-COOR$_{10}$ radicals, -alk-NR$_{10}$R$_{12}$, —NH—Ar in which Ar may be substituted by one or more substituents selected from halogen atoms and alkyl, alkoxy, nitro, amino, hydroxyl, -alk-NH$_2$, —COOR$_{10}$, cyano and -alk-COOR$_{10}$ radicals, —Het, -alk-Het, -OR$_{17}$, —NH-alk-Ar in which Ar may be substituted by one or more substituents selected from halogen atoms, alkyl, alkoxy, nitro, amino, hydroxyl, -alk-NH$_2$, —COOR$_{10}$, cyano and -alk-COOR$_{10}$ radicals, —NH-alk-Het, —NH-alk, —NH$_2$ and —NH—Het, $R_{23}$ denotes an —NH-alk, —NH—Ar, —NH—Het or —NH$_2$ radical, $R_{24}$ denotes an alkyl or phenyl radical, each of $R_{25}$ and $R_{26}$, which are identical or different, denotes an alkyl or cycloalkyl radical, $R_{27}$ denotes a hydrogen atom or an alkyl radical, alk denotes an alkyl or an alkylene radical, alk' denotes an alkyl radical, m is equal to 0, 1 or 2, Ar denotes a phenyl radical, Het denotes a saturated or unsaturated mono- or polycyclic heterocyclic ring containing from 1 to 9 carbon atoms and one or more heteroatoms selected from O, S, and N, which may be substituted by one or more alkyl, phenyl or phenylalkyl radicals, it being understood that the alkyl, alkylene and alkoxy radicals and the alkyl, alkylene and alkoxy portions of radicals contain 1 to 6 carbon atoms and form a straight or branched chain, the acyl radicals and acyl portions of radicals contain 2 to 4 carbon atoms and the cycloalkyl radicals contain 3 to 6 carbon atoms;

for those compounds in which $R_7$ denotes an NO-alk, C(COOR$_{10}$)R$_{20}$ or C(CONR$_{10}$R$_{21}$)R$_{20}$, CHR$_{19}$ radical, an E or Z isomer of said compound of formula I;

for those compounds in which R denotes a CH—R$_6$ radical and R$_6$ denotes a —CO—COOR$_{10}$ radical, an E or Z tautomeric form of said compound of formula I; and for those compounds in which R denotes a C(R$_4$)R$_5$ or CH—R$_6$ radical, an enantiomer, a diastereoisomer, or a salt of said compound of formula I.

2. A compound of formula (I) according to claim 1, in which Het is a ring selected from pyrrolyl optionally substituted by one or more alkyl, phenyl or phenylalkyl radicals; pyridyl optionally substituted by one or more alkyl, phenyl or phenylalkyl radicals; pyrimidinyl optionally substituted by one or more alkyl, phenyl or phenylalkyl radicals; imidazolyl optionally substituted by one or more alkyl, phenyl or phenylalkyl radicals; thiazolyl optionally substituted by one or more alkyl, phenyl or phenylalkyl radicals; oxazolinyl optionally substituted by one or more alkyl, phenyl or phenylalkyl radicals; thiazolinyl optionally substituted by one or more alkyl, phenyl or phenylalkyl radicals; pyrazinyl optionally substituted by one or more alkyl, phenyl or phenylalkyl radicals; tetrazolyl optionally substituted by one or more alkyl, phenyl or phenylalkyl radicals; and triazolyl optionally substituted by one or more alkyl, phenyl or phenylalkyl radicals.

3. A process for preparing a compound of formula (I) according to claim 1, in which R denotes an N-alk or CH—R$_6$ radical, R$_6$ denotes a hydrogen atom and R$_3$ denotes an alkoxycarbonyl radical with the exception of tert-butoxycarbonyl, said process comprising the steps of cyclizing, in the presence of ammonium acetate, a derivative of formula:

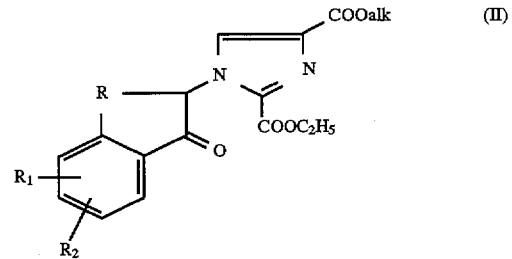

in which R denotes an N-alk or CH—R$_6$ radical, R$_6$ denotes a hydrogen atom, R$_1$ and R$_2$ have the same meanings as recited in claim 1 and —COOalk denotes an alkoxycarbonyl radical except for tert-butoxycarbonyl; isolating the product of said cyclization; and optionally converting said isolated product into a salt.

4. A process for preparing a compound of formula (I) according to claim 1, in which R denotes an N-alk or CH—R$_6$ radical, R$_6$ denotes a hydrogen atom and R$_3$ denotes a tert-butoxycarbonyl radical, said process comprising the steps of reacting isobutene with a compound of formula (I) in which R denotes an N-alk or CH—R$_6$ radical, $R_6$ denotes a hydrogen atom and $R_3$ denotes a carboxyl radical; isolating the product of said reaction; and optionally converting said isolated product into a salt.

5. A process for preparing a compound of formula (I) according to claim 1, in which R denotes an N-alk or CH—$R_6$ radical, $R_6$ denotes a hydrogen atom and $R_3$ denotes a carboxyl radical, said process comprising the steps of cyclizing, in the presence of ammonium acetate, a derivative of formula:

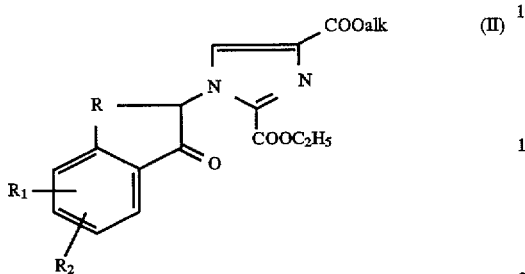

in which R denotes an N-alk or CH—$R_6$ radical, $R_6$ denotes a hydrogen atom and COOalk denotes a tert-butoxycarbonyl radical; isolating the product of said cyclization; and optionally converting said isolated product into a salt.

6. A process for preparing a compound of formula (I) according to claim 1, in which R denotes an N-alk or CH—$R_6$ radical, $R_6$ denotes a hydrogen atom and $R_3$ denotes a carboxamido radical, said process comprising the steps of cyclizing a derivative of formula:

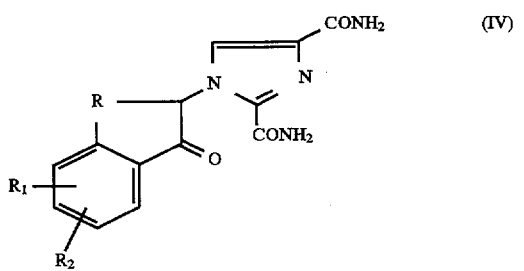

in which R denotes an N-alk or CH—$R_6$ radical, $R_6$ denotes a hydrogen atom and $R_1$ and $R_2$ have the same meanings as in claim 1; isolating the product of said cyclization and optionally converting said isolated product into a salt.

7. A process for preparing a compound of formula (I) according to claim 1, in which R denotes a C=$R_7$ radical in which $R_7$ denotes an oxygen atom, said process comprising the steps of hydrolysing a compound of formula (I) in which R denotes a C=$R_7$ radical and $R_7$ denotes an NOH radical; then, for compounds in which $R_3$ denotes an alkoxycarbonyl radical, esterifying the corresponding acid; isolating the product of said hydrolysation or esterification; and optionally converting said isolated product into a salt.

8. A process for preparing a compound of formula (I) according to claim 1, in which R denotes a C=$R_7$ radical and $R_7$ denotes an NOH radical, said process comprising the steps of reacting an alkyl nitrite with a compound of formula (I) in which R denotes a CH—$R_6$ radical and $R_6$ denotes a hydrogen atom; isolating the product of said reaction; and optionally converting said isolated product into a salt.

9. A process for preparing a compound of formula (I) according to claim 1, in which R denotes a C=$R_7$ radical and $R_7$ denotes an NO-alk-$COOR_{10}$ or NO-alk radical, said process comprising the steps of reacting a compound of formula (I) in which R denotes a C=$R_7$ radical and $R_7$ denotes an NOH radical with a Hal-Ra halide in which Hal denotes a halogen atom and Ra denotes an alkyl or -alk-$COOR_{10}$ radical, alk and $R_{10}$ having the same meanings as in claim 1; isolating the product of said reaction; and optionally converting said isolated product into a salt.

10. A process for preparing a compound of formula (I) according to claim 1, in which R denotes a C=$R_7$ radical and $R_7$ denotes a CH—$R_{19}$ radical in which $R_{19}$ denotes a hydroxyl radical, said process comprising the steps of hydrolysing a compound of formula (I) in which $R_{19}$ denotes an —$NR_{25}R_{26}$ radical; then, for compounds in which $R_3$ denotes an alkoxycarbonyl radical, esterifying the corresponding acid; isolating the product of said hydrolysation or esterification; and optionally converting said isolated product into a salt.

11. A process for preparing a compound of formula (I) according to claim 1, in which R denotes a C=$R_7$ radical and $R_7$ denotes a CH—$R_{19}$ radical in which $R_{19}$ denotes an —$NR_{25}R_{26}$ radical, said process comprising the steps of reacting a compound of formula (I) in which R denotes a —CH—$R_6$ radical and $R_6$ denotes a hydrogen atom with a HC(Rb)(Rc)Rd derivative in which either each of Rb and Rd, which are identical or different, denotes an —$NR_{25}R_{26}$ radical in which $R_{25}$ and $R_{26}$ have the same meanings as in claim 1 and Rc denotes an alkoxy radical, or each of Rb, Rc and Rd, which are identical, denotes an —$NR_{25}R_{26}$ radical in which $R_{25}$ and $R_{26}$ have the same meanings as in claim 1; isolating the product of said reaction; and optionally converting said isolated product into a salt.

12. A process for preparing a compound of formula (I) according to claim 1, in which R denotes a C=$R_7$ radical, $R_7$ denotes a $CHR_{19}$ radical and $R_{19}$ denotes a radical which is alkyl, optionally substituted phenyl, -alk-Het, phenylalkyl in which the phenyl nucleus is optionally substituted, —Het or -alk-$COOR_{10}$, said process comprising the steps of reacting a compound of formula (I) in which R denotes a CH—$R_6$ radical and $R_6$ denotes a hydrogen atom with an aldehyde of formula OHC—Re in which Re denotes a radical which is alkyl, phenyl optionally substituted by one or more substituents selected from halogen atoms, and alkyl, alkoxy, nitro, amino, hydroxyl, -alk-$NH_2$, —$COOR_{10}$, cyano and -alk-$COOR_{10}$ radicals, -alk-Het, phenylalkyl in which the phenyl nucleus is optionally substituted by one or more substituents selected from halogen atoms and alkyl, alkoxy, nitro, amino, hydroxyl, -alk-$NH_2$, —$COOR_{10}$, cyano and -alk-$COOR_{10}$ radicals, —Het or -alk-$COOR_{10}$ in which alk, Het and $R_{10}$ have the same meanings as in claim 1; isolating the product of said reaction; and optionally converting said isolated product into a salt.

13. A process for preparing a compound of formula (I) according to claim 1, in which R denotes a C=$R_7$ radical and $R_7$ denotes an $NR_{10}$ radical, said process comprising the steps of reacting ethyl trifluoroacetate with a derivative of formula:

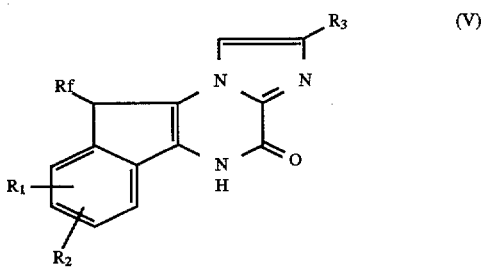

in which $R_1$, $R_2$ and $R_3$ have the same meanings as in claim 1 and Rf denotes an —$NH_2$ or —NH-alk radical, alk having the same meanings as in claim 1; isolating the product of said reaction; and optionally converting said isolated product into a salt.

14. A process for preparing a compound of formula (I) according to claim 1, in which R denotes a C=R₇ radical and R₇ denotes a C(COOR₁₀)R₂₀ radical, said process comprising the steps of dehydrating a compound of formula:

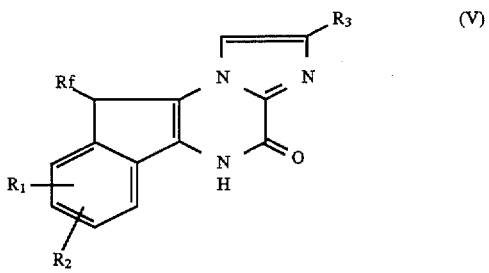

in which R₁, R₂ and R₃ have the same meanings as in claim 1 and Rf denotes a —C(R₂₀)(OH)—COOR₁₀ radical in which R₂₀ and R₁₀ have the same meanings as in claim 1; isolating the product of said dehydration; and optionally converting said isolated product into a salt.

15. A process for preparing a compound of formula (I) according to claim 1, in which R denotes a C=R₇ radical and R₇ denotes a C(CONR₁₀R₂₁)R₂₀ radical, said process comprising the steps of reacting a compound of formula (I) in which R denotes a C=R₇ radical and R₇ denotes a C(COOR₁₀)R₂₀ radical with an HNR₁₀R₂₁ amine in which R₁₀ and R₂₁ have the same meanings as in claim 1, isolating the product of said reaction; and optionally converting said isolated product into a salt.

16. A process for preparing a compound of formula (I) according to claim 1, in which R denotes a C(R₄)R₅ radical, R₄ denotes an alkyl, -alk-Het or phenylalkyl radical in which the phenyl nucleus is optionally substituted by one or more substituents selected from halogen atoms and alkyl, alkoxy, nitro, amino, hydroxyl, cyano, -alk-NH₂, —COOR₁₀ and -alk-COOR₁₀ radicals and R₅ is identical to R₄, said process comprising the steps of reacting a compound of formula (I) in which R denotes a CH—R₆ radical and R₆ denotes a hydrogen atom with a halide of formula Hal-Rg, in which Rg denotes an alkyl, -alk-Het or phenylalkyl radical in which the phenyl nucleus is optionally substituted by one or more substituents selected from halogen atoms and alkyl, alkoxy, nitro, amino, hydroxyl, cyano, -alk-NH₂, —COOR₁₀ and -alk-COOR₁₀ radicals, alk, Het and R₁₀ having the same meanings as in claim 1; isolating the product of said reaction; and optionally converting said isolated product into a salt.

17. A process for preparing a compound of formula (I) according to claim 1, in which R denotes a C(R₄)R₅ radical, R₄ denotes an alkyl, -alk-Het or phenylalkyl radical in which the phenyl nucleus is optionally substituted by one or more substituents selected from halogen atoms and alkyl, alkoxy, nitro, amino, hydroxyl, cyano, -alk-NH₂, —COOR₁₀ and -alk-COOR₁₀ radicals and R₅ denotes a radical selected from a 1–11 carbon atom alkyl having a straight or branched chain, -alk-CN, -alk-Het, -alk-NR₁₀R₁₈, -alk-CO—NR₁₀R₁₈ or phenylalkyl in which the phenyl nucleus is optionally substituted by one or more substituents selected from halogen atoms and alkyl, alkoxy, nitro, amino, hydroxyl, cyano, -alk-NH₂, —COOR₁₀ and -alk-COOR₁₀ radicals, said process comprising the steps of reacting a compound of formula (I) in which R denotes a CH—R₆ radical and R₆ denotes an alkyl, -alk-Het or phenylalkyl radical in which the phenyl nucleus is optionally substituted by one or more substituents selected from halogen atoms and alkyl, alkoxy, nitro, amino, hydroxyl, cyano, —COOR₁₀ and -alk-COOR₁₀ radicals with a halide Hal-Rh in which Rh denotes a radical which is alkyl having 1 to 11 carbon atoms in a straight or branched chain, -alk-Het, -alk-CN, -alk-NR₁₀R₁₈, -alk-CO—NR₁₀R₁₈ or phenylalkyl radical in which the phenyl nucleus is optionally substituted by one or more substituents selected from halogen atoms and alkyl, alkoxy, nitro, amino, hydroxyl, cyano, -alk-NH₂, —COOR₁₀ and -alk-COOR₁₀ radicals, alk, Het, R₁₀ and R₁₈ having the same meanings as in claim 1; isolating the product of said reaction; and optionally converting said isolated product into a salt.

18. A process for preparing a compound of formula (I) according to claim 1, in which R denotes a C(R₄)R₅ radical and R₄ and R₅ form, with the carbon atom to which they are attached, a cycloalkyl radical, said process comprising the steps of reacting a compound of formula (I) in which R denotes a CH—R₆ radical and R₆ denotes a hydrogen atom with a derivative of formula Hal-alk-Hal in which Hal denotes a halogen atom and alk denotes an alkyl radical having 2 to 5 carbon atoms; isolating the product of said reaction; and optionally converting said isolated product into a salt.

19. A process for preparing a compound of formula (I) according to claim 1, in which R denotes a C(R₄)R₅ radical in which R₅ denotes an —NR₈R₉ radical and R₈ and R₉ denote hydrogen atoms, said process comprising the steps of reacting a halide Hal-R₄ in which Hal denotes a halogen atom and R₄ has the same meanings as in claim 1 with a compound of formula (I) in which R denotes a CH—R₆ radical, R₆ denotes an —NR₁₄R₁₅ radical, R₁₄ denotes a hydrogen atom, R₁₅ denotes a —COR₂₂ radical and R₂₂ denotes an alkyl radical having one carbon atom; hydrolysing the product of said reaction; isolating said hydrolysed product; and optionally converting said isolated product into a salt.

20. A process for preparing a compound of formula (I) according to claim 1, in which R denotes a C(R₄)R₅ radical in which R₅ denotes an —NR₈R₉ radical, R₉ denotes a hydrogen atom and R₈ denotes an alkyl, -alk-COOR₁₀, -alk-NR₁₀R₂₁, -alk-Het or phenylalkyl radical in which the phenyl nucleus is optionally substituted, said process comprising the steps of reacting a compound of formula (I) in which R denotes a C(R₄)R₅ radical, R₅ denotes an —NR₈R₉ radical and R₈ and R₉ denote hydrogen atoms is reacted with a halide Hal-R₈ in which R₈ has the same meanings as above; isolating the product of said reaction; and optionally converting said isolated product into a salt.

21. A process for preparing a compound of formula (I) according to claim 1, in which R denotes a C(R₄)R₅ radical in which R₅ denotes an —NR₈R₉ radical, R₉ denotes a hydrogen atom or an alkyl radical and R₈ denotes an alkyl radical having 2 to 6 carbon atoms, said process comprising the steps of reacting a compound of formula (I) in which R denotes a C(R₄)R₅ radical, R₅ denotes an —NR₈R₉ radical, R₉ denotes a hydrogen atom or an alkyl radical and R₈ denotes a hydrogen atom with an acyl halide having 2 to 6 carbon atoms; reducing the product of said reaction; isolating said reduced product; and optionally converting said isolated product into a salt.

22. A process for preparing a compound of formula (I) according to claim 1, in which R denotes a C(R₄)R₅ radical in which R₅ denotes an —NR₈R₉ radical and R₉ denotes an alkyl radical, said process comprising the steps of reacting a compound of formula (I) in which R denotes a C(R₄)R₅ radical, R₅ denotes an —NR₈R₉ radical, R₈ has the same meanings as in claim 1 and R₉ denotes a hydrogen atom, with a derivative of the formula Hal-alk in which Hal denotes a halogen atom and alk denotes an alkyl radical; isolating the product of said reaction; and optionally converting said isolated product into a salt.

23. A process for preparing a compound of formula (I) according to claim 1, in which R denotes a C(R₄)R₅ radical in which R₅ denotes an —NR₈R₉ radical, R₉ denotes a hydrogen atom or an alkyl radical and R₈ denotes a —(2–6 C)alk-NR₁₀R₂₁ radical, said process comprising the steps of reducing a derivative of formula:

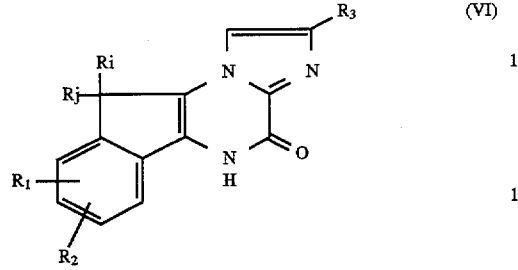

in which R₁, R₂ and R₃ have the same meanings as in formula (I), Ri denotes a radical which is alkyl, phenylalkyl in which the phenyl nucleus is optionally substituted by one or more substituents selected from halogen atoms and alkyl, alkoxy, nitro, amino, hydroxyl, cyano, -alk-NH₂, —COOR₁₀ and -alk-COOR₁₀ or -alk-Het and Rj denotes an —NH—CO—(1–5 C)alk-NR₁₀R₂₁ or —N(alk)-CO—(1–5 C)alk-NR₁₀R₂₁ radical in which alk, Het, R₁₀ and R₂₁ have the same meanings as in claim 1; isolating the product of said reduction; and optionally converting said isolated product into a salt.

24. A process for preparing a compound of formula (I) according to claim 1, in which R denotes a C(R₄)R₅ radical in which R₅ denotes a —COOR₁₀ radical and R₁₀ denotes a hydrogen atom, said process comprising the steps of hydrolysing a compound of formula (I) in which R denotes a C(R₄)R₅ radical in which R₅ denotes a —COOR₁₀ radical and R₁₀ denotes an alkyl radical; isolating the product of said hydrolysation; and optionally converting said isolated product into a salt.

25. A process for preparing a compound of formula (I) according to claim 1, in which R denotes a C(R₄)R₅ radical in which R₅ denotes a —COOR₁₀ radical and R₁₀ denotes an alkyl radical, said process comprising the steps of reacting a compound of formula (I) in which R denotes a CH—R₆ radical and R₆ denotes an alkyl, -alk-Het or optionally substituted phenylalkyl radical, with a halide of formula Hal-COOR₁₀ in which R₁₀ denotes an alkyl radical and Hal denotes a halogen atom; isolating the product of said reaction; and optionally converting said isolated product into a salt.

26. A process for preparing a compound of formula (I) according to claim 1, in which R denotes a C(R₄)R₅ radical in which R₅ denotes an -alk-COOR₁₀ radical, said process comprising the steps of reacting a compound of formula (I) in which R denotes a CH—R₆ radical, R₆ denotes an -alk-COOR₁₀ radical and R₁₀ has the same meanings as in claim 1, with a halide Hal-R₄ in which R₄ has the same meanings as in claim 1; isolating the product of said reaction; and optionally converting said isolated product into a salt.

27. A process for preparing a compound of formula (I) according to claim 1, in which R denotes a C(R₄)R₅ radical in which R₅ denotes an -alk-CN radical in which alk contains 1 carbon atom, said process comprising the steps of reacting sodium cyanide with a derivative of formula:

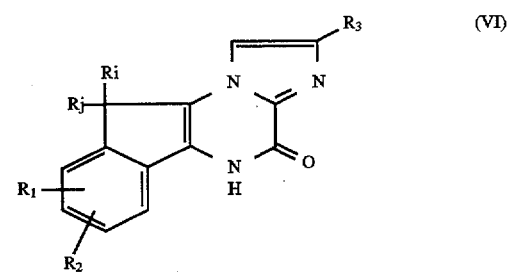

in which R₁, R₂ and R₃ have the same meanings as in claim 1, Ri denotes a —CH₂OTs radical in which Ts denotes a tosylate residue and Rj denotes an alkyl, -alk-Het or phenylalkyl radical in which the phenyl nucleus is optionally substituted by one or more substituents selected from halogen atoms and alkyl, alkoxy, nitro, amino, hydroxyl, cyano, -alk-NH₂, —COOR₁₀ and -alk-COOR₁₀ radicals, alk, Het and R₁₀ having the same meanings as in claim 1; isolating the product of said reaction; and optionally converting said isolated product into a salt.

28. A process for preparing a compound of formula (I) according to claim 1, in which R denotes a C(R₄)R₅ radical in which R₅ denotes a —(2–8 C)alkOH radical, said process comprising the steps of reacting (COCl)₂ with a compound of formula (I) in which R denotes a C(R₄)R₅ radical in which R₅ denotes an -alk-COOR₁₀ radical and R₁₀ denotes a hydrogen atom; reducing the product of said reaction; isolating the product of said reduction; and optionally converting the isolated product into a salt.

29. A process for preparing a compound of formula (I) according to claim 1, in which R denotes a C(R₄)R₅ radical in which R₅ denotes a —(1 C)alkOH radical, said process comprising the steps of reacting a derivative of formula:

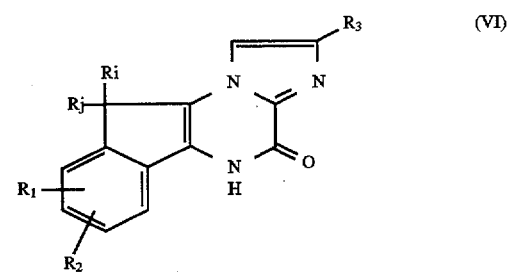

in which R₁, R₂ and R₃ have the same meanings as in claim 1, Ri denotes a hydrogen atom and Rj denotes an alkyl, -alk-Het or phenylalkyl radical in which the phenyl nucleus is optionally substituted by one or more substituents selected from halogen atoms and alkyl, alkoxy, nitro, amino, hydroxyl, cyano, -alk-NH₂, —COOR₁₀ and -alk-COOR₁₀ radicals, alk, Het and R₁₀ having the same meanings as in claim 1; with trimethylsilane chloride; then reacting with trioxane; isolating said reaction product; and optionally converting said isolated product into a salt.

30. A process for preparing a compound of formula (I) according to claim 1, in which R denotes a C(R₄)R₅ radical in which R₅ denotes an —NH—CHO radical, said process comprising the steps of reacting a derivative of formula:

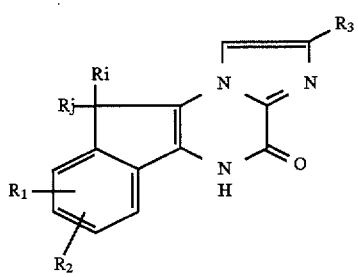

(VI)

in which $R_1$, $R_2$ and $R_3$ have the same meanings as in claim 1, Ri denotes an alkyl, -alk-Het or phenylalkyl radical in which the phenyl nucleus is optionally substituted by one or more substituents selected from halogen atoms and alkyl, alkoxy, nitro, amino, hydroxyl, cyano, -alk-$NH_2$, —$COOR_{10}$ and -alk-$COOR_{10}$ radicals and Rj denotes an amino radical, alk, Het and $R_{10}$ having the same meanings as in claim 1, with $CH_3COOCHO$; isolating the product of said reaction; and optionally converting said isolated product into a salt.

31. A process for preparing a compound of formula (I) according to claim 1, in which R denotes a $C(R_4)R_5$ radical in which $R_5$ denotes a radical which is —NH—$COOR_{17}$, —NH—CO—Het, —NH—CO-alk-$COOR_{10}$, —NH—CO-alk-$NR_{10}R_{18}$, —NH—CO—Ar in which Ar is optionally substituted, —NH—CO-alk-Ar in which Ar is optionally substituted, —NH—$SO_2$—$R_{24}$, —NH—CO-alk-Het, —NH—CO-alk or —NH—CO-cycloalkyl, said process comprising the steps of reacting a compound of formula (I) in which R denotes a $C(R_4)R_5$ radical, $R_5$ denotes an —$NR_8R_9$ radical and $R_8$ and $R_9$ denote hydrogen atoms with a Hal-Rk derivative in which Hal denotes a halogen atom and Rk denotes a radical which is —$COOR_{17}$, —CO—Het, —CO-alk-$COOR_{10}$, —CO-alk-$NR_{10}R_{18}$, —CO-alk-Ar in which Ar is optionally substituted by one or more substituents selected from halogen atoms and alkyl, alkoxy, nitro, amino, hydroxyl, cyano, -alk-$NH_2$, —$COOR_{10}$ and -alk-$COOR_{10}$ radicals, —$SO_2$—$R_{24}$, —CO-alk-Het, —CO—Ar in which Ar is optionally substituted by one or more substituents selected from halogen atoms and alkyl, alkoxy, nitro, amino, hydroxyl, cyano,-alk-$NH_2$, —$COOR_{10}$ and -alk-$COOR_{10}$, —CO-alk or —CO-cycloalkyl radicals, $R_7$, $R_{10}$, $R_{17}$, $R_{18}$, $R_{24}$, Het, Ar and alk having the same meanings as in claim 1; isolating the product of said reaction; and optionally converting said isolated product into a salt.

32. A process for preparing a compound of formula (I) according to claim 1, in which R denotes a $C(R_4)R_5$ radical in which $R_5$ denotes a radical which is —NH—CO—Het, —NH—CO-alk-$COOR_{10}$, —NH—CO-alk-$NR_{10}R_{18}$, —NH—CO—Ar in which Ar is optionally substituted, —NH—CO-alk-Ar in which Ar is optionally substituted, —NH—CO-alk-Het, —NH—CO-alk or —NH—CO-cycloalkyl, said process comprising the steps of reacting a compound of formula (I) in which R denotes a $C(R_4)R_5$ radical, $R_5$ denotes an —$NR_8R_9$ radical and $R_8$ and $R_9$ denote hydrogen atoms, with a derivative HO—Rl in which Rl denotes a radical which is —CO—Het, —CO-alk-$COOR_{10}$, —CO-alk-$NR_{10}R_{18}$, —CO-alk-Ar in which Ar is optionally substituted by one or more substituents selected from halogen atoms and alkyl, alkoxy, nitro, amino, hydroxyl, cyano, -alk-$NH_2$, —$COOR_{10}$ and -alk-$COOR_{10}$ radicals, —CO-alk-Het, —CO—Ar in which Ar is optionally substituted by one or more substituents selected from halogen atoms and alkyl, alkoxy, nitro, amino, hydroxyl, cyano, -alk-$NH_2$, —$COOR_{10}$ and -alk-$COOR_{10}$, —CO-alk or —CO-cycloalkyl radicals, $R_{10}$, $R_{18}$, Het, Ar and alk having the same meanings as in claim 1; isolating the product of said reaction; and optionally converting said isolated product into a salt.

33. A process for preparing a compound of formula (I) according to claim 1, in which R denotes a $C(R_4)R_5$ radical in which $R_5$ denotes a 1-pyrrolyl radical optionally substituted by a —$COOR_{10}$ radical, said process comprising the steps of reacting a derivative of formula:

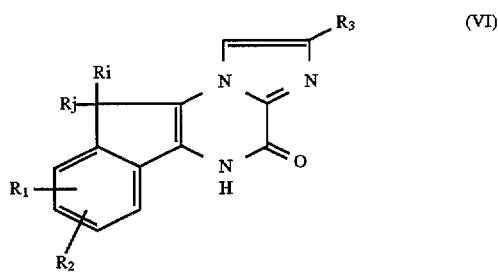

(VI)

in which $R_1$, $R_2$ and $R_3$ have the same meanings as in claim 1, Ri denotes an alkyl, -alk-Het or phenylalkyl radical in which the phenyl nucleus is optionally substituted by one or more substituents selected from halogen atoms and alkyl, alkoxy, nitro, amino, hydroxyl, cyano, -alk-$NH_2$, —$COOR_{10}$ and -alk-$COOR_{10}$ radicals, alk, Het and $R_{10}$ having the same meanings as in formula (I) and Rj denotes an amino radical, with a derivative of formula:

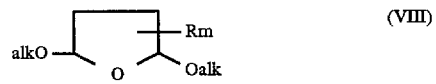

(VIII)

in which Rm denotes a hydrogen atom or a —$COOR_{10}$ radical and alk and $R_{10}$ have the same meanings as in claim 1; isolating the product of said reaction; and optionally converting said isolated product into a salt.

34. A process for preparing a compound of formula (I) according to claim 1, in which R denotes a $C(R_4)R_5$ radical in which $R_5$ denotes a radical which is —NH—CO—NH-alk-Ar in which Ar is optionally substituted, —NH—CO—NH—Het, —NH—CO—NH-alk-Het, —NH—CO—NH—Ar in which Ar is optionally substituted, —NH—CO—NH-alk or —NH—CO—$NH_2$, said process comprising the steps of reacting a compound of formula (I) in which R denotes a $C(R_4)R_5$ radical, $R_5$ denotes an —$NR_8R_9$ radical and $R_8$ and $R_9$ denote hydrogen atoms, with a derivative O=C=N—Rn in which Rn denotes a radical which is trimethylsilyl, alkyl, —Het, -alk-Ar in which Ar is optionally substituted by one or more substituents selected from halogen atoms and alkyl, alkoxy, nitro, amino, hydroxyl, cyano, -alk-$NH_2$, —$COOR_{10}$ and -alk-$COOR_{10}$ radicals, -alk-Het or phenyl optionally substituted by one or more substituents selected from halogen atoms and alkyl, alkoxy, nitro, amino, hydroxyl, cyano, -alk-$NH_2$, —$COOR_{10}$ and -alk-$COOR_{10}$ radicals in which $R_{10}$, alk, Ar and Het have the same meanings as in claim 1; isolating the product of said reaction; and optionally converting said isolated product into a salt.

35. A process for preparing a compound of formula (I) according to claim 1, in which R denotes a CH—$R_6$ radical in which $R_6$ denotes a hydroxyl radical, said process comprising the steps of reducing a compound of formula (I) in which R denotes a C=$R_7$ radical and $R_7$ denotes an oxygen atom; isolating the product of said reduction; and optionally converting said isolated product into a salt.

36. A process for preparing a compound of formula (I) according to claim 1, in which R denotes a CH—$R_6$ radical in which R₆ denotes an alkyl having 2 to 11 carbon atoms or a phenylalkyl radical in which the phenyl nucleus is optionally substituted by one or more substituents selected from halogen atoms and alkyl, alkoxy, nitro, amino, hydroxyl, cyano, -alk-NH₂, —COOR₁₀ and -alk-COOR₁₀ or -alk-Het radicals, said process comprising the steps of hydrogenating a derivative of formula:

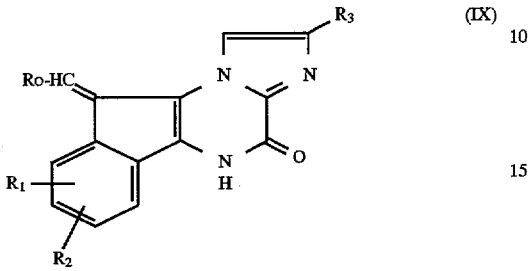
(IX)

in which R₁, R₂ and R₃ have the same meanings as in claim 1, Ro denotes a radical which is alkyl as a straight or branched chain containing 1 to 10 carbon atoms, phenyl, phenyl(1–5 C)alkyl in which the phenyl nucleus is optionally substituted by one or more substituents selected from halogen atoms and alkyl, alkoxy, nitro, amino, hydroxyl, cyano, -alk-NH₂, —COOR₁₀ and -alk-COOR₁₀ radicals, —Het or —(1–5 C)alk-Het in which alk, Het and R₁₀ have the same meanings as in claim 1; isolating the product of said hydrogenation; and optionally converting said isolated product into a salt.

37. A process for preparing a compound of formula (I) according to claim 1, in which R denotes a CH—R₆ radical in which R₆ denotes an optionally substituted phenylalkyl or -alk-Het radical, said process comprising the steps of reacting a compound of formula (I) in which R denotes a CH—R₆ radical and R₆ denotes a hydrogen atom, with a halide of the formula Hal-Rp in which Rp denotes a phenylalkyl radical in which the phenyl nucleus is optionally substituted by one or more substituents selected from halogen atoms and alkyl, alkoxy, nitro, amino, hydroxyl, cyano, -alk-NH₂, —COOR₁₀ and -alk-COOR₁₀ or-alk-Het radicals in which alk, Het and R₁₀ have the same meanings as in claim 1; isolating the product of said reaction; and optionally converting said isolated product into a salt.

38. A process for preparing a compound of formula (I) according to claim 1, in which R denotes a CH—R₆ radical in which R₆ denotes an alkyl radical having one carbon atom, said process comprising the steps of reducing a compound of formula (I) in which R denotes a C=R₇ radical, R₇ denotes a CH—R₁₉ radical and R₁₉ denotes a hydroxyl or —NR₂₅R₂₆ radical; isolating the product of said reaction; and optionally converting said isolated product into a salt.

39. A process for preparing a compound of formula (I) according to claim 1, in which R denotes a CHR₆ radical and R₆ denotes a —(1 C)alk-OH radical, said process comprising the steps of reducing a compound of formula (I) in which R denotes a C=R₇ radical, R₇ denotes a CH—R₁₉ radical and R₁₉ denotes a hydroxyl radical; isolating the product of said reaction; and optionally converting said isolated product into a salt.

40. A process for preparing a compound of formula (I) according to claim 1, in which R denotes a CHR₆ radical and R₆ denotes a —(2–6 C)alk-OH radical, said process comprising the steps of reducing a derivative of formula:

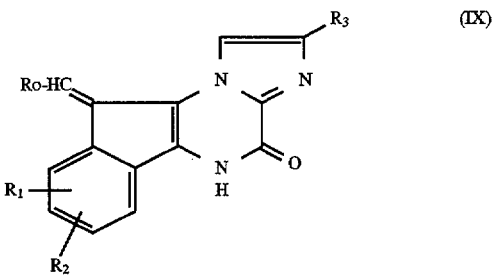
(IX)

in which R₁, R₂ and R₃ have the same meanings as in claim 1 and Ro denotes a —(1–5 C)alk-O—CH₂—Ar radical, alk and Ar having the same meanings as in claim 1; isolating the product of said reduction; and optionally converting said isolated product into a salt.

41. A process for preparing a compound of formula (I) according to claim 1, in which R denotes a CH—R₆ radical in which R₆ denotes an —NR₁₄R₁₅ radical and each of R₁₄ and R₁₅ denotes a hydrogen atom, said process comprising the steps of hydrolysing a compound of formula (I) in which R denotes a CH—R₆ radical in which R₆ denotes an —NR₁₄R₁₅ radical, R₁₄ denotes a hydrogen atom, R₁₅ denotes a —COR₂₂ radical and R₂₂ denotes an alkyl radical; then, for compounds in which R₃ denotes an alkoxycarbonyl radical, esterifying the corresponding acid; isolating the product of said hydrolysation or esterification; and optionally converting said isolated product into a salt.

42. A process for preparing a compound of formula (I) according to claim 1, in which R denotes a CH—R₆ radical in which R₆ denotes an —NR₁₄R₁₅ radical, R₁₄ denotes a hydrogen atom, R₁₅ denotes a —COR₂₂ radical and R₂₂ denotes an alkyl radical, said process comprising the steps of reacting a reducing agent, and then an acid anhydride (alkCO)₂O in which alk denotes an alkyl radical, with a compound of formula (I) in which R denotes a C=R₇ radical and R₇ denotes an NOH radical; isolating the product of said reactions; and optionally converting said isolated product into a salt.

43. A process for preparing a compound of formula (I) according to claim 1, in which R denotes a CH—R₆ radical and R₆ denotes an —NR₁₄R₁₅ or -alk-NR₁₄R₁₅ radical, in which each of R₁₄ and R₁₅, which are identical or different, denotes an alkyl radical or, alternatively, R₁₄ denotes a hydrogen atom and R₁₅ denotes an alkyl, —COR₂₂ or —SO₂R₂₄ radical, R₂₂ denotes a radical which is alkyl, cycloalkyl, —COOalk, -alk-COOR₁₀, phenyl optionally substituted by one or more substituents selected from halogen atoms and alkyl, alkoxy, nitro, amino, hydroxyl, -alk-NH₂, —COOR₁₀, cyano and -alk-COOR₁₀ radicals, phenylalkyl in which the phenyl nucleus is optionally substituted by one or more substituents selected from halogen atoms and alkyl, alkoxy, nitro, amino, hydroxyl, -alk-NH₂, —COOR₁₀, cyano and -alk-COOR₁₀ radicals, —OR₁₇, —Het, -alk-Het, -alk-NR₁₀R₁₂ and R₂₄ denotes an alkyl or phenyl radical, said process comprising the steps of reacting a compound of formula (I) in which each of R₁₄ and R₁₅ denotes a hydrogen atom, with a halide of formula Hal-Rr in which Rr denotes an alkyl, —COR₂₂ or —SO₂R₂₄ radical, R₂₂ denotes a radical which is alkyl, cycloalkyl, —COOalk, -alk-COOR₁₀, phenyl optionally substituted by one or more substituents selected from halogen atoms and alkyl, alkoxy, nitro, amino, hydroxyl, -alk-NH₂, —COOR₁₀, cyano and -alk-COOR₁₀ radicals, phenylalkyl in which the phenyl nucleus is optionally substituted by one or more substituents selected from halogen atoms and alkyl, alkoxy, nitro, amino, hydroxyl, -alk-NH₂, —COOR₁₀, cyano and -alk-COOR₁₀ radicals, —OR$_{17}$, —Het or -alk-Het, -alk-NR$_{10}$R$_{12}$ and R$_{24}$ denotes an alkyl or phenyl radical, alk, Het, R$_{12}$, R$_{17}$ and R$_{10}$ having the same meanings as in claim 1; isolating the product of said reaction; and optionally converting said isolated product into a salt.

44. A process for preparing a compound of formula (I) according to claim 1, in which R denotes a CH—R$_6$ radical and R$_6$ denotes an —NR$_{14}$R$_{15}$ or -alk-NR$_{14}$R$_{15}$ radical in which R$_{14}$ denotes a hydrogen atom, R$_{15}$ denotes a —COR$_{22}$ or —CSR$_{23}$ radical, R$_{22}$ denotes a radical which is —NH-alk, —NH$_2$, —NH—Ar in which Ar is optionally substituted, —NH-alk-Ar in which Ar is optionally substituted, —NH-alk-Het or —NH—Het and R$_{23}$ denotes an —NH-alk, —NH$_2$, —NH—Ar or —NH—Het radical, said process comprising the steps of reacting a compound of formula (I) in which R denotes a CH—R$_6$ radical, R$_6$ denotes an —NR$_{14}$R$_{15}$ radical and each of R$_{14}$ and R$_{15}$ denotes a hydrogen atom, with a Rs—N=C=Rt derivative in which Rs denotes a radical which is trimethylsilyl, alkyl, phenyl optionally substituted by one or more substituents selected from halogen atoms and alkyl, alkoxy, nitro, amino, hydroxyl, cyano, -alk-NH$_2$, —COOR$_{10}$ and -alk-COOR$_{10}$ radicals, -alk-Ar in which Ar is optionally substituted by one or more substituents selected from halogen atoms and alkyl, alkoxy, nitro, amino, hydroxyl, cyano,-alk-NH$_2$, —COOR$_{10}$ and-alk-COOR$_{10}$ radicals, -alk-Het or —Het in which Het, alk, R$_{10}$ and Ar have the same meanings as in claim 1 and Rt denotes an oxygen or sulphur atom; optionally following said reaction by a hydrolysis step; isolating the product of said reaction and/or hydrolysis; and optionally converting said isolated product into a salt.

45. A process for preparing a compound of formula (I) according to claim 1, in which R denotes a CH—R$_6$ radical and R$_6$ denotes an —NR$_{14}$R$_{15}$ or -alk-NR$_{14}$R$_{15}$ radical in which R$_{14}$ denotes a hydrogen atom, R$_{15}$ denotes a —COR$_{22}$ radical and R$_{22}$ denotes a —(1 C)alk-NR$_{10}$R$_{12}$ radical in which R$_{10}$ and R$_{12}$ are hydrogen atoms, said process comprising the steps of reacting a compound of formula (I) in which each of R$_{14}$ and R$_{15}$ denotes a hydrogen atom, with an acid HOOC—CH$_2$—NH—Ru in which Ru denotes a protecting group for the amine functional group; hydrolysing the product of said reaction; isolating the product of said hydrolysis; and optionally converting said isolated product into a salt.

46. A process for preparing a compound of formula (I) according to claim 1, in which R denotes a CH—R$_6$ radical, R$_6$ denotes an -alk-NR$_{14}$R$_{15}$ radical and each of R$_{14}$ and R$_{15}$ denotes a hydrogen atom with the exception of those in which R$_3$ denotes a carboxamido radical, said process comprising the steps of reacting bromine and sodium hydroxide with a compound of formula (I) in which R denotes a CH—R$_6$ radical, R$_6$ denotes an -alk-CONR$_{10}$R$_{21}$ radical and R$_{10}$ and R$_{21}$ denote hydrogen atoms; isolating the product of said reaction; and optionally converting said isolated product into a salt.

47. A process for preparing a compound of formula (I) according to claim 1, in which R denotes a CH—R$_6$ radical, R$_6$ denotes an -alk-NR$_{14}$R$_{15}$ radical, each of R$_{14}$ and R$_{15}$ denotes a hydrogen atom and R$_3$ denotes a carboxamido radical, said process comprising the steps of reacting ammonia with a compound of formula (I) in which R denotes a CH—R$_6$ radical, R$_6$ denotes an -alk-NR$_{14}$R$_{15}$ radical, each of R$_{14}$ and R$_{15}$ denotes a hydrogen atom and R$_3$ denotes an alkoxycarbonyl radical; isolating the product of said reaction; and optionally converting said isolated product into a salt.

48. A process for preparing a compound of formula (I) according to claim 1, in which R denotes a CH—R$_6$ radical, R$_6$ denotes an —NR$_{14}$R$_{15}$ or -alk-NR$_{14}$R$_{15}$ radical in which R$_{14}$ denotes a hydrogen atom and R$_{15}$ denotes a —COR$_{22}$ radical, R$_{22}$ denotes a radical which is alkyl, cycloalkyl, -alk-COOR$_{10}$, optionally substituted phenyl, phenylalkyl in which the phenyl is optionally substituted, Het, -alk-Het or -alk-NR$_{10}$R$_{12}$, said process comprising the steps of reacting a compound of formula (I) in which R denotes a CH—R$_6$ radical, R$_6$ denotes an —NR$_{14}$R$_{15}$ radical, R$_{14}$ denotes a hydrogen atom and R$_{15}$ denotes a hydrogen atom, with an acid HOOC—R$_{22}$ in which R$_{22}$ denotes a radical which is alkyl, cycloalkyl, —Het, -alk-COOR$_{10}$, -alk-NR$_{10}$R$_{12}$, phenylalkyl in which the phenyl is optionally substituted by one or more substituents selected from halogen atoms and alkyl, alkoxy, nitro, amino, hydroxyl, cyano, -alk-NH$_2$, —COOR$_{10}$ and -alk-COOR$_{10}$ radicals, -alk-Het, phenyl optionally substituted by one or more substituents selected from halogen atoms and alkyl, alkoxy, nitro, amino, hydroxyl, cyano, -alk-NH$_2$, —COOR$_{10}$ and -alk-COOR$_{10}$, alk, Het, R$_{10}$ and R$_{12}$ having the same meanings as in claim 1 or the corresponding anhydride; isolating the product of said reaction; and optionally converting said isolated product into a salt.

49. A process for preparing a compound of formula (I) according to claim 1, in which R denotes a CH—R$_6$ radical and R$_6$ denotes an -alk-COOR$_{10}$ radical, said process comprising the steps of hydrogenating a corresponding derivative of formula:

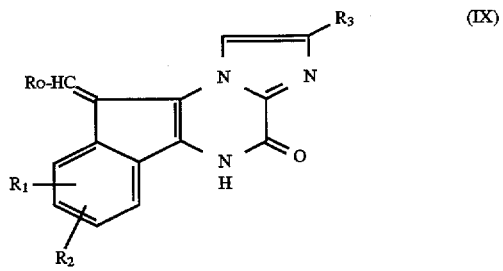

in which R$_1$, R$_2$ and R$_3$ have the same meanings as in claim 1 and Ro denotes a —(1–5 C)alk-COOR$_{10}$ or —COOR$_{10}$ radical, in which alk has the same meanings as in claim 1, R$_{10}$ denotes an alkyl or phenylalkyl radical; optionally following said hydrogenation by a saponification of the ester obtained; isolating the product of said hydrogenation and/or saponification; and optionally converting said isolated product into a salt.

50. A process for preparing a compound of formula (I) according to claim 1, in which R denotes a CH—R$_6$ radical and R$_6$ denotes an -alk-CO—NR$_{10}$R$_{21}$ radical, said process comprising the steps of reacting a compound of formula (I) in which R denotes a CH—R$_6$ radical and R$_6$ denotes an -alk-COOR$_{10}$ radical, alk having the same meanings as in claim 1, and R$_{10}$ denotes a hydrogen atom or an alkyl radical, with an amine HNR$_{10}$R$_{21}$ in which R$_{10}$ and R$_{21}$ have the same meanings as in claim 1; isolating the product of said reaction; and optionally converting said isolated product into a salt.

51. A process for preparing a compound of formula (I) according to claim 1, in which R denotes a CH—R$_6$ radical, R$_6$ denotes a —(C 1)alk-CO—NR$_{10}$R$_{21}$ radical and R$_{10}$ and R$_{21}$ denote hydrogen atoms, said process comprising the steps of hydrogenating a derivative of formula:

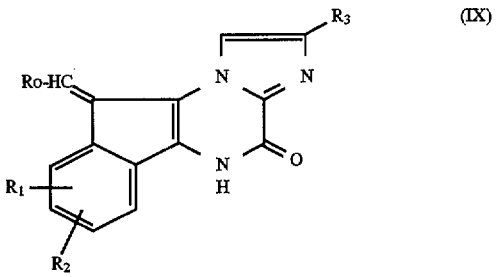

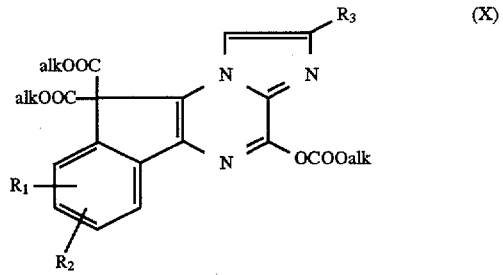

in which $R_1$, $R_2$ and $R_3$ have the same meanings as in formula (I) and Ro denotes a —$CONH_2$ radical; isolating the product of said hydrogenation; and optionally converting said isolated product into a salt.

52. A process for preparing a compound of formula (I) according to claim 1, in which R denotes a CH—$R_6$ radical and $R_6$ denotes an —$R_{16}$—$COOR_{10}$ radical, said process comprising the steps of reacting a compound of formula (I) in which R denotes a CH—$R_6$ radical and $R_6$ denotes a hydrogen atom, with a derivative of formula OHC—(0–5 C)alk-$COOR_{10}$ in which alk and $R_{10}$ have the same meanings as in claim 1; isolating the product of said reaction; and optionally converting said isolated product into a salt.

53. A process for preparing a compound of formula (I) according to claim 1, in which R denotes a CH—$R_6$ radical and $R_6$ denotes an —NH—CHO radical, said process comprising the steps of reacting a compound of formula (I) in which R denotes a CH—$R_6$ radical, $R_6$ denotes an —$NR_{14}R_{15}$ radical and $R_{14}$ and $R_{15}$ denote hydrogen atoms with $CH_3COOCHO$; isolating the product of said reaction; and optionally converting said isolated product into a salt.

54. A process for preparing a compound of formula (I) according to claim 1, in which R denotes a CH—$R_6$ radical and $R_6$ denotes a —CO—$COOR_{10}$ radical, said process comprising the steps of oxidizing a compound of formula (I) in which R denotes a CH—$R_6$ radical, $R_6$ denotes a —$R_{16}$—$COOR_{10}$ radical and $R_{16}$ denotes a —CHOH— radical; optionally following said oxidation by an esterification; isolating the product of said oxidation and/or esterification; and optionally converting said isolated product into a salt.

55. A process for preparing a compound of formula (I) according to claim 1, in which R denotes a CH—$R_6$ radical and $R_6$ denotes a 1-pyrrolyl radical optionally substituted by a —$COOR_{10}$ radical, said process comprising the steps of reacting a compound of formula (I) in which R denotes a CH—$R_6$ radical and $R_6$ denotes an —$NR_{14}R_{15}$ radical and $R_{14}$ and $R_{15}$ denote hydrogen atoms, with a derivative of formula:

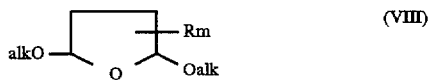

(VIII)

in which Rm denotes a hydrogen atom or a —$COOR_{10}$ radical, $R_{10}$ having the same meanings as in claim 1; isolating the product of said reaction; and optionally converting said isolated product into a salt.

56. A process for preparing a compound of formula (I) according to claim 1, in which R denotes a CH—$R_6$ radical and $R_6$ denotes a —COOalk radical, said process comprising the steps of reacting an inorganic acid with a derivative of formula:

in which $R_1$, $R_2$ and $R_3$ have the same meanings as in claim 1 and alk denotes an alkyl radical; isolating the product of said reaction; and optionally converting said isolated product into a salt.

57. A process for preparing a compound of formula (I) according to claim 1, in which $R_3$ denotes a carboxyl radical, said process comprising the steps of hydrolysing a compound of formula (I) in which $R_3$ denotes an alkoxycarbonyl radical; isolating the product is of said hydrolysis; and optionally converting said isolated product into a salt.

58. A process for preparing a compound of formula (I) according to claim 1, in which $R_1$ and/or $R_2$ denote an —NH—CO—$NR_{11}R_{12}$ radical in which $R_{11}$ denotes a hydrogen atom or a radical which is alkyl having 1 to 9 carbon atoms in a straight or branched chain, -alk-$COOR_{10}$, -alk-Het, -alk-$NR_{12}R_{10}$, phenylalkyl in which the phenyl nucleus is optionally substituted by one or more substituents selected from halogen atoms and alkyl, alkoxy, nitro, amino, hydroxyl, -alk-$NH_2$, carboxyl, alkoxycarbonyl, cyano and -alk-$COOR_{10}$ radicals, phenyl optionally substituted by one or more substituents selected from halogen atoms and alkyl, alkoxy, nitro, amino, hydroxyl, -alk-$NH_2$, carboxyl, alkoxycarbonyl, cyano and -alk-$COOR_{10}$ radicals or —Het and $R_{12}$ denotes a hydrogen atom, said process comprising the steps of reacting a compound of formula (I) in which $R_1$ and/or $R_2$ denotes an amino radical with an isocyanate O=C=$NR_{11}$ in which $R_{11}$ has the same meanings as above or denotes a trimethylsilyl radical; isolating the product of said reaction; and optionally converting said isolated product into a salt.

59. A process for preparing a compound of formula (I) according to claim 1, in which $R_1$ and/or $R_2$ denote an amino radical, said process comprising the steps of reducing a compound of formula (I) in which $R_1$ and/or $R_2$ denote a nitro radical; isolating the product of said reduction; and optionally converting said isolated product into a salt.

60. A process for preparing a compound of formula (I) according to claim 1, in which R denotes a CH—$R_6$ radical, $R_6$ denotes an —$NR_{14}R_{15}$ radical and $R_{14}$ and $R_{15}$ denote hydrogen atoms, said process comprising the steps of reducing a compound of formula (I) in which R denotes a C=$R_7$ radical and $R_7$ denotes an NOH radical, in the presence of a reducing agent; isolating the product of said reduction; and optionally converting said isolated product into a salt.

61. A process for preparing a compound of formula (I) according to claim 1, in which R denotes a C=$R_7$ radical, $R_7$ denotes a CH—$R_{19}$ radical, $R_{19}$ denotes a phenyl radical substituted by a —$COOR_{10}$ radical and $R_{10}$ denotes a hydrogen atom, said process comprising the steps of hydrolysing a compound of formula (I) in which R denotes a C=$R_7$ radical, $R_7$ denotes a CH—$R_{19}$ radical and $R_{19}$ denotes a phenyl radical substituted by a cyano radical; isolating the product of said hydrolysis; and optionally converting said isolated product into a salt.

62. A process for preparing a compound of formula (I) according to claim 1, in which R denotes a CH—$R_6$ radical and $R_6$ denotes a 2-oxo-2,5-dihydro-pyrrol-1-yl radical, said process comprising the steps of reacting a compound of formula (I) in which R denotes a CH—$R_6$ radical, $R_6$ denotes an —$NR_{14}R_{15}$ radical and $R_{14}$ and $R_{15}$ denote hydrogen atoms with 2,5-dimethoxy-2,5-dihydrofuran; isolating the product of said reaction; and optionally converting said isolated product into a salt.

63. A compound of formula (I) according to claim 1, in which R denotes a CH—$R_6$, C=$R_7$ or C($R_4$)$R_5$ radical, $R_1$ denotes a hydrogen or halogen atom or an —NH—CO—$NR_{11}R_{12}$ radical in which $R_{11}$ is a hydrogen atom and $R_{12}$ is an alkyl radical, $R_2$ denotes a hydrogen atom, $R_3$ denotes a carboxyl, alkoxycarbonyl or carboxamido radical, $R_4$ denotes an alkyl radical, $R_5$ denotes an -alk-COOR$_{10}$ radical, $R_6$ denotes a hydrogen atom or a radical which is alk-Het, 2-oxo-2,5-dihydropyrrol-1-yl, 1-pyrrolyl substituted by —COOR$_{10}$ or —$NR_{14}R_{15}$, $R_7$ denotes a CH—$R_{19}$, NO-alk-COOR$_{10}$ or NOH radical, $R_{19}$ denotes a Het or phenyl radical substituted by —COOR$_{10}$, and either $R_{14}$ and $R_{15}$ are hydrogen atoms or $R_{14}$ is a hydrogen atom and $R_{15}$ is a —COR$_{22}$ radical in which $R_{22}$ is an -alk-COOR$_{10}$ or —NH—Ar radical or a salt thereof.

64. A pharmaceutical composition comprising a pharmaceutically effective amount of at least one compound of formula (I) according to claim 1 or a salt of a compound of formula (I), together with a pharmaceutically acceptable carrier.

\* \* \* \* \*

UNITED STATES PATENT AND TRADEMARK OFFICE
CERTIFICATE OF CORRECTION

PATENT NO. : 5,726,175
DATED : March 10, 1998
INVENTOR(S) : ALOUP et al.

It is certified that error appears in the above-indentified patent and that said Letters Patent is hereby corrected as shown below:

On the title page, item [54] and column 1, line 1, "[1,2-A]" should read --[1,2-a]--, and "[1,2-E]" should read --[1,2-e]--.

On the Title Page, Item [75], in the Inventors, line 1, "Le" should read --le--; and line 2, "Le" should read --le--.

Claim 1, column 41, line 54, "CH–$R_5$ or C=$R_6$" should read --CH–$R_6$ or C=$R_7$--.

Claim 1, column 42, line 60, "$R_5$" should read --$R_8$--.

Claim 1, column 43, line 40, " -alk-COOR'$_{10}$" should read ---alk-COOR$_{10}$--.

Claim 9, column 45, line 66, "HaI-Ra" should read --Hal-Ra--.

Claim 28, column 50, line 27, "–(2 –8 C)alkOH" should read ---(2 –6 C)alkOH--.

UNITED STATES PATENT AND TRADEMARK OFFICE
CERTIFICATE OF CORRECTION

PATENT NO. : 5,726,175
DATED : March 10, 1998
INVENTOR(S) : ALOUP et al.

It is certified that error appears in the above-identified patent and that said Letters Patent is hereby corrected as shown below:

Claim 44, column 55, line 25, "and-alk-$COOR_{10}$" should read --and -alk-$COOR_{10}$--.

Signed and Sealed this

Sixteenth Day of March, 1999

Q. TODD DICKINSON

Attest:

Attesting Officer

Acting Commissioner of Patents and Trademarks